United States Patent [19]
Miller et al.

[11] 4,061,919
[45] Dec. 6, 1977

[54] GAMMA CAMERA SYSTEM

[75] Inventors: Don W. Miller, Westerville; Mark S. Gerber, Columbus, both of Ohio

[73] Assignee: The Ohio State University, Columbus, Ohio

[21] Appl. No.: 702,981

[22] Filed: July 6, 1976

[51] Int. Cl.² .................................................. G01T 1/20
[52] U.S. Cl. .............................. 250/363 S; 250/369; 250/370
[58] Field of Search ...................... 250/363 S, 369, 370

[56] References Cited
U.S. PATENT DOCUMENTS 3,984,689 10/1976 Arseneau ........................ 250/363 S Primary Examiner—Harold A. Dixon
Attorney, Agent, or Firm—Sidney W. Millard

[57] ABSTRACT

A gamma camera system having control components operating in conjunction with a solid state detector. The detector is formed of a plurality of discrete components which are associated in geometrical or coordinate arrangement defining a detector matrix to derive coordinate signal outputs. These outputs are selectively filtered and summed to form coordinate channel signals and corresponding energy channel signals. A control feature of the invention regulates the noted summing and filtering performance to derive data acceptance signals which are addressed to further treating components. The latter components include coordinate and energy channel multiplexers as well as energy-responsive selective networks. A sequential control is provided for regulating the signal processing functions, of the system to derive an overall imaging cycle.

41 Claims, 35 Drawing Figures

GAMMA CAMERA SYSTEM

BACKGROUND

The field of nuclear medicine has long been concerned with techniques of diagnosis wherein radiopharmaceuticals are introduced into a patient and the resultant distribution or concentration thereof, as evidenced by gamma ray intensities, is observed or tracked by an appropriate system of detection. An important advantage of the diagnostic procedure is that it permits non-invasive investigation of a variety of conditions of medical interest. Approaches to this investigative technique have evolved from early pioneer procedures wherein a hand-held radiation counter was utilized to map body contained areas of radioactivity to more current systems for simultaneously imaging substantially an entire, in vivo, gamma ray source distribution. In initially introduced practical systems, scanning methods were provided for generating images, such techniques generally utilizing a scintillation-type gamma ray detector equipped with a focusing collimator which moved continuously in selected coordinate directions, as in a series of parallel sweeps, to scan regions of interest. A drawback to the scanning technique resides in the necessarily longer exposure times required for the derivation of an image. For instance, such time elements involved in image development generally are overly lengthy to carry out dynamic studies of organ function.

By comparison to the rectilinear scanner described above, the later developed "gamma camera" is a stationary arrangement wherein an entire region of interest is imaged at once. As initially introduced the stationary camera systems generally utilized a larger diameter sodium Iodide, Na I (TI) crystal as a detector in combination with a matrix of photomultiplier tubes. A multiple channel collimator is interposed intermediate the source containing subject of investigation and this scintillation detector crystal. When a gamma ray emanating from the region of investigative interest interacts with the crystal, a scintillation is produced at the point of gamma ray absorption and appropriate ones of the photomultiplier tubes of the matrix respond to the thus generated light to develop output signals. The original position of gamma ray emanation is determined by position responsive networks associated with the outputs of the matrix. For additional information concerning such cameras, see:

I. Anger, H.O., "A New Instrument For Mapping Gamma Ray Emitters," Biology and Medicine Quarterly Report UCRL-3653, 1957.

A continually sought goal in the performance of gamma cameras is that of achieving a high resolution quality in any resultant image. Further, it is desirable to achieve this resolution in combination with concomitant utilization of a highly versatile radionuclide or radiolabel, 99m-Technetium, having a gamma ray or photon energy in the region of 140 keV. A broadened clinical utility for the cameras also may be realized through the use and image identification of radiopharmaceuticals exhibiting more than one photon energy level. With such an arraignment, two or a plurality of diagnostic aspects simultaneously may be availed the operator. For example, in carrying out myocardial imaging, the above-identified 99m-Technetium might be utilized in conjunction with 111-Indium, the latter contributing photon energy in the regions of 173 and 247 KeV. Similarly, 81-Rubidium, exhibiting photon energy in the range of 350 KeV might be utilized in conjunction with 81-Krypton, the latter having gamma ray energy at about 120 KeV. The noted dual energy characteristic of 111-Indium also might be utilized to achieve two aspects of diagnostic data.

The resolution capabilities of gamma cameras incorporating scintillation detector crystals, inter alia, is limited both by the light coupling intermediate the detector and phototube matrix or array as well as by scatter phenomena of the gamma radiation witnessed emanating from within the in vivo region of investigation. Concerning the latter scattering phenomena, a degradation of resolution occurs from scattered photons which are recorded in the image of interest. Such photons may derive from Compton scattering into trajectories wherein they are caused to pass through the camera collimator and interact photoelectrically with the crystal detector at positions other than their point of in vivo derivation. Should such photon energy loss to the Compton interaction be less than the energy resolution of the system, it will effect an off-axis recordation in the image of the system as a photopeak photon representing false spatial information or noise. As such scattered photons record photopeak events, the noise increases and consequent resolution quality of the camera diminishes. For the noted desirable 140 KeV photons, the scintillation detector type camera energy resolution is approximately 15 KeV. With this resolution, photons which scatter through an angle from 0° to about 70° will be seen by the system as such photopeak events.

A continuing interest in improving the resolution qualities of gamma cameras has lead to somewhat extensive investigation into imaging systems incorporating relatively large area semiconductor detectors. Such interest has been generated principally in view of theoretical indications of an order of magnitude improvement in statistically limited resolution to provide significant improvements in image quality. In this regard, for example, reference may be made to the following publications: II. R. N. Beck, L. T. Zimmer, D. B. Charleston, P. B. Hoffer, and N. Lembares, "The Theoretical Advantages of Eliminating Scatter in Imaging Systems," *Semiconductor Detectors in Nuclear Medicine*, (P. B. Hoffer, R. N. Beck, and A. Gottschalk, editors), Society of Nuclear Medicine, New York, 1971, pp. 92–113.

III. R. N. Beck, M. W. Schuh, T. D. Cohen, and N. Lembares, "Effects of Scattered Radiation on Scintillation Detector Response," *Medical Radioisotope Scintigraphy*, IAEA, Vienna, 1969, Vol. 1, pp. 595–616.

IV. A. B. Brill, J. A. Patton, and R. J. Baglan, "An Experimental Comparison of Scintillation and Semiconductor Detectors for Isotope Imaging and Counting", *IEEE Trans. Nuc. Sci., Vol. NS*-19, No. 3, pp. 179–190, 1972.

V. M. M. Dresser, G. F. Knoll, "Results of Scattering in Radioisotope Imaging" *IEEE Trans. Nuc. Sci.*, Vol. NS-20, No. 1, pp. 266–270, 1973.

Particular interest on the part of investigators has been paid to detectors provided as hybridized diode structures formed basically of germanium. To derive discrete regions for spatial resolution of impinging radiation, the opposed parallel surfaces of the detector diodes may be grooved or similarly configured to define transversely disposed rows and columns, thereby providing identifiable discrete regions of radiation response. Concerning such approaches to treating the detectors, mention may be made of the following publications:

VI. J. Detko, "Semiconductor Dioxide Matrix for Isotope Localization", *Phys. Med. Biol.,* Vol. 14, No. 2, pp. 245–253, 1969.

VII. J. F. Detko, "A Prototype, Ultra Pure Germanium Orthogonal Strip Gamma Camera," *Proceedings of the IAEA Symposium on Radioisotope Scintigraphy,* IAEA/SM-164/135. Monte Carlo, October 1972.

VIII. R. P. Parker, E. M. Gunnerson, J. L. Wankling, and R. Ellis, "A Semiconductor Gamma Camera with Quantitative Output," *Medical Radioisotope Scintigraphy.*

IX. V. R. McCready, R. P. Parker, E. M. Gunnerson, R. Ellis, E. Moss, W. G. Gore, and J. Bell, "Clinical Tests on a Prototype Semiconductor Gamma-Camera," *British Journal of Radiology,* Vol. 44, 58–62, 1971.

X. Parker, R. P., E. M. Gunnerson, J. S. Wankling, R. Ellis, "A Semiconductor Gamma Camera with Quantitative Output," *Medical Radioisotope Scintigraphy,* Vol. 1, Vienna, IAEA, 1969, p. 71.

XI. Detko, J. F., "A Prototype, Ultra-Pure Germanium, orthogonal-Strip Gamma Camera," *Medical Radioisotope Scintigraphy,* Vol. 1, Vienna, IAEA, 1973, p. 241.

XII. Schlosser, P. A., D. W. Miller, M. S. Gerber, R. F. Redmond, J. W. Harpster, W. J. Collis, W. W. Hunter, Jr., "A Practical Gamma Ray Camera System Using High Purity Germanium," presented at the 1973 IEEE Nuclear Science Symposium, San Francisco, November 1973; also published in *IEEE Trans. Nucl. Sci.,* Vol. NS-21, No. 1 February 1974, p. 658.

XIII. Owen, R. B., M. L. Awcock, "One and Two Dimensional Position Sensing Semiconductor Detectors," *IEEE Trans. Nucl. Sci., Vol. NS-*15, June 1968, p. 290.

In the more recent past, investigators have shown particular interest in forming orthogonal strip matrix detectors from p-i-n semiconductors fashioned from an ultra pure germanium material. In this regard, reference is made to U.S. Pat. No. 3,761,711 as well as to the following publications:

XIV. J. F. Detko, "A Prototype, Ultra Pure Germanium, Orthogonal Strip Gamma Camera," *Proceedings of the IAEA Symposium on Radioisotope Scintigraphy,* IAEA/SM-164/135, Monte Carlo, October, 1972.

XV. Schlosser, P. A., D. W. Miller, M. S. Gerber, R. F. Redmond, J. W. Harpster, W. J. Collis, W. W. Hunter, Jr., "A Practical Gamma Ray Camera System Using High Purity Germanium," presented at the 1973 IEEE Nuclear Science Symposium, San Francisco, November 1973; also published in *IEEE Trans. Nucl. Sci., Vol. NS-*21, No. 1, February 1974, p. 658.

High purity germanium detectors promise numerous advantages both in gamma camera resolution as well as practicality. For instance, by utilizing high purity germanium as a detector, lithium drifting arrangements and the like for reducing impurity concentrations are avoided and the detector need only be cooled to requisite low temperatures during its clinical operation. Readout from the orthogonal strip germanium detectors is described as being carried out utilizing a number of techniques, for instance, each strip of the detector may be connected to a preamplifier-amplifier channel and thence directed to an appropriate logic function and visual readout. In another arrangement, a delay line readout system is suggested with the intent of reducing the number of preamplifiers-amplifier channels, and a technique of particular interest utilizes a charge splitting method. With this method or technique, position sensitivity is obtained by connecting each contact strip of the detector to a charge dividing resistor network. Each end of each network is connected to a virtual earth, charge sensitive preamplifier. When a gamma ray interacts with the detector, the charge released enters the string of resistors and divides in relation to the amount of resistance between its entry point in the string and the preamplifiers. Utilizing fewer preamplifiers, the cost and complexity of such systems is advantageously reduced. A more detailed description of this readout arrangement is provided in:

XVI. Gerber, M. S., Miller, D. W., Gillespie, B., and Chemistruck, R. S., "Instrumentation For a High Purity Germanium Position Sensing Gamma Ray Detector," *IEEE Trans. on Nucl. Sci., Vol. NS-*22 No. 1, February, 1975, p. 416

To achieve requisite performance and camera image resolution, it is necessary that substantially all sources of noise or false information within the system be accounted for. In the absence of adequate noise resolution, the performance of the imaging systems may be compromised to the point of impracticality. Until the more recent past, charge-splitting germanium detector arrangements have not been considered to be useful in gamma camera applications in consequence of thermal noise anticipated in the above-noted resistor divider networks, see publication VII, supra. However, as will be evidenced in the description to follow, such considerations now are moot.

Another aspect in the optimization of resolution of the images of gamma cameras resides in the necessarily inverse relationship between resolution and sensitivity. A variety of investigations have been conducted concerning this aspect of camera design, it being opined that photon noise limitations, i.e. statistical fluctuations in the image, set a lower limit to spatial resolution. Further, it has been pointed out that the decrease in sensitivity witnessed in conventional high resolution collimators may cancel out any improvements sought to be gained in image resolution. A more detailed discourse concerning these aspects of design are provided, for instance, in the following publications:

XVII. E. L. Keller and J. W. Coltman, "Modulation Transfer and Scintillation Limitations in Gamma Ray Imaging," *J. Nucl. Med.* 9, 10, 537–545 (1968)

XVIII. B. Westerman, R. R. Sharma, and J. F. Fowler, "Relative Importance of Resolution and Sensitivity in Tumor Detection," *J. Nucl. Med.* 9, 12 638–640 (1968)

Generally, the treatment of the signals derived at the entrance detection portion of gamma cameras involves a form of spatial or coordinate identification of photons reaching the detector and additionally, a form of analysis of the energy of radiation reaching the detector. Spatial analysis may be carried out by difference summing circuits, while energy determination is carried out by additive summing circuits. Further, pulse height analyzers may be utilized as one discriminating component of a system for determining the presence of true or false imaging information. In any of the systems both treating noise phenomena and seeking a high integrity of spatial information, a control is required which carries out appropriate noise filtering while segregating true from false information. In addition to the foregoing, it is necessary that the "through-put rate" of the system be maximized in order that it may accommodate a highest number of bits or pulses representing spatial and energy data.

Another operational phenomenon tending to derogate from the spatial resolution quality performance of the cameras is referred to as "aliasing". This phenomenon represents a natural outgrowth of the geometry of the earlier-noted orthogonal strip germanium detector. A more detailed discussion of this aspect of the gamma cameras is provided at:

XIX. J. W. Steidley, et al., "The Spatial Frequency Response of Orthogonal Strip Detectors," *IEEE Trans. Nucl. Sci.*, February, 1976.

To remain practical, it is necessary that the imaging geometry of stationary type gamma cameras provide for as large a field of view as practical. More particularly, such considerations require a camera field of view large enough to encompass the entire or a significant extent of the profiles of various organs of interest. Because of limitations encountered in the manufacture of detector crystals, for instance, high purity germanium crystals, the size of solid state detector components necessarily is limited. As a consequence, composite detector configurations are required which conjoin a plurality of smaller detector components to provide an imaging field of view or radiation acceptance geometry of effectively larger size. However, such union of a multitude of detector components must be carried out without the concurrent generation of noise phenomena and without a significant loss of image information validity and acuity. For instance, in the latter regard, spatial information must have a consistency of meaning across the entire extent of an ultimately displayed image of an organ, otherwise, clinical evaluation of such images may be encumbered. Preferred arrangements for inter-coupling the discrete detector components within an overall array thereof is described in a copending application for United States Patent by M. S. Gerber and D. W. Miller, entitled "Gamma Camera System With Composite Solid State Detector" filed Apr. 27, 1976, Ser. No. 680,754 and assigned in common herewith.

The control systems utilized with gamma cameras having multi-component detectors further are called upon to collect image data therefrom at an optimum rate while evaluating the validity thereof and assigning it an appropriate address function. Such address assignment may vary in nature depending upon the selected mode of circuit interrelationship of the discrete detector components with the array. An additional function of the control system is to identify the spatial position of the detector-photon interaction for select but different energy levels. This requires a technique for normalizing the spatial labels of such signals while properly evaluating the energy level states thereof as representing valid image information. The rapidity with which this data is treated, as by assigning spatial regional factors to it, as well as evaluating it for validity becomes a particularly important aspect of the control systems where they are contemplated for use in clinical dynamic function studies. With such studies, dynamic alterations in an image component occuring within any segment of the image area should be followed closely in correspondence with the actual movement of the image source. Accordingly, efficient image signal treatment by the camera system is required.

SUMMARY

The present invention is addressed to an improved system for imaging the distribution within a region of interest of isotopic materials emitting radiation. Characterized as a gamma camera, the system operates in conjunction with a solid state detector, for instance of the ultra-pure germanium variety, which is formed having a plurality of discrete components. These detector components are arranged in mutual adjacency to form a composite detector and, accordingly, are operationally associated with impedance deriving arrangements to provide spatial coordinate parameter outputs representing the spatial disposition of corresponding interactions of the radiation impinging upon the detector.

The association of the detector components may take on a variety of configurations. For example, the components are formed and arranged in the composite detector such that each has one of two oppositely disposed charge collecting surfaces positioned within a common plane for exposure to radiation. These components then are arranged to establish linearly oriented groupings of the respective surfaces, each of the groupings of surfaces being electrically intercoupled and associated with the noted impedance arrangement for providing coordinate outputs which may be designated as $x$- and $y$- designated coordinate parameter outputs. These outputs are derived from respective mutually orthogonally aligned and oppositely disposed ones of the groupings associated with a common detector component at which an interaction with radiation corresponding with the output occurs. Such an operational grouping of the components is generally referred to as being "row-column" in nature. The outputs of any predetermined grouping of the detector components are, in accordance with the invention, selectively filtered and summed to derive corresponding coordinate channel signals as well as an energy channel signal which have values related to the noted spatial disposition and given photon energy exhibited at an interaction with a given detector component. A control arrangement associated with the grouping regulates the noted summation and filtering and derives a data acceptance signal as well as carries out resetting functions to permit a next processing procedure to be carried out.

The system further includes spatial coordinate multiplexers and energy channel multiplexers which are arranged so as to be addressed by the noted coordinate channel and energy channel signals. Each of the multiplexers is connected for response to a coded actuating signal to provide proper transference of the channel signals to further processing treatment. In this regard, a process control arrangement including a memory circuit, receives the data acceptance signals and is arranged to selectively retain them in a serialized fashion. The memory circuit is actuable to derive the noted coded actuating signal in correspondence with the serialized data acceptance signals to effect the noted transference of the channel and energy signals. A sequential control means is provided for selectively controlling or actuating the process control and for regulating an overall operational cycle of the system. Further treating arrangements within the system respond to the transferred channel signals for deriving readout information representative thereof which may be used for clinical analysis purposes and the like.

As another object and feature, the invention further contemplates the provision of a storage arrangement within the control system which may be in the form of a series of sample and hold components serving, when in a receive mode, to receive the coordinate and channel signals derived from the noted multiplexers. Upon actuation to a hold mode, the signals are retained over a given interval while being asserted within additional signal treatment functions of the system. The noted sequential control function of the system is further utilized during this interval to effect the carrying out of the noted reset function associated with the control components immediately processing the outputs of the detector component groupings. In consequence, an improved throughput rate for the system is achieved to enhance the imaging capability of the camera.

Another object and feature of the invention is to provide a control system of the type described above wherein isotopic material sources of radiation, i.e. radiopharmaceuticals or the like, exhibiting more than one photon energy level may be provided for purposes of broadened clinical practicality. For such an arrangement, the imaging system incorporates components treating the noted spatial coordinate channel as well as energy channel signals transferred from the multiplexer function of the system and carries out a normalization operation over the spatial channel signals such that they are characterized as representing only accurate spatial information for imaging purposes. This operation is provided utilizing divider networks which are configured and arranged to, in effect, divide the spatial channel signals by their corresponding energy signal. The thus normalized signals then are transmitted to appropriate readout components of the system.

Another aspect and object of the invention provides evaluating features within the imaging system. For instance, an evaluating arrangement in the form of multichannel analyser is incorporated to evaluate and respond to the peak values of a each energy channel signal submitted thereto as transferred from the noted multiplexing functions and/or the sample and hold components. The analysis performed is one wherein each energy signal peak value is evaluated with respect to predetermined upper and lower level window criteria which are pre-established in accordance with the known photon energy levels of the isotopic material distribution being imaged. In the event of a failure of a given energy channel signal to meet this window criteria, the control feature of the invention carries out a noted reset function to effect a short cycle performance of the system, thereby permitting a more rapid processing of a new quantum of image information. In one embodiment, two evaluating stages are utilized, one associated with that circuitry immediately treating the outputs of a predetermined number of the detector components while the second evaluation is carried out following a first evaluation and subsequent to the transference of the signal into later treatment stages.

A further object of the invention is to provide an improved system for imaging the distribution of isotopic materials which utilizes a composite solid state detector arrangement of the "row-column" variety described hereinabove. In such embodiment, the spatial coordinate signals, which may be designated x- and y- coordinate signals which are derived from select groupings of detector components, for instance four, are initially summed and filtered as described above and in the course of such summation, a time derivative of the energy signal is provided from each x- coordinate output and y- coordinate output processing arrangement to generate corresponding data signals. These data signals are then transmitted to a coincidence network which, in turn, generates a pair code signal which, in turn, is submitted to the earlier described memory arrangement. Accordingly, the spatial coordinate aspects of the x- and y- channel signals are established within processing system to properly locate the resultant spatial information signals within a readout component.

Other objects of the invention will, in part, be obvious and will, in part, appear hereinafter.

The invention, accordingly, comprises the system and apparatus possessing the construction, combination of elements, and arrangement of parts which are an exemplified by the following detailed disclosure.

For a fuller understanding of the nature and the object of the invention, reference should be had to the following detailed description taken in conjunction with the accompanying drawings.

DETAILED DESCRIPTION

In the discourse to follow, the control system of the invention initially is described in conjunction with the arrangements utilized for physically accepting gamma radiation from a clinically determined region of interest. In particular, initial acceptance techniques for collimating such radiation as well as parameters required for such collimation are set forth. Following that discussion, the discourse sets forth techniques for achieving optimised system performance with respect to noise characteristics which otherwise would be encountered with the solid state detector arrangement of the invention. Looking additionally to techniques for improving through-put rate characteristics for the system, the discussion initially is concerned with a control over a detector arrangement incorporating only a one detector component. Following this basic description, however, preferred techniques are set forth for associating a plurality of solid state detector components within a predetermined array or mosaic configuration. Such configurations and operational criteria therefore being established, the discussion then looks to a control system which may operate with radiopharmaceutical sources of more than one detectible energy level and which serves to treat resulting signals as well as label and address them to achieve practical overall imaging fields of view while maintaining efficient signal treatment.

Figure 1:
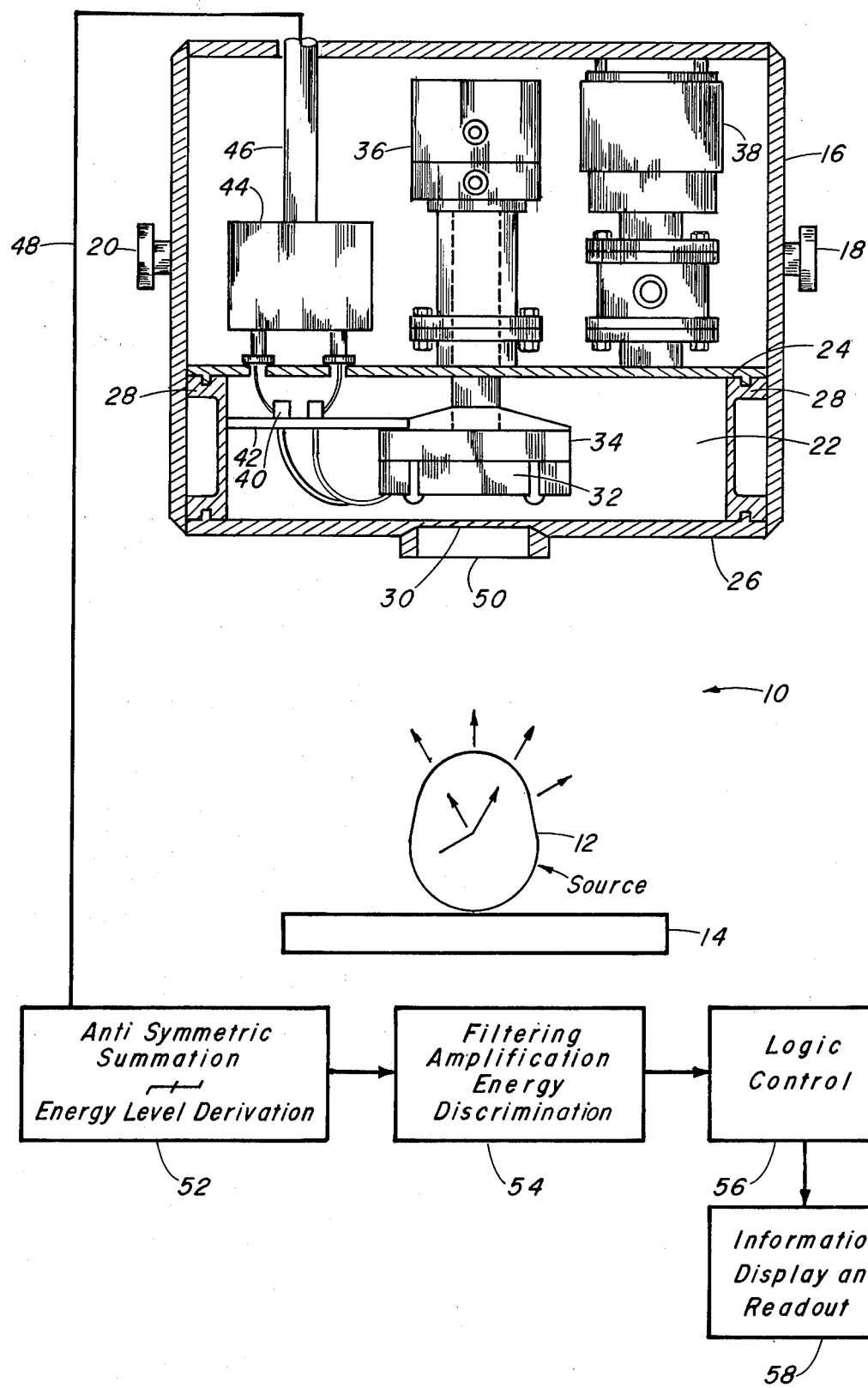
FIG. 1 is a schematic representation of a gamma camera arrangement as may utilize the improvement of the invention, showing, in block schematic form, general control functions.

As indicated in the foregoing, during contemplated clinical utilization, a gamma camera arrangement according to the instant invention is used to image gamma radiation within patients. Looking to FIG. 1, an exaggerated schematic representation of such a clinical environment is revealed generally at 10. The environment schematically depicts the cranial region 12 of a patient to whom has been administered a radio-labeled pharmaceutical, which pharmaceutical will have tended to concentrate within a region of investigative interest. Accordingly, radiation is depicted as emanating from region 12 as the patient is positioned on some supporting platform 14. Over the region 12 is positioned the head or housing 16 of a gamma camera. Extending outwardly from the sides of housing 16 are mounting flanges, as at 18 and 20, which, in turn, may be connected in pivotal fashion with an appropriate supporting assembly (not shown). Housing 16 also supports a vacuum chamber 22 defined by upper and lower vacuum chamber plates shown, respectively, at 24 and 26 conjoined with an angularly shaped side defining flange member 28. Lower vacuum chamber plate 26, preferably, is formed of aluminum and is configured having a thin entrance window portion 30, directly above which is provided an array of discrete solid state detector components, as shown generally at 32. Array 32, in turn, is operationally associated with the "cold finger" component 34 of an environmental control system, which preferably includes a cryogenic region refrigerating unit of a closed-cycle variety, shown generally at 36. An ion pump, as at 38, assures the integrity of the vacuum in chamber 22, such pump, in conjunction with the refrigerating unit 36, being mounted for association with chamber 22 through upper vacuum plate 24, the latter which may be formed, for instance, of stainless steel. Vacuum pump-down of the chamber 22 is accomplished by first using a sorption-type roughing pump, then using the ion pump shown to reduce and maintain the chamber pressure at $10^{-6}$ Torr or less.

Electronics incorporated within chamber 22 include preliminary stages of amplification, for instance field effect transistors (FET's) as at 40 which are mounted upon a plate 42 coupled, in turn, between cold-finger 34 and side channel 28. Thus connected, the plate 40 evidences a temperature gradient during the operation of the unit which provides a selected ideal temperature environment of operation for the amplification stages. The outputs of these stages are directed through subsequent stage electronics, shown within a housing 44, which, in turn, provides electrical communication to externally disposed control electronics through conduit 46 and line 48. To provide for appropriate operation, chamber 22 generally is retained at a temperature of, for instance, about 77° K, while the FET's, 40, mounted upon plate 42, are retained at about 130° K to achieve low noise performance.

Mounted outwardly of window portion 30 and in allignment with the detector array 32 is a collimator, shown generally at 50. During the operation of the gamma camera, radiation emanating from source 12 is spatially coded initially at collimator 50 by attenuating or rejecting off-axis radiation representing false image information. That radiation passing collimator 50 impinges upon detector array 32 and a significant portion thereof is converted to discrete charges or image signals. Detector array 32 is so configured as to distribute these signals to resistor chains as well as the noted preamplification stages 40 retained within chamber 22 to provide initial signals representative of image spatial information along conventional coordinate axes as well as representing values for radiation energy levels. This data then is introduced, as represented schematically by line 48, to filtering and logic circuitry which operates thereupon to derive an image of optimized resolution and veracity. In the latter regard, for instance, it is desired that only true image information be elicited from the organ being imaged. Ideally, such information should approach the theoretical imaging accuracy of the camera system as derived, for instance, from the geometry of the detector structure 32 and collimator arrangement 50 as well as the limitations of the electronic filtering and control of the system.

Image spatial and energy level signals from line 48 initially, are introduced into Anti-Symmetric Summation and Energy Level Derivation functions represented at block 52. As is described in more detail later herein, the summation carried out at block 52 operates upon the charges directed into the resistive chains or networks associated with the orthogonal logic structuring of detector array 32 to derive discrete signals or charge values corresponding with image element location. Additionally, circuitry of the function of block 52 derives a corresponding signal representing the energy levels of the spatial information. The output of block 52 is directed to Filtering Amplification and Energy Discrimination functions as are represented at block 54. Controlled from a Logic Control function shown at block 56, function 54 operates upon the signal input thereto to accommodate the system to parallel and series defined noise components through the use of Gaussian amplification or shaping, including trapezoidal pulse shaping of data representing the spatial location of image bits or signals. Similarly, the energy levels of incoming signals are evaluated, for instance, utilizing, multiple channel analyzer components controlled by logic circuitry at 56 to establish energy level windows for data received within the system. In this regard, signals falling above and below predetermined energy levels are considered false and are blocked. From Amplification and Discrimination stage 54 and Logic Control 56, the analyzed signals are directed into an Information Display and Readout Function, as is represented at block 58. Components within function block 58 will include display screens of various configurations, image recording devices, for instance, photographic apparatus of the instant developing variety, radiation readout devices and the like, which are controlled at the option of the system operator.

As outlined above, the instant description now looks in more detail to the configuration of the collimator structure 50. To facilitate such description, however, the structure of a single component within the detector array 32 is described in conjunction with FIG. 2. Later discussion and figures will reveal the interrelationships of such impedance networks and their equivalents as they are operatively associated with a multi-component detector array. Looking to that figure, an exaggerated pictorial representation of such a component of the detector array is revealed at 60. Detector component 60 may be fabricated from p-type high purity germanium by depositing an n-type contact on one face and a p-type contact on the opposite face of a rectangular planar crystal. Accordingly, a high purity germanium region of the crystal, as at 62, serves as an intrinsic region between p-type semiconductor region contacts 64 and n-type semiconductor region contacts as at 66. The intrinsic region 62 of the p-i-n detector components forms a region which is depleted of electrons and holes when a reverse bias is applied to the contacts. Grooves as at 68a-68c are cut into the continuous p-type contact or region at one face of the component to form strips of isolated p-type semiconductor material. On the opposite face of the detector component, orthogonally disposed n-type semiconductor strips similarly are formed through the provision of grooves 70a-70c. Configured having this geometry, the detector component 60 generally is referred to as an orthogonal strip detector or an orthogonal strip array semiconductor detector component. The electrode strips about each of the opposed surfaces of component 60, respectively, are connected to external charge splitting resistor networks revealed generally at 72 and 74. Resistor network 72 is formed of serially coupled resistors 76a –76e which, respectively, are tapped at their regions of mutual interconnection by leads identified, respectively, at 78a–78d extending, in turn, to the orthogonal strips. The opposed ends of network 72 terminate in preamplification stages 80 and 82, the respective outputs of which, at 84 and 86, provide spatial output data for insertion within the above-described summation and energy level derivation function 52 to provide one detector component orthogonal or coordinate output, for instance, designated as a y-axis signal.

In similar fashion, network 74 is comprised of a string of serially coupled resistors 88a–88e, the mutual interconnections of which are coupled with the electrode strips at surface 66, respectively, by leads 90a–90e. Additionally, preamplification stages as at 92 and 94 provide outputs, respectively, at lines 96 and 98 carrying spatial data or signals representative of image information along an x axis or axis orthogonally disposed with respect to the output of network 72.

With the assertion of an appropriate bias over detector component 60, as described in U.S. Pat. No. 3,761,711, any imaging photon absorbed therewithin engenders ionization which, in turn, creates electron-hole pairs. The charge thusly produced is collected on the orthogonally disposed electrode strips by the bias voltage and such charge flows to the corresponding node of the impedance networks 72 and 74. Further, this charge divides in proportion to the admittance of each path to the virtual ground input of the apropriate terminally disposed preamplification stage. Such charge-sensitive preamplification stage integrates the collected charge to form a voltage pulse proportional to that charge value. Assigning charge value designations $Q_1$ and $Q_2$, respectively, for the outputs 98 and 96 of network 74, and $Q_3$ and $Q_4$, respectively, for the output lines 84 and 86 of network 72, the above-noted Summation and Energy Level Derivation functions for spatial and energy data may be designated. In this regard, the x-position of each diode defined by the orthogonal strip geometry is found to be proportional to $Q_1$, $Q_2$, and their difference i.e. $(Q_1-Q_2)$, and the y-position is proportional to $Q_3$, $Q_4$, and their difference i.e. $(Q_3-Q_4)$. The energy of the incident gamma ray is proportional to $Q_1+Q_2$, and $(Q_3+Q_4)$, and $[(Q_1+Q_2) - (Q_3+Q_4)]$ or in the latter expression, $[(Q_3+Q_4) - (Q_1+Q_2)]$. As noted above, the operational environment of the detector array 32 and associated amplification stages is one within the cryogenic region of temperature for purposes of avoiding Johnson noise characteristics and the like.

Figure 3:
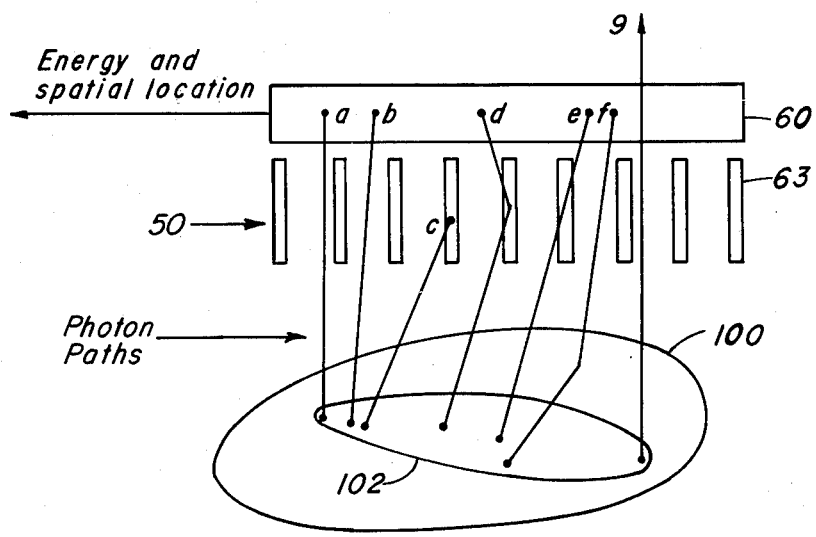
FIG. 3 is a schematic representation of a solid state strip detector and a schematic collimator functionally associated therewith as such system components relate to a radiation source within a region of clinical interest.

As a prelude to a more detailed consideration of the spatial resolution of gamma radiation impinging upon the entrance components of the gamma camera, some value may be gleaned from an examination of more or less typical characteristics of that impinging radiation. For instance, looking to FIG. 3 a portion of a patient's body under investigation is portrayed schematically at 100. Within this region 100 is shown a radioactively tagged region of interest 102, from which region the decay of radiotracer releases photons which penetrate and emit from the patient's body. These photons are then spatially selected by a portion of collimator 50 and individually detected at component 60 for ultimate participation in the evolution of an image display. The exemplary paths of seven such photons are diagrammed in the figure, as at a-g, for purposes of illustrating this initial function which the camera system is called upon to carry out. In this regard, the function of collimator 50 is to accept those photons which are traveling nearly perpendicular to the detector, inasmuch as such emanating rays provide true spatial image information. These photons are revealed at ray traces, a, and, b, showing direct entry through the collimator 50 and appropriate interaction coupled with energy exchange within detector component 60. Photon path, c, is a misdirected one inasmuch as it does not travel perpendicularly to the detector. Consequently, for appropriate image resolution such path represents false information which should be attenuated, as schematically portrayed. Scattering phenomena within collimator 50 itself or the penetration of the walls thereof allows "non-collimated" photons, i.e. ray traces, d, and e, to reach the detector. Photon path trace, f, represents Compton scattering in the patient's body. Such scattering reduces the photon energy but may so redirect the path direction such that the acceptance geometry of the camera, including collimator 50, permits the photon to be accepted as image information. Inasmuch as the detector component 60 and its related electronics measure both the spatial location and energy of each photon admitted by the collimator, the imaging system still may reject such false information. For example, in the event of a Compton scattering of a photon either in the patient or collimator, the energy thereof may have been reduced sufficiently to be rejected by an energy discrimination window of the system. Photon path, g, represents a condition wherein component 60 exhibits inefficient absorption characteristics such that the incident photon path, while representing true information, does not interact with the detector. As is apparent from foregoing, each of the thousands of full energy photons which are absorbed at the detector ultimately are displayed at their corresponding spatial location on an imaging device such as a cathode ray tube to form an image of the source distribution within region 102 of the patient. Of course, the clinical value of the gamma camera as a diagnostic implement is directly related to the quality of ultimate image resolution.

Figure 4A:
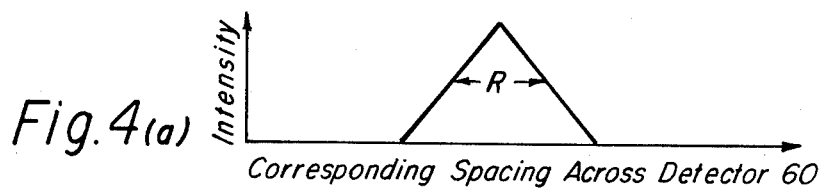
FIGS. 4(a)–4(c) are a schematic and graphical representation of the fundamental geometry associated with the interrelationship of a multi-channel collimator and a solid state detector.
Figure 4B:
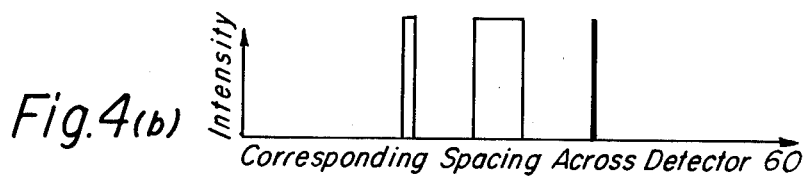
Figure 4C:
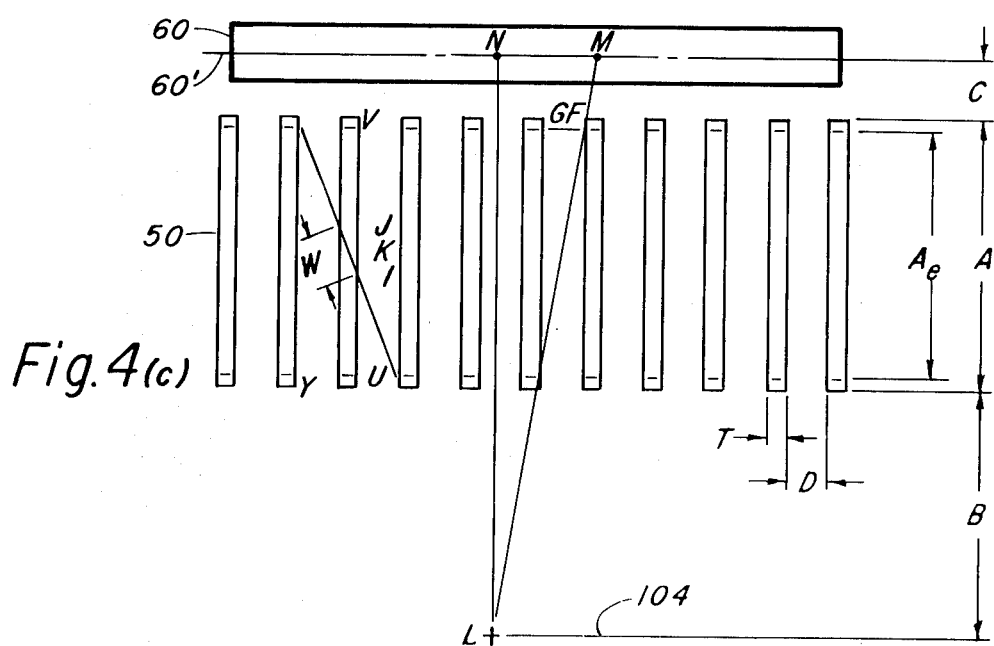

As is revealed from the foregoing discourse, the imaging resolution of the camera system is highly dependent upon the quality of collimation exhibited at the entrance of the camera by collimator 50. Generally, collimator 50 is of a multichannel, parallel-hole variety, its performance being dictated by its fundamental geometric dimensions, the material with which it is formed, and the technique of its fabrication. Referring to FIGS. 4(a)–4(c), a designation of the geometric aspects of collimator 50, as such aspects relate to photon path travel, and spatial intensity distribution over the corresponding spatial axis of detector component 60 are shown schematically. FIG. 4(b) shows the photon intensity distribution at the mid-plane 60' of the detector due to a line source of radiation at distance B from the collimator 50 outwardly disposed plane defining side. Note that the source position is designated "L." Source point, L, is located, for purposes of the instant analysis, within a plane 104 lying parallel to the outwardly disposed plane defining side of collimator 50 as well as its inwardly disposed plane defining side and the plane defined by the midpoint 60' of detector 60. The intensity distribution pattern of photons, revealed in FIG. 4(b), is provided under the assumption that the collimator 50 is fixed in position. FIG. 4(a), on the other hand, assumes that the collimator 50 moves during an exposure and produces, in consequence, a triangular intensity distribution pattern of photons. A location of value "R" designates a full width at half maximum (FWHM) spatial resolution. Such spatial or position resolution capability of the camera system may be defined utilizing several approaches. However, for the latter designation, FWHM, is derived from a consideration that if a very small spot of radiation exits at the object plane, the image generally will be a blurred spot with radially decreasing intensity. The position resolution then is defined as twice the radial distance at which the intensity is half of the center intensity.

Looking in particular to FIG. 4(c), considering the similar triangles EFG and LMN, the resolution of collimator 50 generally may be expressed as:

$$R_c = (D/A_E)(A + B + C) \tag{1}$$

where $A$ = the collimator thickness,
$A_E$ = the effective collimator thickness due to septal penetration,
$B$ = the source to collimator distance,
$C$ = the collimator to detector midplane distance and
$D$ = the effective diameter of each channel within the multi-channel collimator Effective diameter, D, is considered to be the square root of the cross-sectional area of a given collimator channel multiplied by 1.13

The effective collimator thickness is given approximately by:

$$A_E = A - \frac{2}{\mu(E)} \tag{2}$$

where $\mu(E)$ is the attenuation coefficient of the collimator material at a photon energy, E.

For a given collimator material, sufficiently thick septal walls are required to reduce the number of photons or gamma rays that enter within a given collimator channel, penetrate the septal wall thereof and exit through an adjacent or other channel opening. Looking to FIG. 4(c), one such gamma ray or photon path is traced as $\overline{UV}$. Note, that for this condition, the photon or ray passes through a collimator vane or channel side of thickness, T, along a minimum septal distance, W, thereby allowing the ray or photon to exit from a channel adjacent the channel of initial entrance. The fraction of photons or rays traveling $\overline{UV}$ that actually penetrate the septal wall is given by the penetration fraction:

$$P = \exp(-\mu(E) W). \quad (3)$$

It is considered the practice of the art to design the collimator structure such that the penetration fraction, P, is given a value less than about 5%. In this regard, mention may be made of the following publication:

XX. H. O. Anger, "Radioisotope Cameras," *Instrumentation in Nuclear Medicine*, G. J. Hine, ed. Vol. 1, Academic Press, New York, 485–552 (1967).

The minimum septal distance, W, is found from the similar triangles IJK and UVY approximatley as:

$$W = \frac{AT}{2D + T} \quad (4)$$

by assuming A is greater than 2D + T where T, as noted above, is the septal wall thickness. Solving equations (3) and (4) for the septal wall thickness, T, gives:

$$T = \frac{-2D \ln P}{\mu(E) A + \ln P} \quad (5)$$

The value, T, as set forth in equation (5) serves to define that minimal septal thickness for collimator 50 which is required for a given penetration fraction, P.

The geometric efficiency of the collimator is defined as the ratio of the number of gamma rays or photons which pass through the collimator to the number of photons or gamma rays emitted by the source. Described in terms of the collimator parameters, such efficiency may be given by:

$$\phi_S = \left[ \frac{KD^2}{A_E(D + T)} \right]^2 \quad (6)$$

where K = 0.238 for hexagonally packed circular holes and 0.282 for square holes or chambers in a square array.

As described above, the clinical value of the gamma camera imaging system stems importantly from the systems' capability for achieving quality image resolution. Given the optimum image resolution which is practically available, it then is desirable to provide a design which achieves a highest efficiency for that resolution. For a collimator design, it is desirable to provide a low septal penetration fraction as well as a practical fabrication cost. Further, an inspection of equations (1) and (6), given above for collimator resolution and geometric efficiency, respectively, reveals that as resolution is enhanced, the efficiency of the collimator is diminished. It has been determined that a multichannel, parallel-hole collimator, the channels of which are configured having square cross sections represents a preferred geometric design feature. In this regard, where the latter are compared with collimator channels formed having round holes, hexagonally packed arrays or hexagonally packed bundles of tubes all of given identical dimensions, resolution remains equivalent, but the efficiency of the preferred square cross sectional channel array will be a factor of 1.4 times greater than the round hole design, while the efficiency of the hexagonally packed bundle of tubes will be intermediate the efficiency value of the above two designs. Consequently, as noted above, on the basis of maximum efficiency at a desired resolution, the square hole cross sectional chamber design is preferred.

Concerning the materials which may be selected for constructing the collimator, those evidencing a high density, high atomic number characteristic are appropriate for consideration. In particular, mention may be made of tungsten, tantalum and lead for the purpose at hand. The primary criterion for the material is that of providing a short mean free path at the photon energy level of interest. For the desirable energy level of 140 keV, the mean free path for photon attenuation is 0.012 inch in tungsten, 0.015 inch in tantalum and 0.016 inch in lead. Accordingly, for a selection based upon a mean free path for attenuation, tungsten represents the optimum collimator material. Heretofore, however, pragmatic considerations of machineability or workability have required a dismissal of the selection of tungsten and/or tantalum for collimator fabrication. For instance, for multi-channel collimators having round channel cross sections, tungsten and tantalum are too difficult and, consequently, too expensive for drilling procedures and, in general, hexagonally packed arrays providing such cross sections are restricted to fabrication in lead. Similarly, other designs formed out of the desired materials do not lend themselves to conventional machining and forming techniques, the cost for such fabrication being prohibitive even for the sophisticated camera equipment within which the collimator units are intended for utilization.

Figure 5:
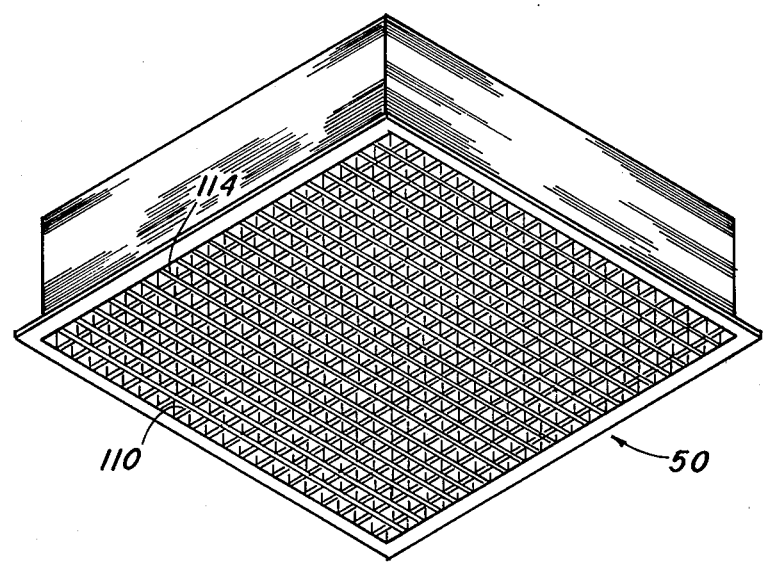
FIG. 5 is a pictorial representation of a collimator array which may be utilized with the system of invention.
Figure 6:
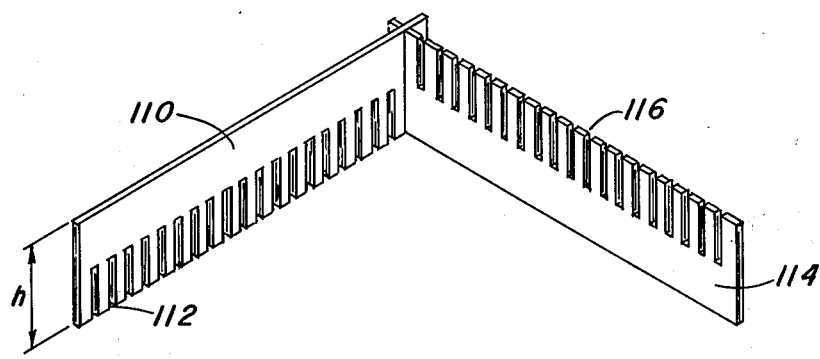
FIG. 6 is a pictorial view of two internested members of the collimator of FIG. 5.

In the instant preferred arrangement, a square hole collimator design, fabricable utilizing the optimum material tungsten, is provided. Revealed in perspective fashion in FIG. 5, the collimator is shown to comprise an array of mutually parallel adjacently disposed channels having sides defining a square cross section. These channels extend to define inwardly and outwardly disposed sides which are mutually parallel and the channels are formed axially normally to each of these side planes. The highly desirable square structure shown in FIG. 5 is achieved utilizing the earlier described preferred tungsten material or tantalum, such mateials normally being difficult or impractical to subject to more conventional manufacturing procedures. However, practical assembly of the collimator array 50 is achieved through the use of a plurality of discrete rectangularly shaped sheet members, as are revealed in the partial assembly of the collimator 114 shown in FIG. 6. Referring to that figure, note that member 110 is formed as a flat rectangular sheet of height, h, corresponding with desired collimator thickness, A. Formed inwardly from one edge of member 110 are a plurality of slots spaced in regularly recurring parallel fashion and identified generally at 112. Slots 112 are formed having a height equivalent to $h/2$ and are mutually spaced to define a pitch or center-to-center spacing D + T. The slots are formed having a width of T +e, where e will be seen to be a tolerance. When the plurality of sheet members, for instance, as shown at 110 and 114 are vertically reversed in mutual orientation and the corresponding slots, respectively, as at 112 and 116 are mutually internested as shown, the collimator may be built-up to desired dimensions without recourse to elaborate forming procedures. Note that the width of slots 112 and 116 closely approximates the width of each of the sheet members within the array with a controlled allowance for tolerances. In determining the value for the above described pitch of the regularly recurring slots within the sheet members, assuming resolution criteria are met, a spacing may be selected to match the center-to-center electrode strip spacing of a detector component 60 or a multiple thereof so that the septal walls for the collimator 50 can be aligned with less active grooves formed within the detector. Practical fabrication techniques are available for forming the slots as exemplified at 112 and 116. In particular, chemical milling or chemical machining techniques are available for this purpose. With such techniques, a wax type mask is deposited over the sheets to be milled, those material portions designated for removal being unmasked. The sheets then are subjected to selected etchants whereupon the slots are formed. Following appropriate cleaning, the sheet members then are ready for the relatively simple assembly build-up of a completed collimator. Through the use of such chemical milling techniques, desired tolerances in forming the slots are realizable. By utilizing the collimator structure shown in combination with optimal tungsten sheet material, a computable 35 to 40 percent improvement in collimator efficiency may be gained over round hole, hexagonally packed lead collimators of identical dimension, as well as a 50 to 80 percent improvement in septal penetration characteristics and an average 5% improvement in geometric resolution. The collimator fabrication technique and structure are seen to offer several advantages over more conventional collimators structures. As evidenced from the foregoing, such advantages include the availability to the design of the superior shielding capabilities of tungsten; a simplicity of component design and consequent ease of assembly and the use of optimal square hole chamber geometry for maximum geometrical efficiency. However, to achieve optimal performance, the assembly technique necessarily introduces small gaps at the intersections of the septal walls of a completed collimator structure. These gaps exist by virtue of the tolerances required for the interlocking fit of the septal wall and the effect of gamma ray streaming through such gaps should be considered.

In earlier commentary herein, it has been noted that a septal penetration of five percent or less of impinging gamma radiation is preferred for collimator design. It follows, therefore, that the streaming factor for the particular collimator structure at hand should be assigned the same configurational parameter in the interest of desired unity of system design. Through utilization of a geometric analysis of a worst case condition, requisite lowest tolerance required for the interlocking fit of the septal walls and for a desired source to collimator distance can be derived. Such analysis will reveal that the slot tolerance should preferably be no more than 0.001 inch and, more preferably, should be less than that to the extent of practical milling application.

In the discourse given heretofore concerning the functional inter-relationships of collimator 50 and detector array 32, no commentary was provided concerning the effect of the discrete electrode strips of the detector upon ultimate image resolution. It has been determined that, by virtue of their geometric configuration, orthogonal strip detectors, without appropriate correction, will introduce "alias" frequency components into the output of the system. For instance, in a purely linear system, the output of the camaera would consist of the same spatial frequency components as the input except with the possibility of reduced contrast. Looking to FIGS. 7(a)–(c), the aliasing phenomenon is demonstrated in connection with an exemplary and schematic representation of a strip electrode detector 130. In this worst case representation, no collimator is present and the electronic resolution is less than one strip width. Looking to FIG. 7 (a), a source distribution is shows as may be obtained, for instance, utilizing three discrete collimated point sources spaced at equal distances of 1.5 times the strip spacing. The reciprocal of the periodic spacing, $l$ of the components or detector strips depicted may be represented as, $1/l$ or $v_s$. The source distribution shown in the subject figure is one with primary frequency components of $v_1 = 0$ and $v_2 = 2v_s/3$. Here, $v_1$ represents a zero frequency component which represents the average value of the source distribution and $v_2$ represents the frequency which corresponds to the reciprocal of the spacing between the three collimated point sources. Such source input is provided in the instant representation presentation inasmuch as it combines the three qualities which accentuate an aliasing phenomenon, namely, a periodic input, 100% contrast, and a high signal-to-noise ratio.

Figure 7A:
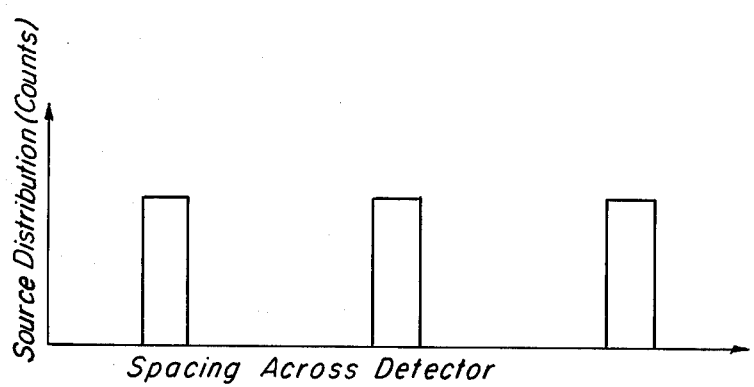
FIGS. 7(a)–7(c) respectively and schematically depict representations of a source distribution as related with the geometry of an orthogonal strip detector and image readouts for illustrating aliasing phenomena.
Figure 7B:
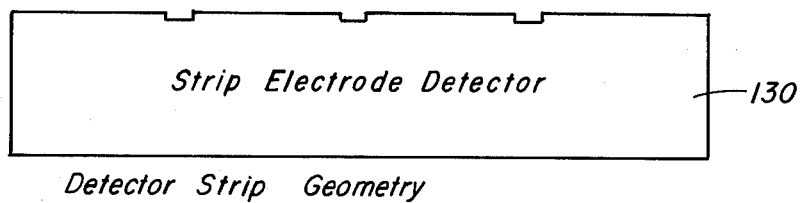
Figure 7C:
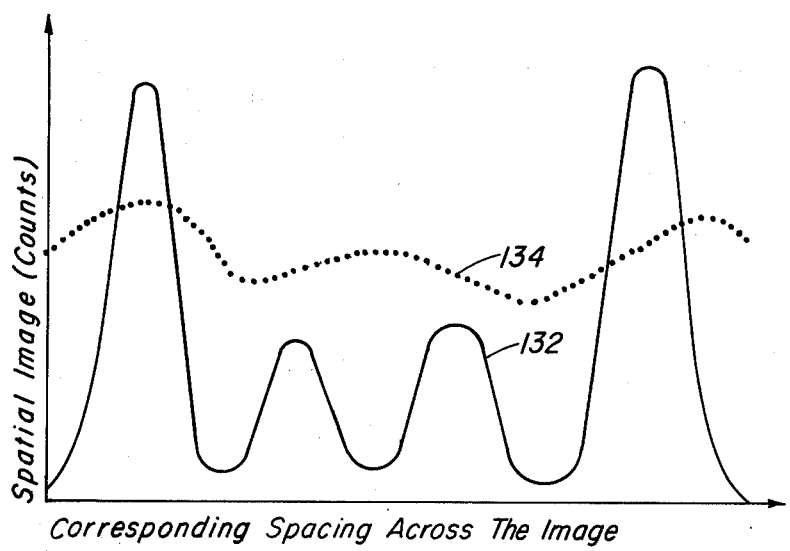

FIG. 7(b) reveals a portion of strip electrode detector 130 having the earlier described detector geometry or region grooves aligned with respect to the input signals depicted at FIG. 7(a). The onedimensional spatial image which may be derived, for instance, from a multi-channel analyzer is shown in FIG. 7(c) as curve 132. By comparison, the corresponding spatial image which would be received within a system incorporating a collimator capable of resolving the input signal, a detector with strip spacing satisfying the anti-aliasing criterion and an anti-aliasing electronic channel, is revealed at 134. The image shows no aliased components.

Looking more particularly to the aliasing phenomenon represented at curve 132, the four lowest spatial frequency components revealed are:

1. a component at $v = 0$, a zero frequency component which represents the average value of the four peaks;
2. a component at $v = 2v_s/3$, which is the frequency equal to the reciprocal of the spacing between one of the two outer peaks and the average position of the two inner peaks;
3. a component at $v = v_s$, which is the frequency equal to the reciprocal of the spacing between each of the four peaks; and
4. a component at $v = v_s/3$, which is the frequency equal to the reciprocal of the spacing between the two outer peaks.

The first two components above are the fundamental source components, while the second two compoents are aliased components of the fundamental source components centered at the first harmonic of the strip sampling frequency.

Figure 8A:
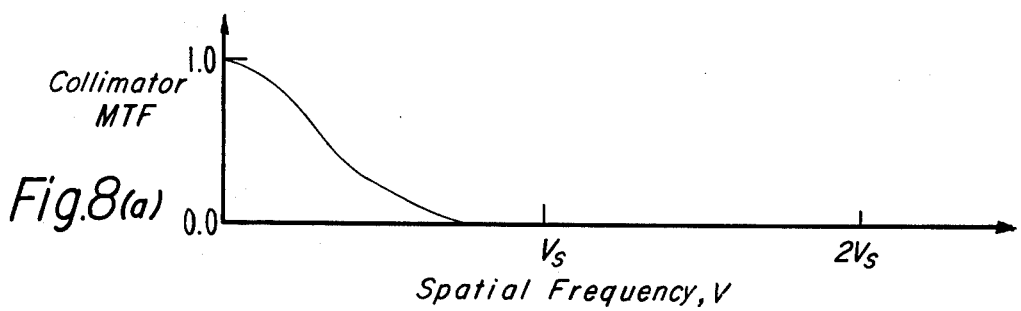
FIGS. 8(a)–8(d) portray vertically aligned graphs relating modulation transfer function with respect to resolution as such data relates to aliasing phenomena, FIG. 8(a) showing collimator modulation transfer function (MTF$_c$) with FWHM resolution of 1.331, FIG. 8(b) showing a consequent alias frequency spectrum which is processed by the electronics of the camera system, FIG. 8(c) showing electronic MTF for given resolutions, and FIG. 8(d) showing camera system MTF's revealing aliasing introduced by the orthogonal strip solid state detector.
Figure 8B:
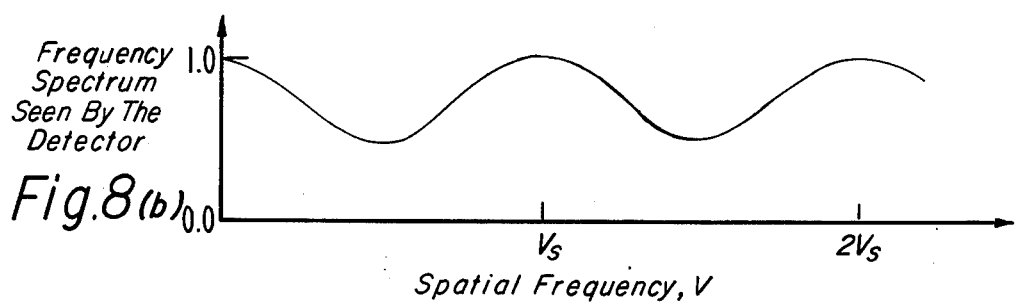
Figure 8C:
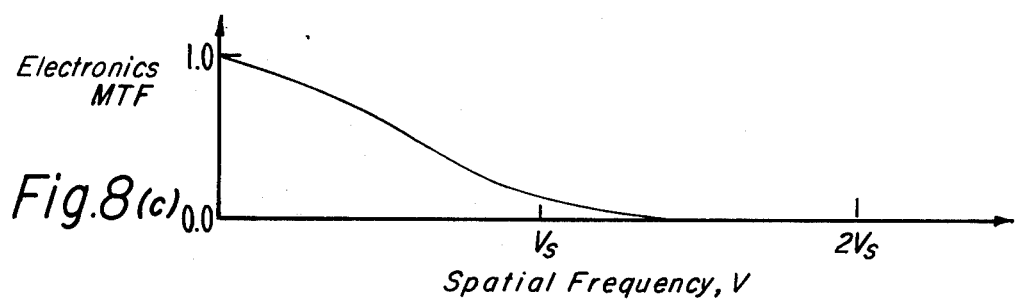
Figure 8D:
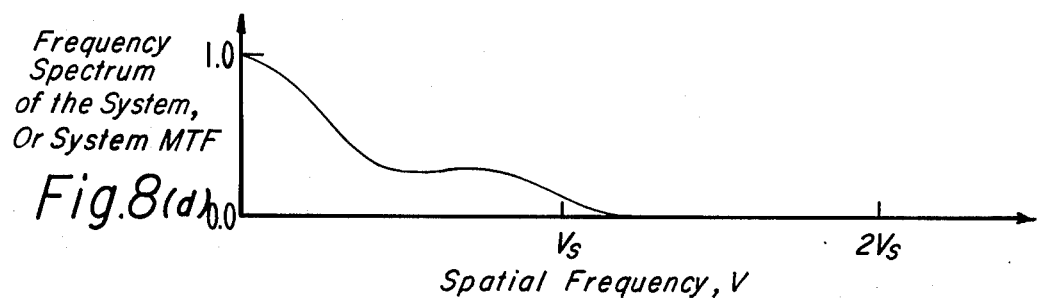

As a prelude to considering a typical representation of the spatial frequency response of a one-dimensional gamma camera as revealed in FIGS. 8(a) – (d) the modulation transfer functions (MTF) merit comment. As described in detail in publication (III) hereinabove, the MTF is a measure of spatial resolution that can be defined for linear systems and which takes into account the shape of an entire line spread function. The rationale for such description of spatial response arises from the fact that any object and its image can be described in terms of the amplitudes and phases of their respective spatial frequency components. The MTF is a measure of the efficiency with which modulation or contrast at each frequency is transferred by the imaging system from the object to the image. This is analogous to the temporal frequency response of an electronic amplifier of filter. Looking now to FIGS. 8(a) – 8(d) MTF is plotted against spatial frequency, ν, for a series of stages within a gamma camera not accommodating for aliasing phenomena. In FIG. 8(a) a collimator modulation transfer function (MTF$_c$) with FWHM resolution of 1.33$l$ is revealed, i.e., the curve distribution, incorporating some high frequency components, is representative of the signal passed to the semiconductor detector of the camera. FIG. 8(b) reveals the output frequency spectrum of the detector which is seen by the spatial channel electronics of the camera system. An aliased frequency spectrum is revealed, the input frequency spectrum being present in the output, centered at zero frequency and additional side bands of the primary input component are present, centered at integer multiples of the strip spacing or sampling frequency, $\nu_2 = 1/l$. FIG. 8(c) represents the MTF of the electronics of the system, i.e., the transfer function of the spatial channel electronics, while FIG. 8(d) shows the product of the MTF values of the curves of FIGS. 8(b) and 8(c). Accordingly, the curve of FIG. 8(d) shows the spatial frequency response of the entire system, including the introduction of spurious spatial frequency content in the system MTF, represented in the figure as the bump in the frequency range slightly below $\nu_s$.

Figure 9A:
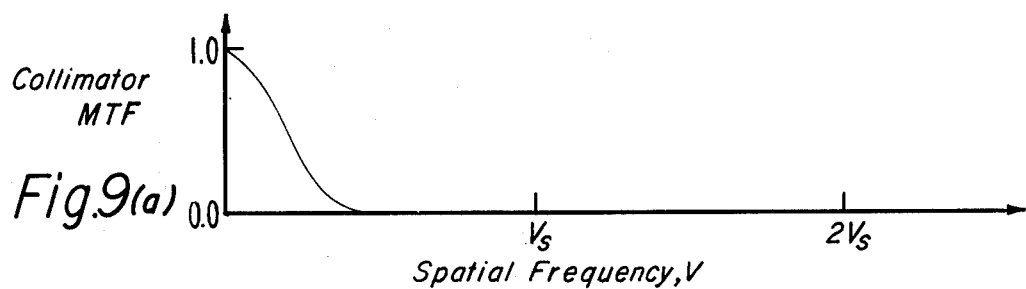
FIGS. 9(a)–9(d) provide curves showing the results of aliasing correction as compared with the curves of FIGS. 8(a)–8(d), FIG. 9(a) looking to collimator design as an anti-aliasing filter, FIG. 9(b) showing a consequent aliasing frequency spectrum which is processed by the electronics of the system, FIG. 9(c) showing the consequence of electronics used for anti-aliasing postfiltering, and FIG. 9(d) showing total system MTF revealing the elimination of aliasing phenomena.
Figure 9B:
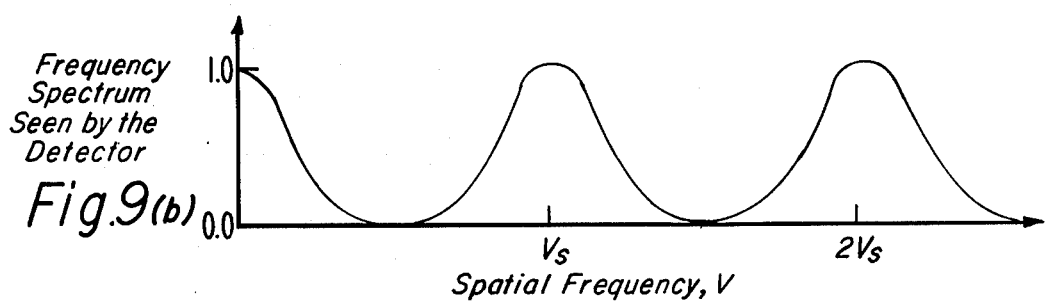
Figure 9C:
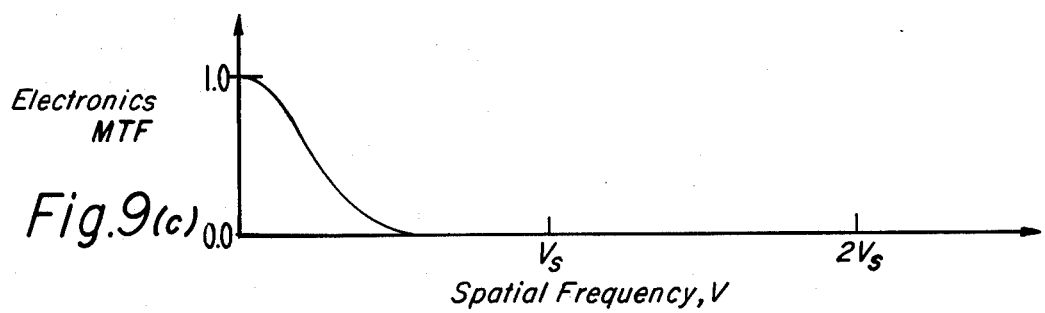
Figure 9D:
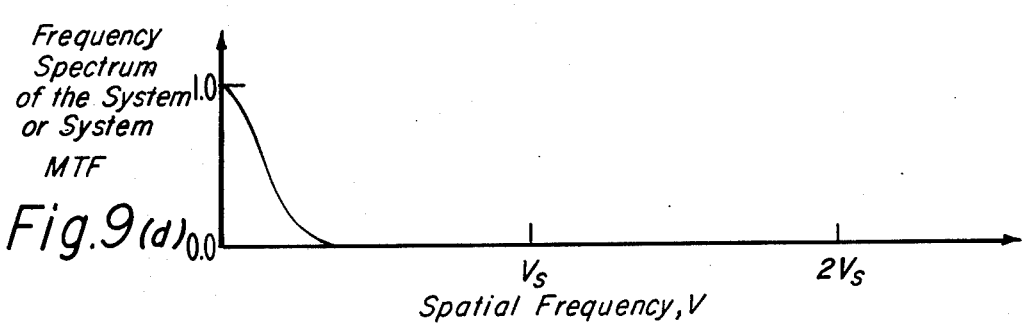

Looking by comparison now to FIGS. 9(a) – (d) the effect of inserted correction on the part of the collimator design and structure of the instant invention is revealed. The collimator 50 design is selected to provide an MTF prefilter to limit the spatial frequency content seen by the detector 32 to frequencies less than $\nu_s/2$. Accordingly, FIG. 9(a) reveals that the collimator MTF is forced to a zero value at spectrum position $\nu_s/2$. Such design insures that the fundamental input frequency components and the first harmonic frequency components centered at $\nu_s$ do not overlap and this condition obtains in FIG. 9(b), that Figure revealing the alis frequency spectrum which is processed by the electronic pickoff arrangement of the camera from the detector. The spatial channel electronics complete the anti-aliasing filter system by insuring that no spatial frequencies greater than $\nu_s/2$ are passed to the imaging system of the camera. Such post-filtering of the electronics is illustrated in FIG. 9(c). The product of MTF conditions represented by FIGS. 9(b) and 9(c) again are represented in FIG. 9(d) which, particularly when compared with the corresponding FIG. 8(d) reveals the elimination of aliasing phenomena.

Turning now to the prefiltering or corrective functions carried out by the collimator in controlling aliasing phenomena, it may be observed from the foregoing that the system resolution of an orthogonal strip germanium detector type gamma camera is determined by the collimator resolution, the strip width spacing, and the resolution of the spatial channel readout electronics. The collimator is assumed to have a Gaussian point spread function (PSF) and FWHM spatial resolution $R_c$. The value of $R_c$ should be equal to or greater than about 1.7 ($l$), where $l$ is the center-to-center strip spacing in one dimension of the detector. A more detailed discussion of the derivation of this value is provided in the folowing publication:

XXI. J. W. Steidley, et al., "The Spatial Frequency Response of Orthogonal Strip Detectors," IEEE Trans. Nuc. Sci., February, 1976.

Looking now to the specific design parameters of the collimator of the invention, it may be recalled that collimator resolution, $R_c$, has been derived geometrically at equation (1) given hereinabove. By not substituting the ideal valuation, 1.7 ($l$) determined for anti-aliasing prefiltering on the part of the collimator, the inventive collimator geometry or structure may be defined. Accordingly, the collimator is defined under the following expression:

$$1.7\ (l) \leq \frac{D}{A_E(A + B + C)} \qquad (7)$$

The collimator further can be defined utilizing equation (5) above for septal wall thickness once the values of the parameter of equation (7) are determined. Further, given the value, $R_c$, for collimator resolution and the geometric parameters determined thereby as described above, the collimator geometric efficiency, $\phi_s$, as given in equation (6) above, can be applied to further maximize the performance of the collimator. Additionally, it may be noted that by suppressing frequencies above $\nu_s/2$ input signal contributions to aliasing phenomena are accommodated for.

As has been alluded to earlier herein, discounting entrance geometry, the orthogonal strip position-sensitive detector is resolution limited by noise associated with the detector as well as the charge dividing network. Consequently, it is necessary to consider the noise characteristics of the system from the standpoint of minimizing the effects thereof upon resolution as well as treating such phenomena to derive desired imaging effects. Generally, it may be concluded that the resistor network is the dominant source of noise within the electronic spatial channel of the system, while the resistor network, coupled with the detector leakage current, represents the dominant noise source in the system's energy channel. As will become more apparent as the instant description unfolds, spatial noise dominantly is electrically parallel in nature, whereas energy channel noise may be considered to be electrically series in nature. In the discourse to follow, noise treatment and the like are described in conjunction with the singular detector component described heretofore in connection with FIG. 2, in the interest of clarity and simplification. In later portions of the instant discussion, however, the control system of the camera will be seen to be described in conjunction with detector component array embodiments.

Figures 10, 11:
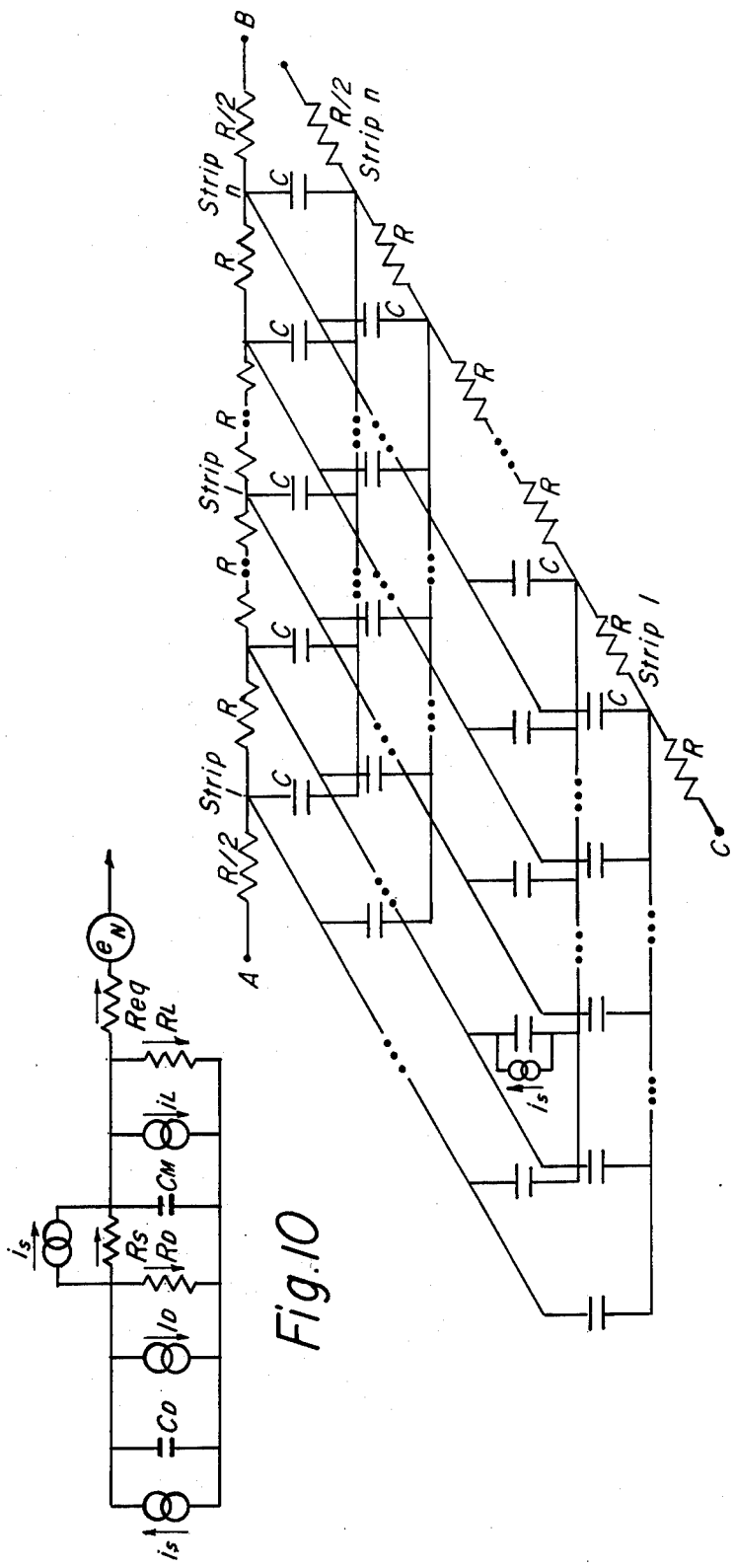
FIG. 10 is an equivalent noise model circuit for solid state detectors as utilized in accordance with the instant invention.
FIG. 11 is a circuit model of a detector component and related resistor network, schematically representing a position-sensitive detector arrangement.

Noise in the random fluctuation of the preamplifier output voltage when there is not stimulus. It is generated by imperfections in the preamplifier input device, thermal movement of charge carriers in the resistors and the bulk of the detector and inperfections in the crystal structure of the detector. Looking to FIG. 10, an equivalent noise model circuit for solid state detector components is revealed. Note that the model reveals a detector leakage current, $i_D$, which is assumed to be formed of individual electrons and holes crossing the depletion layer of the detector. Such electron hole pairs are thermally generated in the depletion layer. Resistive elements which are in parallel with the system input capacitance, $C_{IN}$, generate thermal noise which is integrated by this capacitance and appears at the preamplifier input as a step function. The system input capacitance is the parallel combination of stray capacitance at the preamplifier input and the feedback capacitor of the preamplifier. Those resistive components which contribute to this noise term are the high voltage bias resistor, the preamplifier feedback resistor and the detector bulk resistance. For a charge dividing resistive strip network, a portion of the dividing resistance, $R_D$, is in parallel with the detector capacitance. Since $R_D$ is less than one hundred kilo-ohms, it represents a significant noise source. The thermal noise from resistors in series with the detector capacitance appears as a delta function to the preamplifiers. For spectroscopy systems, this resistance is minimized and the noise source is neglected. The noise developed by the preamplifier input stage is modeled using a resistor, $R_{eq}$. Finally, a noise term which is not shown in FIg. 10 is "flicker" noise caused by structural changes and surface effects in the conduction material of the noted preamplifier input stage. This noise aspect generally is considered to be insignificant.

Since the noise sources discussed above have a uniform power spectral density, bandwidth limiting filtering or pulse shaping generally is considered appropriate for maximizing the signal-to-noise ratio of the system. As suggested earlier, the fundamental noise sources are classifiable as two types, parallel noise representing the charge due to the electron flow which is integrated by the input circuit capacitance, and series noise representing the charge due to the electron flow which is not integrated by input capacitance. These noise sources are considered to be mutually related in terms of filtering to the extent that as efforts are made to diminish one, the other increases. the high frequency component noise generally is considered a series type while low frequency noise is considered of the parallel variety. As has been detailed in the publications given above, the use of Gaussian and the Gaussian-trapezoidal noise filtering circuits has been found to optimize the energy and spatial resolution values of the camera system.

Figure 2:
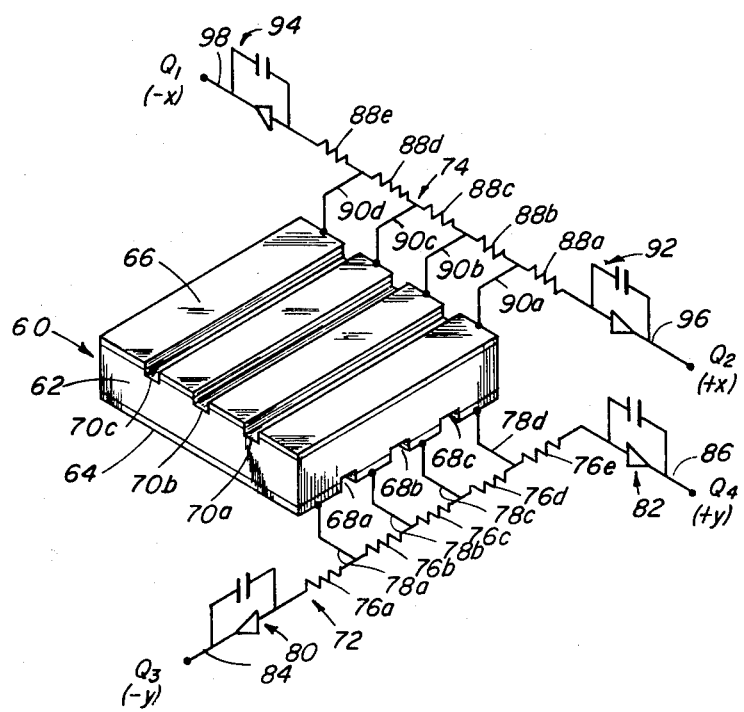
FIG. 2 is a pictorial representation of a solid state orthogonal strip high purity germanium detector component incorporating a charge splitting resistor network in combination with preamplification electronics.

Turning now to FIG. 11, a circuit model of the detector component 60 and the resistor networks of FIG. 2 is portrayed. The discrete nature of the detector system and the method of readout is revealed in the figure with the discrete capacitors forming an n x n array. Each row and column is defined by the charge measured at the end of the resistor strings. The electron-hole pairs which are formed when a gamma ray interacts with the detector are collected on opposite surfaces. A charge enters the resistive network and flows to terminal A or B (C or D) in relation to the resistance between its entry point and the virtual earth terminal of each preamplifier (FIG. 2). The intersection of the column and row defines the diode position in which the gammma ray energy was deposited. Note in the figure, that individual capacitances are represented which are exemplary on the inherent capacitance of the detector itself. When considered in conjunction with the resistor networks, as revealed in the figure, it may be noted that a particular time constant or interval is required for any impinging charge to be represented by a charge flow to the output taps of the resistor chains. Accordingly, the system must provide an adequate time interval or time constant, $\tau_D$, for this charge flow to avoid error in information collection. In effect, it may be assumed that the detector and each of the resistor strings of the noted impedance networks respond as a diffusive line, and the peaking time of the preamplifier output pulses will vary as a function of the position of interaction, $x_O$, of an incident gamma ray. The voltage output of each preamplifier (FIG. 2) due to the instantaneous transfer of charge $Q_O$ at position $x_O$ is:

$$V(0,x,t) = \frac{Q_o}{C_f}\left[1 - \frac{x_o}{L} - \sum_{m=1}^{\alpha} \frac{2}{m\pi} \sin\left(\frac{m\pi x_o}{L}\right) \exp\left[\frac{-m^2\pi^2 t}{\tau_D}\right]\right], \tag{8}$$

$$V(L,x_o,t) = \frac{Q_o}{C_f}\left[\frac{x_o}{L} + \sum_{m=1}^{\alpha} \frac{2}{m\pi} \cos(m\pi)\sin\left(\frac{m\pi x_o}{L}\right) \exp\left[\frac{-m^2\pi^2 t}{\tau_D}\right]\right], \tag{9}$$

where $C_f$ is the feedback capacitance of a preamplifier in farads, L is a givenn linear dimension of the detector, $\tau_D$ is the time constant of the detector (i.e. $\tau_D = 2R_D C_D$), $x_o$ defines the position of interaction and m is a summation variable.

Examination of equation (8) and (9) show that for a time $$t \geq \frac{\tau_D}{2}, \tag{10}$$

i.e., an output generation time equivalent to one half of the time constant of the detector, the value of $V(0,x_o,t)$ is within 1% of its final value for all $x_o/L < 0.95$ and $V(L,x_o,t)$ is within 1% of its final value for all $x_o/L < 0.05$. Stated otherwise, the error generated from ballistic deficit type characteristics of the system, as it relates to the energy of one preamplifier readout diminishes to a value of 1% within a period of one half the time constant, $\tau_D$ of the detector.

By subtracting the output of the one preamplifier of a network, i.e. at the $x = L$ position from the corresponding amplifier output at the $x = 0$ position, i.e.

$$V(0,x_o,t) - V(L,x_o,t) = \tag{11}$$

$$\frac{Q_o}{C_f}\left[1 - \frac{2x_o}{L} - \sum_{m=1}^{\infty} \frac{2}{m\pi} \sin\left(\frac{m\pi x_o}{L}\right)(1 + \cos m\pi) \exp\left(\frac{-m^2\pi^2 t}{\tau_D}\right)\right],$$

the following important observations may be observed. Equation (11) shows that as the spatial location of information impingement alters from 0 to L, the resulting voltage readout moves from a positive unit value to a negative unit value. Stated otherwise the output signal derived from the above signal treatment subtractive approach ranges from $+ Q_o/C_f$ at $x_o=0$, to $-Q_o/C_f$ at $x_o = L$, making the signal twice that of earlier suggested one preamplifier collection technique. Further, it may be observed that the odd numbered series terms vanish, thereby reducing the position signal peaking time. The value of equation (11) is within 1% of its final value for all values $x_o/L \leq 0.45$ and $x/L \geq 0.55$ after a time:

$$t \geq \frac{\tau_D}{8} \tag{12}$$

Accordingly, it may be observed that through the utilization of a dual preamplifier subtractive or "antisymmetric" method of signal analysis, the necessary time constant related signal treatment within the spatial channel is diminished by a factor of 4.

Turning now to the conditions obtaining within the energy channel of the system, the energy channel is derived by summing the output of each preamplifier to obtain the voltage pulse:

$$V(0,x_o,t) + V(L,x_o,t) = \frac{Q_o}{C_f}\left[1 - \sum_{m=1}^{\infty}\frac{2}{m\pi}\sin\left(\frac{m\pi x_o}{L}\right)(1 - \cos m\pi)\exp\left(\frac{-m^2\pi^2 t}{\tau_D}\right)\right] \quad (13)$$

Note again, that the peaking time of the pulse is position dependent. At $x_o/L = 0.5$, the maximum peaking time occurs and the pulse is within 1% f its final value at $t=\tau D/2$. Accordingly, it may be observed that ballistic deficit or charge collection type considerations within the energy channel will required a charge collection period, for practical purposes, equivalent to one half of the time constant of the detector.

Now considering noise phenomena, as earlier discussed in combination with ballistic deficit considerations, as derived immediately hereinabove, dominant spatial noise, which is parallel noise, may be expressed as follows:

$$N_{qS1} = \frac{1}{q}\left(\frac{4kT_D a_p \tau_o}{R_D}\right)^{\frac{1}{2}} \quad (14)$$

where $N_{qS1}$ is the equivalent noise charge in number of electrons for one preamplifier spatial measurements, $R_D$ is the total resistance of the resistive chain, $T_D$ is the temperature of the detector and chain, $a_p$ is a weighting factor of the filter, $q$ is the magnitude of the charge on an electron, and $k$ is Boltzmans constant.

In the expressions given above, i.e. equations 8 through 14, the term $R_D$ is intended as the value representing the average of the total resistance of each resistive network. For the exaggerated exemplary detector component shown in FIG. 2, the term $R_D$ represents one-half the sum of the resistance values of networks 72 and 74. Note from equation (14) that the noise is proportional to the square root of the temperature as well as the weighting factor and the time constant of the system. As disclosed earlier, this time constant is limited by the ballistic deficit conditions of the system. Note further that the noise is inversely proportional to total reisitance of one chain or resistor network. Therefore, it is desirable for system efficiency to minimize the temperature under which it operates as well as the weighting factor and time constant and to elevate the resistance value to the extent practical. Equation (14) is for one preamplifier readout. Reconfiguring the equation to represent a subtractive or antisymmetric arrangement, the following expression obtains:

$$N_{qSAS} = \frac{2}{q}\left(\frac{4kT_D}{R_D} a_p\tau_o\right)^{\frac{1}{2}} \quad (15)$$

From this equation, note that a subtractive arrangement permits the ballistic deficit dictated time constant to reduce by a factor of 4, while the value of noise increases by a factor of 2 for that same time constant, However, since a reduced time constant (factor of 4) is involved in a subtractive arrangement, the noise value, otherwise increased by a factor of 2, remains the same and the signal-to-noise ratio is increased by a factor of 2. Recall the earlier discussion, above, that the unit signal value runs from a positive unit to a negative unit within a subtractive system. The value $R_D$ is difficult to increase inasmuch as a concomitant reduction in energy resolution generally is witnessed for such alteration. Temperature drop can be achieved practically, and the weighting factor, $a_p$, can be altered to a more or less ideal value by appropriate selection of filtering systems. It has analytically been determined that a 43.4 percent improvement in spatial resolution is realized if antisymmetric summation, i.e. subtractive summation, is used as opposed to the utilization, for instance, of one preamplifier for spatial measurement.

Looking additionally to the "ballistic deficit" phenomenon, for thin detectors, i.e. about five mm in thickness, the detector charge collection time is small and does not affect circuitry treating a detected signal. For thick detectors, however, i.e. having a thickness in the range of about 2 cm, the bulk charge collection times varies from approximately 100 to 200 nanoseconds. Since this collection time is approximately the same as the collection time of the charge dividing network, its contribution to ballistic deficit problems must be considered. For such systems, the optimum filtering arrangement consists of a time invariant pre-filter followed by a gated integrator circuit. Such filters generally are referred to as gated-integrators or trapezoidal filters. The filter preferred for the purpose is a Gaussian trapezoidal filter which consists of a time invariant Gaussian filter followed by a gated integrator circuit. Such arrangement is revealed in more detail in the disclosure to follow. For a detailed discourse concerning the utilization of antisymmmetric summation as well as the utilization of trapezoidal filtering within the spatial channel of the system, reference is made to the following unpublished work:

XXII. Hatch, K. F., "Semiconductor Gamma Camera," Ph. D. Dissertation, Massachusetts Institute of Technology, Cambridge, Massachusetts, February, 1972.

The equivalent noise charge in number of electrons for Gaussian trapezoidal spatial measurements may be represented by the following expression:

$$N_{qSGT} = \frac{2}{q}\left(4kT_D a_p T_I \frac{1.79}{R_D}\right)^{\frac{1}{2}} \quad (16)$$

where $a_p$ is the parallel noise weighting function value for Gaussian trapezoidal systems and $T_I$ is the integration time. Analysis of the foregoing shows that an excellent improvement in spatial resolution is obtained by using antisymmetric Gaussian trapezoidal filtering. This improvement is realized because the effects of "ballistic deficit" are greatly reduced.

The corresponding equivalent noise charge in number of electrons for the energy channel of the system may be expressed by the following formulation:

$$N_{qES1} = \frac{1}{q}\left(2qi_D a_p\tau_o + 4kT_D \frac{R_D C_D^2 a_s}{6\tau_o}\right)^{\frac{1}{2}} \quad (17)$$

An important aspect of the above energy channel and spatial channel analyses has been observed. In this regard, it may be recalled that opposed relationships stem from a consideration of parallel vs. series noise phenomena. For instance, it has been described that energy noise is considered serial in nature whereas spatial noise is considered to be parallel in nature. The energy noise equation, as shown at (17) above, represents a straight summation of two preamplifier outputs and the initial parallel noise factor presented within the brackets thereof is of dismissable magnitude. When compared with the spatial noise equation (16) above, it may be observed that two separate time constant values, $\tau_o$, $\tau_e$, respectively, for spatial resolution and energy resolution may be incorporated within the circuitry treating the output of the system detector. For instance, the energy resolution filtering of the system requires a relatively extended time constant, whereas corresponding spatial filtering requires a relatively short one for highest signal to noise ratio considerations. Inasmuch as the outputs of the filtering media reach the output displays of the camera or imaging system simultaneously, any multiple pulse errors introduced into the longer time constant energy filter individually will be integrated to achieve a peak value above a predesignated window function of the energy channel (block 54, FIG. 1). Accordingly, false information generated from pulse pile-up-phenomena and the like may be rejected without recourse to more involved discrimination circuitry. Such a desired system circuit arrangement will be revealed in the description of the control system to follow. While this description is made in conjunction with the singular detector component embodiment of FIG. 2, the theory of its operation will be seen to carry forward into the corresponding operation of a scaled-up control operative in conjunction with a multicomponent detector array.

Figure 12:
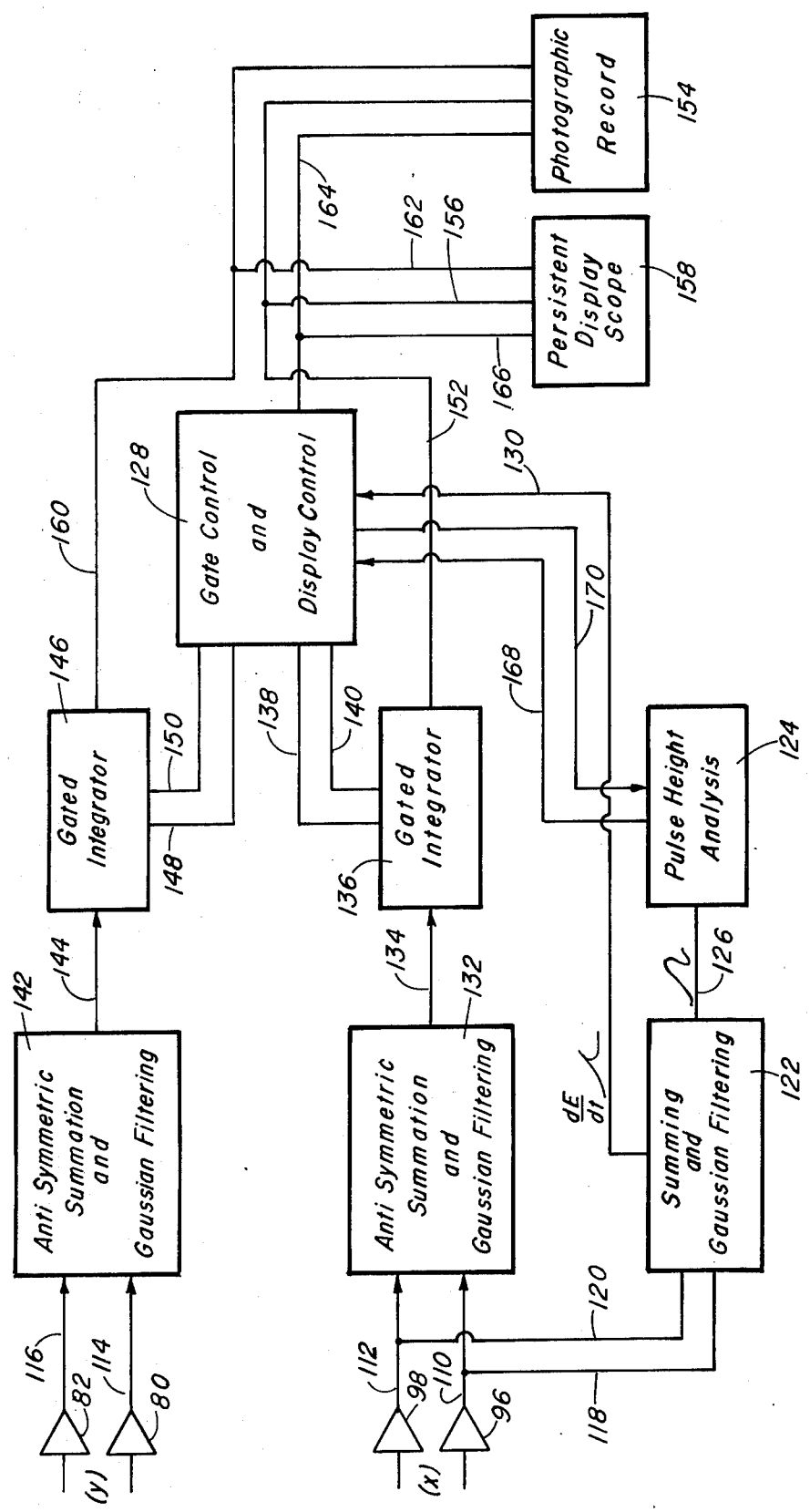
FIG. 12 is a block schematic diagram of a gamma camera control system configured as it is related to a single detector component output.

Referring now to FIG. 12, a block schematic representation of a control system is presented for receiving spatial coordinate outputs of the detector. In the figure, preamplification stages 96, 98 and 80, 82 are reproduced and the outputs thereof, respectively, are revealed at lines 110–116. Arbitrarily designating, for instance, preamplifiers 96 and 98 as deriving energy information along an x-axis, the outputs thereof at 110 and 112 are coupled, respectively, through lines 118 and 120 to the input of a Summing and Gaussian Filtering function 122. As discussed in detail above, function 122 operates under a relatively extended time constant, $\tau_e$. One output from function 122 is directed to a pulse height analysis function 124 from along line 126. The outer output of function 122 is directed to a Gate Control and Display Control function 128 from along line 130. This is an energy derivative pulse, as identified at line 130, and provides a start pulse input to function 128. Output lines 110 and 112 also provide the spatial channel input to Antisymmetric Summation and Gaussian Filtering function 132. From function 132, a subtractive filtered signal is directed along line 134, to a Gated Integrator 136 operating under an integrating period corresponding with time constant $\tau_o$. Control into the gated integrator, for instance, establishing the time constant value, $\tau_o$, emanates from gate control function 128 through line 138. Additionally, a reset control is provided to the integrator from line 140.

Similar to the x-axis spatial channel inputs, the y-axis spatial channel inputs deriving through lines 114 and 116 are introduced into an Antisymmetric Summation and Gaussian Filtering function shown at block 142. The output from block 142, as is present at line 144, is introduced to a Gated Integrator function 146, structured identically to Gated Integrator function 136. Time constant $\tau_o$ control over integrator 146 is asserted from gate control function 128 through line 148, while reset control is asserted from line 150. The output from the x-axis Gated Integrator Function 136 is presented along line 152 to a Photographic Record readout 154 and through lines 152 and 156 to a Persistent Display Scope 158 which may be utilized for purposes of patient positioning and other information desired by the operator. Similarly, the y-axis spatial channel information derived from Gated Integrator function 146 is presented along line 160 to Photographic Record output 154 and through lines 160 and 162 to Persistent Display Scope readout 158. Readout control to Photographic Record 154 and Persistent Display Scope function 158 is derived from Gate Control and Display Control function 128 through lines 164 and 166. The control asserted thereby is one wherein outputs 154 and 158 are not actuated or are blanked until control function 128 receives an input display signal from Pulse Height Analysis function 124 through line 168. Interrogation of function 124 is provided from control 128 through line 170. Inasmuch as a relatively extended time constant, $\tau_e$, is utilized at Summing function 122, any pulse pile-up phenomena will be integrated to derive a peak pulse level beyond the upper window limitations of the channel analyzer operating within function 124. Accordingly, error otherwise introduced into the system from the spatial channels is blanked upon the assertion of an interrogation request from line 170 and a responding blanking type signal or no response signal from function 124 through line 168.

Figure 13:
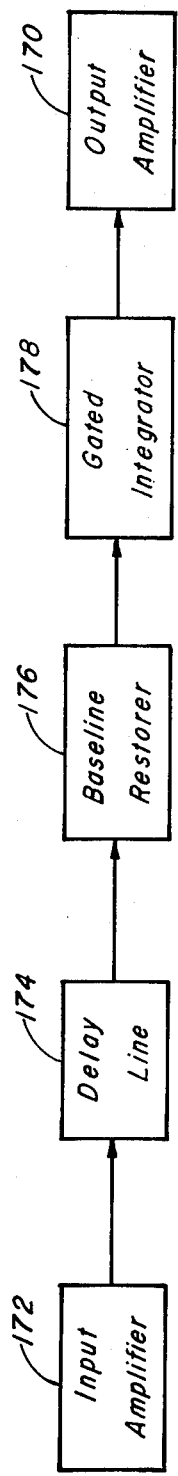
FIG. 13 is a schematic block diagram of a gated integrator configuration which may be utilized with the instant invention.

Looking now to FIG. 13, a block schematic diagram is provided showing the basic components of the Gated Integrator and associated functions depicted generally at blocks 136 and 146 in FIG. 12. Note that the circuit includes an input amplifier 172 which feeds, in turn, into a delay line 174. Delay line 174 is utilized to insure that the integrator gates are open before any spatial informational pulse arrives thereat. The circuit further includes a base line restorer, as at 176, which operates in cooperation with gated integrator 178. The output of integrator 178 is directed to an output amplifier 180, the output from which is directed along lines 152 or 160, as shown in FIG. 12, depending upon the particular orthogonal sense of the incoming signal.

Figure 14:
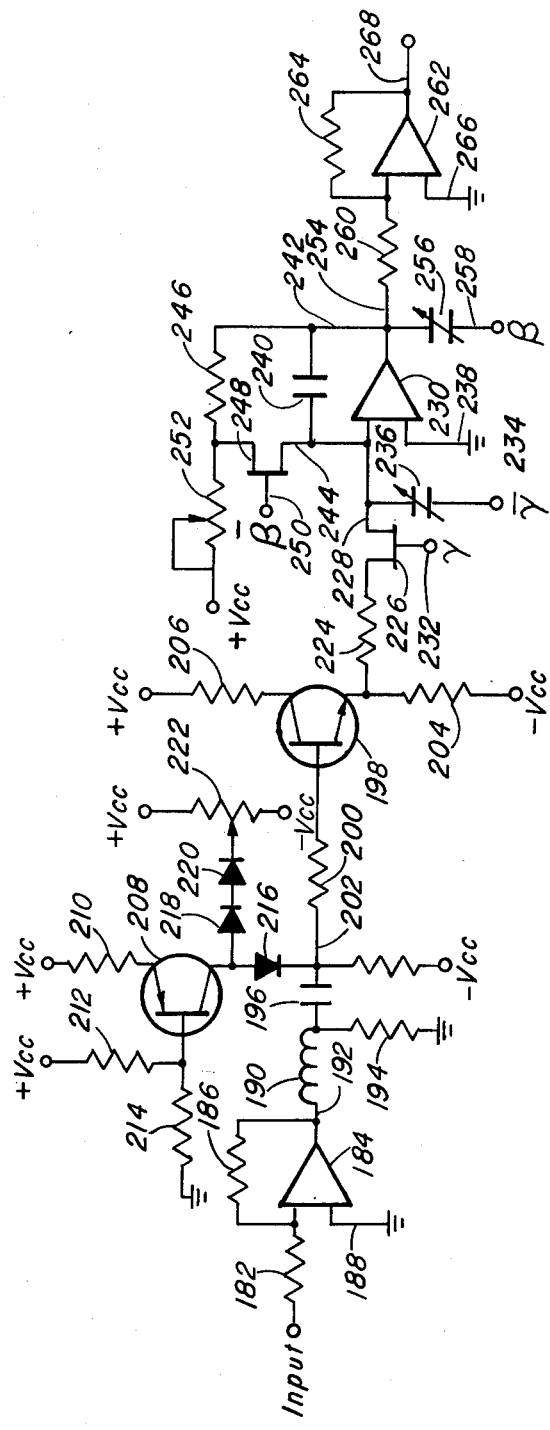
FIG. 14 is a schematic circuit representation of the configuration described in connection with FIG. 13.

A corresponding and more detailed schematic representation of the circuit is revealed in FIG. 14. Referring to that figure, either of the coordinate spatial inputs as developed at lines 144 or 134 (FIG. 12) is asserted through an input resistor 182 to an amplification stage 184. Stage 184, corresponding to amplifier block 172 in FIG. 13, includes a feedback line incorporating feedback resistor 186, as well as a ground reference input at line 188. Delay line 174 is shown represented at 190 receiving an input from output 192 of amplifier 184. A resistor 194 is coupled between delay line 190 and ground, while the output thereof is AC coupled through capacitor 196 to the input of a base line restorer function. The base line restorer is of a Robinson type as is generally described, for instance, in the following publication:

XXIII. Robinson, L.B., "Relation of Baseline Shift in Pulse Amplitude Measurements", Rev. Sci. Inst., 32, 1961, p. 1057.

Essentially, the restorer function is provided for the purpose of assuring a net zero charge value at the gated integrator input prior to the reception of any input signal. Further, the restorer defines the maximum charge that can be placed on the coupling capacitor 196. In the absence of the restoring function, the gated integrator would integrate areas below the baseline as well as under the Gaussian shaped spatial signal. For carrying out its assigned functions, the restorer includes an emitter-follower stage at NPN transistor 198, the base of which is coupled through resistor 200 and line 202 to one side of capacitor 196. The emitter of transistor 198 is coupled through a resistor 204 to $-V_{cc}$ potential, while its collector is coupled through a resistor 206 to $+V_{cc}$. The restorer function additionally includes a current supply network operating such that, upon the occurrence of spurious elevations of current, accommodation is made to control the quiescent point at the emitter-follower stage 198. Note that this current supply includes a PNP transistor 208, the emitter and base of which, respectively, are coupled through resistors 210 and 212 to $+V_{cc}$. This base, additionally, is coupled to ground through a resistor 214. The collector of transistor 208 is coupled through diode 216 to line 202 and through diodes of 218 and 220 to a variable resistor 222, the termini of which are connected between the positive and negative sides of the supply voltage.

The output of the base line restorer function is coupled through resistor 224 to one terminal, for instance the source, of a field effect transistor (FET) 226 representing the input of the gated integrator function, while the opposite electrode of the transistor is coupled to line 228. Line 228, in turn, is directed to one side of an integrating amplifier 230. The gate input to FET 226 is present at line 232 and is shown as selectively receiving a signal designated $\gamma$ from the control function 128 (FIG. 12). Also influencing line 228 is a network including line 234 and variable capacitor 236 which is coupled to receive an input designated $\bar{\gamma}$. The opposite input to amplification stage 230 is coupled to ground through line 238. Amplification stage 230 performs an integrating function by virtue of its feedback connection with an integrating capacitor 240 coupled between lines 242 and 244. A shunting resistor 246 is coupled between lines 242 and 244 in parallel with capacitor 240 and is selectively activated by a reset gate present as field effect transistor (FET) 248, the source and drain terminals of which are connected in switch defining fashion within line 244 and the gate input to which at line 250 is configured to selectively receive a reset signal identified as, $\bar{\beta}$, from Gate Control function 128 (FIG. 12). A variable resistor 252 is connected between the positive supply voltage and the interconnection of resistor 246 with FET 248. The output of amplification stage 230 is present at line 254 and is coupled through a variable capacitor 256 and line input 258 for selectively receiving a signal input identified as, $\beta$.

The output at line 254 of the gated integrator is directed through resistor 260 to the input of a unity gain inverting amplifier 262 which includes a feedback line incorporating resistor 264 and is connected with ground reference at line 266. The output of the amplifier, at line 268, is that represented in FIG. 12 either at line 152 or line 160 and is directed to the readout components of the camera system. As will be apparent in the discussion to follow, gate control over integrator 178 is derived by the noted signal inputs into lines 232, 234 and 250 and 258.

Figure 15:
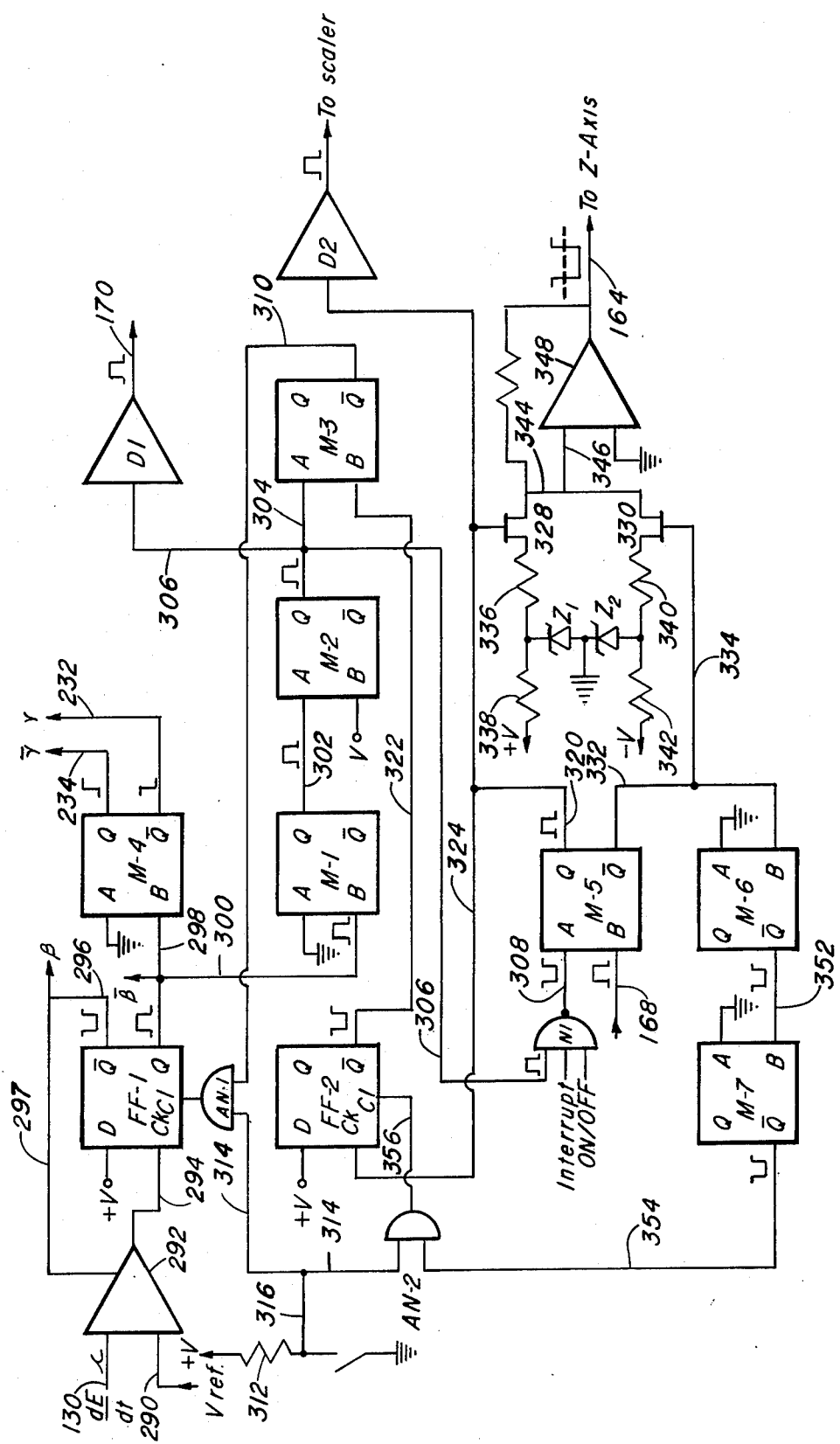
FIG. 15 is a schematic representation of the logic components of a control arrangement which may be utilized with the system of the invention.
Figure 16:
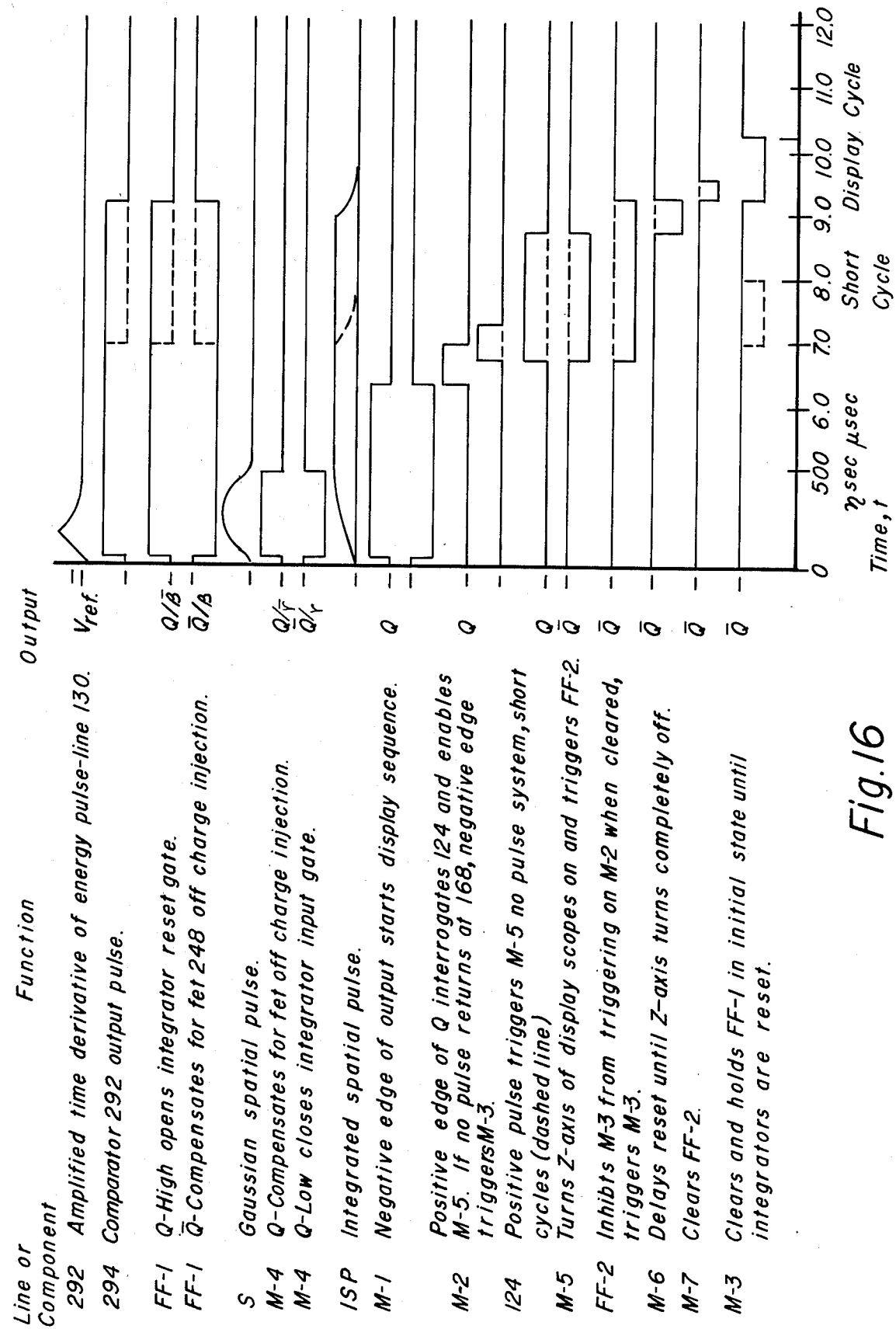
FIG. 16 is a circuit timing diagram corresponding with the schematic representation shown in FIG. 15.

Looking to FIGS. 15 and 16, the control circuit represented in FIG. 12 at 128 is disclosed in more detail in combination with a timing sequence diagram. At time, $t$ = 0, as shown in the timing diagram of FIG. 16, the system is prepared to process an incoming set of signals or pulses. The time derivative of the energy pulse or signal $dE/dt$ is directed along line 130 to a comparator 292. When its value exceeds a reference voltage representing the lower level of the window level established by evaluation or Pulse Height Analysis function 124 (FIG. 12) it serves as a start or to actuate the control system. The voltage reference against which the derivative of the energy pulse or signal is compared is inserted from line 290 to the comparator. These predetermined, preliminary signal level conditions being met, comparator 292 provides a positive going output pulse at line 294 which is introduced to a dual, D-type flip-flop FF-1. Conventionally, the D form of flip-flop incorporates an actuating (clock) input signal terminal, $Ck$, along with a signal input terminal, D. The flip-flop output signal Q becomes 1 at the time of a 0-to-1 change at the clock terminal. In conventional manner, the $\bar{Q}$ output of the flip-flop represents the inverse of the Q output. The D flip-flop also is characterized in incorporating a clear feature designated at "C1" in the diagram. To further facilitate the description of the circuit, Boolean designation is utilized to represent input or output values. For instance, a "low" signal is considered to be one having a potential essentially at ground and is typically represented by a logical "zero." Conversely, a "high" signal is considered positive and may be depicted by a logical "one."

Returning to FIGS. 15 and 16, with the presence of a positive going pulse at line 294, flip-flop FF-1 is clocked such that its Q output at line 298 assumes a high value and its $\bar{Q}$ output at line 296 assumes a low value. Note that the Q output of flip-flop FF-1 is identified as $\bar{\beta}$ and is introduced to the reset gate of each integrator, as shown in FIGS. 12–14. With the opening, for instance, of reset gate transistor FET 250, the shunt about timing capacitor 240 is removed to enable the integrating amplifier. Similarly, the $\bar{Q}$ output of flip-flop FF-1 assumes a low status and, by connection through line 296, couples the $\beta$ signal input to the gated integrator as at line 258 in FIG. 14. This $\beta$ signal output of the flip-flop FF-1 is used to compensate for charge injection into the feedback capacitor caused by the capacitance coupling between the gate and drain electrodes of FET 248.

The Q output of flip-flop FF-1 additionally is presented through line 298 to the B input terminal of a monostable multivibrator M-4, and, through line 300, to the B input terminal of monostable multivibrator M-1. Accordingly, these multivibrators are triggered, the Q output of multivibrator M-4 being programmed for closing each integrator input gate for a time slightly greater than the base width of the Gaussian shaped spatial pulses. In this regard, note that the $\bar{Q}$ output, as is represented at line 232 of the multivibrator M-4, carries a $\gamma$ signal which is introduced into the input gate of FET 226 (FIG. 14). Simultaneously, an inverted $\bar{\gamma}$ input is provided along line 234 to variable capacitor 236 to provide compensation for off charge injection. The gated integrator then commences an integrating mode of performance, the time over which operation is controlled by multivibrator M-4. It may be observed that multivibrator M-4 retains this output state in correspondence with a spatial time constant determined interval, $t_s$, as is more clearly portrayed in FIG. 16. Note in that figure, the representation of a Gaussian spatial pulse, S, corresponding with the activation of the integrator function.

As noted above, the Q output of flip-flop FF-1 also is introduced to the B input terminal of monostable multivibrators M-1. With the presence of the forward edge of this signal at line 300, the Q output of the latter alters from a low to a high value and retains such value over an interval, $t_e$, selected for delaying the start of the display sequence until the energy pulse has been analyzed at pulse height analysis function 124 as shown in FIG. 12. Note that this interval, $t_e$, always will be greater than the integrating interval, $t_s$. The Q output of multivibrators M-1 is coupled through line 302 to the A input of monostable multivibrator M-2. On the occurrence of the negative edge of the pulse of the Q output of multivibrator M-1, multivibrator M-2 is triggered and the resultant Q output transition thereof is directed along lines 304 and 306 to driver circuit D1. The output at line 170 of driver D1 serves as the earlier described interrogation pulse directed to the pulse height analysis function 124 described in connection with FIG. 12. Note additionally, that line 306 extends to one input of a NAND gate N1. Accordingly, the signal from line 306 is inverted and introduced through line 308 to the A input terminal of monostable multivibrator M-5. This input serves to enable the latter to permit the carrying out of a full control cycle. During typical display operation of the camera system, the "interrupted" and "on/-off" inputs to NAND gate N-1 are high at the option of the operator. By converting either or both to a low value, multivibrator M-5 is inhibited to, in turn, inhibit the displays as referred to earlier in FIG. 12 at 154 and 158.

The remaining components of the circuit function on the basis of whether an interrogating signal issued from line 170 to Pulse Height Analysis Function 124 (FIG. 12) has been responded to, along line 168, to indicate a pass or no pass condition of signal energy level. If function 124 does not respond to the interrogating pulse from line 170, thus indicating that the peak value of the energy pulse did not fall within the window setting of the evaluation function, multivibrator M-5 receives no signal input at terminal b thereof. Additionally, upon the occurrence of the negative edge of the Q output signal of multivibrator M-2, multivibrator M-3 is triggered from line 304 such that its $\overline{Q}$ output at line 310 asserts a clearing signal through AND gate AN1 to the clear input terminal, C1, of flip-flop FF-1. The output thereof, as reflected at the multivibrator M-4, causes the integrator to be reset. With this operation, the system is short cycled, and the through-put rate thereof advantageously is increased. Note, that the opposite input at line 314 of AND gate AN1 is normally high by virtue of its connection through line 316 and resistor 312 to a positive voltage source.

Assuming that multivibrators M-5 has been enabled from the line 308, A, input thereto and that a positive response has been received from Pulse Height Analysis function 124 and line 168 at the B terminal input thereto, the multivibrator will react by developing a positive output pulse at its Q terminal and line 320, while a pulse of opposite sense is developed at its $\overline{Q}$ output along line 332. The Q output signal at line 320 is directed to line 324 whereupon it addresses the clock input, Ck, of D flip-flop FF-2. In consequence, the Q output of flip-flop FF-2, at line 322, converts to a low value which is asserted at the B input of multivibrator M-3 to inhibit the output thereof. The short cycle feature thereby is inhibited. This signal at line 324 may also be utilized for clocking a scaler or count recording apparatus through a driver circuit D2.

The outputs of multivibrators M-5 also are utilized to switch a Z-axis driving circuit from a negative to positive voltage, thereby turning on the display functions represented in FIG. 12 at 154 and 158. In this regard, note that line 334, carrying the Q output signal of multivibrator M-5, is connected to the gate electrode of a field effect transistor (FET) 328. By corresponding connection, the $\overline{Q}$ output of multivibrator M-5 is asserted along lines 332 and 334 to the gate input of field effect transistor (FET) 330. Note that the drain-to-source channel of FET 328 is connected through resistors 336 and 338 to a positive voltage source, while the corresponding source-to-drain channels of FET 330 are coupled through resistors 340 and 342 to a negative voltage supply. The respective opposite sides of FET's 328 and 330 are connected through line 344 and line 346 to one input of a Z-Axis amplifier 348 and are biased such that, under conditions wherein monostable multivibrator M-5, is not clocked, the output of amplifier 348 is retained at a negative value. Upon the clocking of multivibrator M-5, however, FET 330, in effect, closes while FET 328 opens, to cause the output of amplifier 348 to change from a negative to positive value, thereby permitting the activation of display and record functions 154 and 158 (FIG. 12).

Zener diodes as at $Z_1$ and $Z_2$ are present in the input network to Z-axis amplifier 348 for the conventional purpose of voltage regulation, the diodes being commonly coupled to ground at their respective anodes. Additionally, the respective cathodes of the diodes $Z_1$ and $Z_2$ are coupled at the common connections of resistors 336 and 338, 340 and 342.

Looking further to the outputs of multivibrator M-5 as they respond to an energy evaluation input at line 168, the positive edge of the output signal at $\overline{Q}$ thereof also activates a multivibrator M-6 in consequence of the connection of line 332 with the B terminal thereof. Multivibrator M-6 serves to provide a delay function assuring an adequate interval for turning off the electron beams of display scopes and the like. The $\overline{Q}$ output of multivibrator M-6 is coupled through line 352 to the B terminal input of another monostable multivibrator M-7. The positive going edge of the $\overline{Q}$ output signal of multivibrator M-6 triggers multivibrator M-7 to provide a corresponding pulse signal at its $\overline{Q}$ output at line 354. Line 354 is coupled through AND gate AN2, the output of which is coupled through line 356 to the clear terminal, C1, of flip-flop FF-2. The opposite input to AND gate AN-2 is operator preselected and is asserted from line 314. With the presence of a clearing input to flip-flop FF-2, the $\overline{Q}$ output thereof at line 322 returns to a high status which, in turn, is imposed at the B input of multivibrator M-3 which, in turn, functions to clear flip-flop FF-1 by virtue of the connection therewith of its $\overline{Q}$ output at line 310 through AND gate AN-1. With the clearing of flip-flop FF-1, the gated integrator is discharged or reset through the $\overline{\beta}$ input signal at line 250, described earlier in connection with FIG. 14.

With the noted return of monostable multivibrator M-3 to its standby state, the control system is fully reset and ready to process another set of information signals. If the output of comparator 292 is high at this time, the system will not process such incoming information. This lock-out feature prevents the partial integration of spatial pulses too narrowly spaced in insertion time. Note that comparator 292 is coupled to receive the $\beta$ signal output from the $\overline{Q}$ terminal of flip-flop FF-1 through lines 296 and 297. This input signal is utilized by the comparator as a block to any enabling of the system to respond to incoming signals until such time as a full cycle of evaluation has terminated. FIG. 16 reveals the time-based correspondence between the output of comparator 292 and the $\overline{Q}$ output or β signal of flip-flop FF-1. In the absence of such β signal input from line 297, error would be introduced into the system, for instance, by virtue of the generation of start signals at line 294, integrator timing is disrupted to invalidate an ongoing signal processing procedure. As may be evidenced from FIG. 16, the β signal input from line 297 (flip-flop FF-1, $\overline{Q}$ terminal) serves to inhibit comparator 292 until the reset point of a given signal processing cycle.

As noted earlier, any display of spatial pulses which overlap is prevented because, for the optimized filtering system, the base width of the spatial Gaussian pulse is less than the peaking time of the energy Gaussian pulse or interval of energy analysis. Because of this, should two or more gamma arrays photoelectrically interact with the detector and their total energy be absorbed in a time less than the rise-time of the filtered energy pulse, the resulting energy pulse peak value would not fall within the window defined at pulse height analysis function 124. As a consequence, the control system would carry out a short cycle function as revealed in the timing diagram of FIG. 16 by a dashed line alteration of the curves.

Examination of the dashed curves of FIG. 16 reveals that, upon interrogation of Pulse Height Analysis 124, should no response signal be received therefrom within the interrogation interval defined by multivibrator M-2, the negative going edge of the output thereof causes multivibrator M-3 to carry out a reset function, thereby inhibiting the carrying out of the remainder of the signal processing cycle.

As noted earlier, it is important that the detector function of the gamma camera be capable of accepting photon information from as broad a spatial region as possible. Inasmuch as the size of detector crystals inherently is limited by the techniques of their fabrication, it becomes necessary to conjoin a plurality of such detector components in some manner wherein a broader region of radiation may be witnessed and imaged.

One preferred technique for associating the discrete detector components provides for their mutual operational interconnection in subgroupings of predetermined numbers, for instance, 4, which subgroupings then are coupled with the control system of the camera. An array of detector components having a requisite camera entrance area acceptance geometry then is formed preferably of a symmetric compilation of component subgroupings. One practical size for the detector array comprises four subgroupings each of which is formed of four detector components. With such an array, the control system advantageously may operate by observing the performance of the subgroupings as they are represented in quadrature. Another aspect to be considered in "scaling-up" the camera system for clinical utility resides in the earlier-discussed feature permitting their accepting and properly imaging information derived from two discrete photon energy levels. Accordingly, the scaled-up gamma camera would incorporate a control system accommodating both of these desired features. In the discourse to follow, the general signal treatment described hereinabove in connection with FIGS. 12-16 remains substantially the same with an appropriate multiplication of functions where necessary to accommodate for the greater number of generated signal inputs from the detector groupings.

Figure 17:
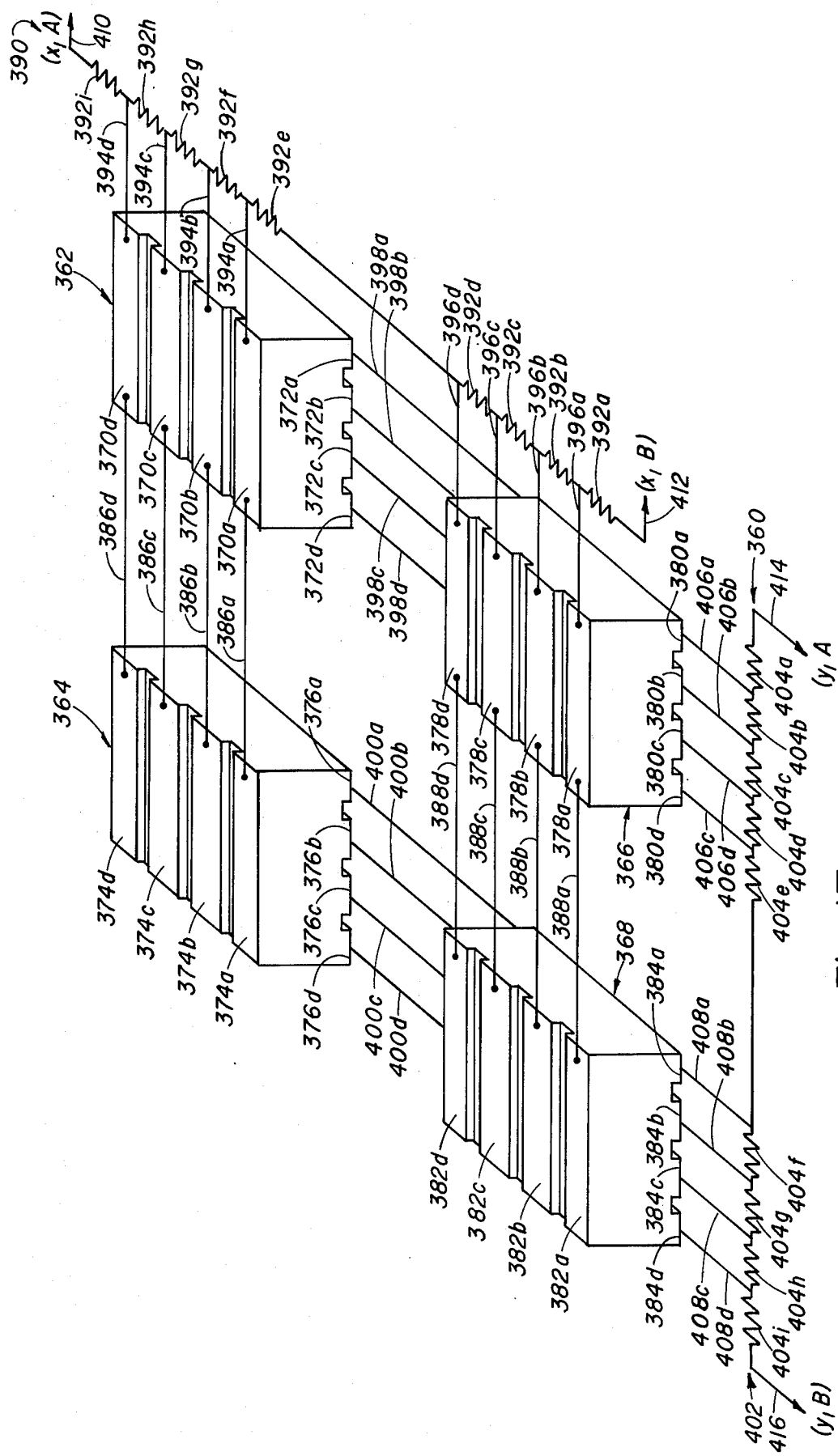
FIG. 17 is a pictorial and schematic representation of an array of detector components showing the interconnections thereof to form a composite detector or region thereof as may be utilized with the system of the invention.

Turning to FIG. 17, a composite detector, formed as an array of discrete detector components, is revealed generally at 360. This sub-grouping of four detector components, as identified at 362, 364, 366, and 368, may, for instance, be combined with three additional subgroupings to form a full detector array comprising four subgroupings incorporating a total of 16 detector components. Of course, a greater or smaller number of detector components may be combined to form an array of desired dimension. In the interest of clarity, only one such quadrant designated subarray, as at 360, is described in conjunction with a control system. Detectors 362-366 are dimensioned having mutually equivalent areas designated for the acceptance of impinging gamma radiation. Such equivalency serves to achieve accurate ultimate image readout from the camera system. The detector components 362-366 are of the earlier-described orthogonal strip array variety, each strip thereof being defined by grooves. Note in this regard, that detector component 362 is formed having strips 370a-370d located at its upwardly disposed surface and defined by grooves cut intermediate adjoining ones of these said strips. The opposite face of the detector component 362, similarly, is formed having strips 372a-372d defined by intermediately disposed grooves arranged orthogonally with respect to the grooves at the upper surface. Detector component 364 is identically fashioned, having strips 374a-374d at its upwardly disposed surface, each being defined by intermediately disposed grooves; the lower surface of the detector being formed having orthogonally disposed strips 376a-376d defined by intermediately disposed grooves. The corresponding strip arrays of detector component 366 are shown to comprise identically disposed strip groupings as at 378a-378d and 380a-380d. Similarly, detector component 368 is shown to be formed of identically structured mutually orthogonally disposed strip arrays 382a-382d and 384a-384d.

Components 362-368 are illustrated expanded from one another for purposes of illustration only, it being understood that in an operational embodiment these components are internested together in as practical a manner as possible. To achieve an informational spatial and energy output from the discrete detector components, the strip arrays each are mutually associated along common coordinate directions. This association is carried out between components 362 and 364 by leads 386a-386d, coupling respective strips 374a-374d of component 364 with strips 370a-370d of component 362. In similar, parallel coordinate fashion, leads 388a-388d are provided for connecting respective strips 382a-382d of component 368 with strips 378a-378d of component 366.

The outputs of the thus mutually coupled strip arrays of the upwardly disposed faces of the detector components are coupled with an impedance network, represented generally at 390. Network 390 is configured serially interconnected discrete resistors 392a-392i. Interconnection between respective strips 370a-370d and points intermediate resistors 392e-392i is provided by leads 394a-394d, while corresponding interconnection between strips 378a-378d with the intermediate connections of resistors 392a–392d is provided by leads 396a–396d.

In similar fashion, the arrayed strips 372a–372d at the lower surface of component 362 are coupled with respect to strips 380a–380d of component 366 by leads 398a–398d. Similarly, strips 376a–376d at the lower face of component 364 are respectively coupled with corresponding strips 384a–384d of component 368 by leads 400a–400d. The thus associated strip arrays of the lower faces of the detector components are connected with a second impedance network, identified generally at 402, in similar fashion as the orthogonally disposed upward surfaces. Note, for instance, that strips 380a–380d of the lower surface of component 366 are connected to intermediate respective discrete resistors 404a–404e of network 402 by leads 406a–406d. Similarly, strips 384a–384d of the lower surface of component 368 are connected with respective discrete resistors 404f–404i of network 402 through leads 408a–408d. Thus interconnected, the four discrete detector components provide spatial coordinate parameter outputs; i.e. x-designated coordinate outputs at lines 410 and 412, which are identified thereat as ($x_1$A) and ($x_1$B). In like manner, the spatial coordinate parameter outputs of the lower surfaces of the detector components are present at lines 414 and 416 and are y-designated, being labeled in the drawing, respectively, as ($y_1$A) and ($y_1$B).

Figure 18:
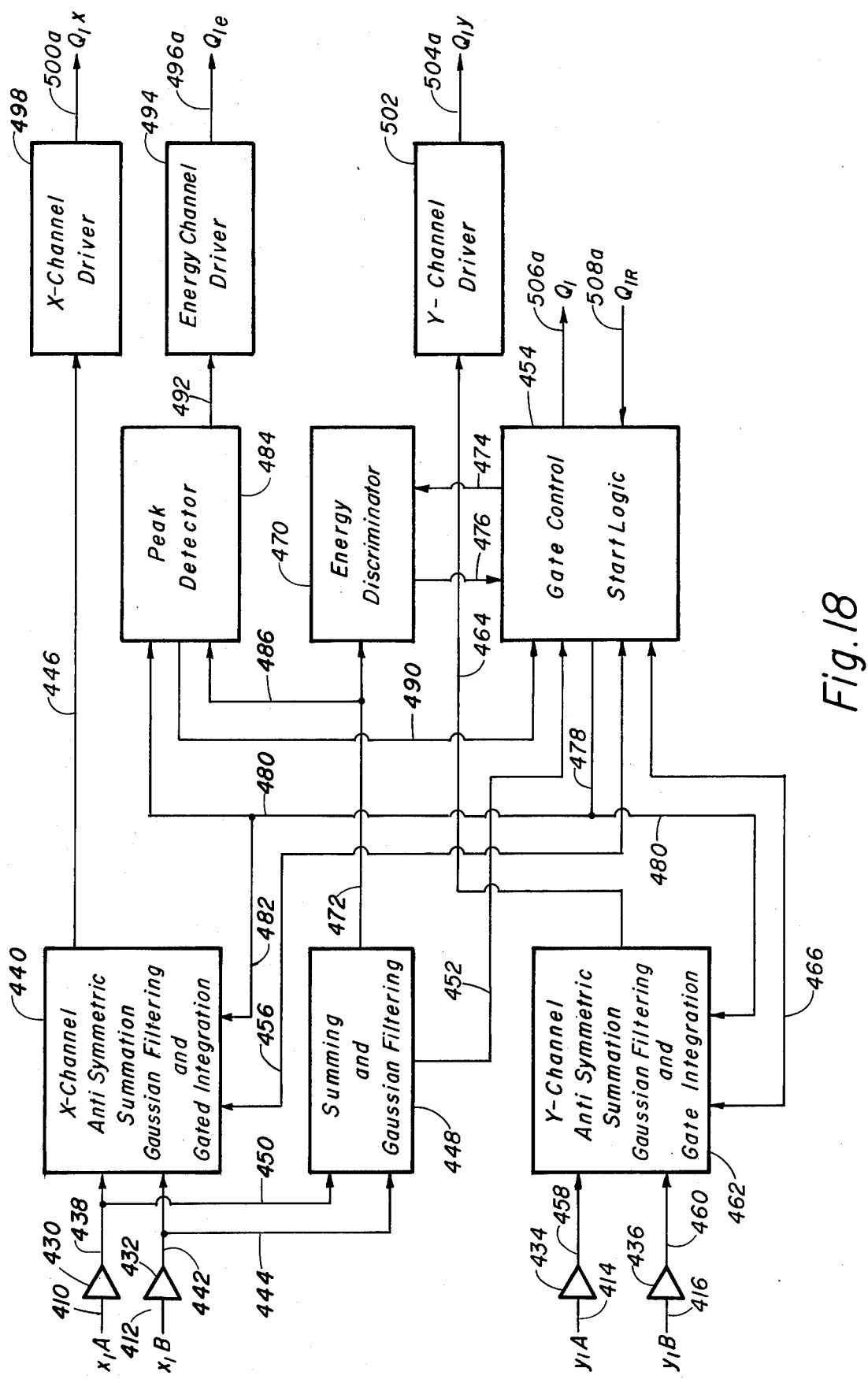
FIG. 18 is a block schematic representation of a control system utilized to receive and treat the outputs of the detector array configuration of FIG. 17.

FIG. 18 reveals a first output treating arrangement, present as one set of filtering and control electronics which operates in conjunction with the quadrant detector array of FIG. 17. In that figure, spatial coordinate parameter outputs, or x-designated coordinate outputs ($x_1$A), ($x_1$B) and ($y_1$A), ($y_1$B) are represented, respectively, at lines 410–416. These outputs, as at lines 410–416, are shown arranged to address discrete preamplification stages respectively revealed at 430–436. In this regard, note that the output at line 438 of preamplification stage 430 is introduced to an x-Channel Antisymmetric Summation Gaussian Filtering and Gated Integrater function, shown at 440, while the corresponding input from preamplification stage 432 is directed along line 442 to that same function. The summing and filtering functions at 440 operate on the x-coordinate outputs introduced thereto in the same fashion as described above in connection with the FIGS. 12–16. For instance, the inputs from the x-spatial coordinate outputs are subtractively summed and, following appropriate filtering and pulse shaping as by the noted series of integrations and the like, an output from block 440 is provided as x-designated coordinate channel signals at line 446.

The outputs of x-channel amplification stages 430 and 432 also are directed, respectively, through lines 450 and 444 to Summing and Gaussian Filtering function 448. As described in conjunction with FIGS. 12–16, function 448 includes an initial stage deriving the time derivative of the summed energy signal provided from lines 444 and 450 and submits such derivative signal from along line 452, to a Gate Control and Start Logic function, identified at block 454. Such signal evidencing a predetermined requisite level to provide a preliminary assurance of valid spatial information, the start logic function of block 454 responds to provide gate control over Filtering and Summation Function 440, as through line 456.

The corresponding y-coordinate outputs of amplification stages 434 and 436, respectively, are coupled through lines 458 and 460 to a y-Channel Antisymmetric Summation and Gaussian Filtering function 462. Configured in similar fashion as function 440, the signals introduced to function 462 are subtractively summed, appropriately filtered, and pulse-shaped by a series of integrations to provide a y-designated coordinate channel signal at line 464. Control over the gated integration function, as well as filtering at block 462 is provided from gate control and start logic block 454 as through line 466. In fashion similar to that described in connection with FIGS. 12–16, the control system further includes an Energy Discriminator, revealed at block 470, which receives the summed energy signal output at line 472 from Summing and Gaussian Filtering function 448. As before, Energy Discriminator 470 provides a pulseheight analysis of the energy signal to evolve an accurate evaluation thereof as to the presence of absence of solid image information. Upon interrogation thereof through line 474 from gate control function 454, and response thereto at line 476, the signal treating cycle is permitted to continue. However, as described earlier, where the pertinent energy signals fail to meet the window criteria of Energy Discriminator 470, gate control 454 will effect a resetting of the summing functions, as from lines 478, 480, and 482 to carry out the earlier-described short-cycle operation, thereby permitting the system to more rapidly and efficiently process a next incoming spatial signal. It may be noted that Energy Discriminator function 470 may operate effectively within the system even though more than one photon energy level of information is asserted. Recall that it is desirable to accomodate the system to the utilization of more than one radiopharmaceutical, each such radiolabeled substance having a different gamma ray energy characteristic. Because the germanium detector system of the invention enjoys a considerably improved resolution characteristic, the discriminator 470 is capable of performing its assigned function in a practical fashion at this stage of the control system. In this regard, the germanium detector exhibits a capability of from 3 to 4 keV resolution range as opposed to a generally observed range of about 15 keV achieved with more conventional scintillation type cameras. Accordingly, Energy Discriminator 470 readily may be adjusted to pass those energy signals representing the lower acceptable level of the lower photon energy designated radiopharmaceutical.

In accordance with the invention, the filtering and control electronics for a given quadrant also incorporates a Peak Detector function represented at 484. Detector 484 is coupled through lines 472 and 486 to receive the energy signal generated from summing function 448. The detector 484 serves to hold the peak value of this signal, thereby providing an analogue storage function to accomodate for variations in signal treatment times as are represented for instance, between Antisymmetric Summation functions 440, 462 and the energy additive Summing function at 448. Detector 484 is associated in time control fashion with gate control 454 through line 490 and may be reset therefrom through lines 478 and 480. The peak value output of detector 484 is presented along line 492 to an Energy Channel Driver 494 for ultimate presentment to quadrant processing control circuitry described later herein. Note that the energy channel signal present at line 496a is designated, $Q_{1e}$.

With the occurence of an appropriate acceptance of the validity of a spatial signal at Energy Discriminator 470, the x-designated coordinate channel or spatial signal at output line 446 is delivered to an x-Channel Driver 498, the output of which is present in line 500a. Note that this channel signal is designated $Q_{1x}$. Similarly, the y-designated channel signal, having been treated at function 462 and admitted to the system by the Energy Discriminator 470 and gate control functions, is presented along line 464 to a y-Channel Driver 502, the output of which is present at line 504a and identified as, $Q_{1y}$.

The information now delivered from each quadrant of the overall imaged region now, for purposes of convenience, is designated by the noted labels: $Q_{1x}$, $Q_{1y}$ and $Q_{1e}$. In the immediate discussion to follow, the composite detector array is assumed to be functioning in quadrature and, thereby, developing corresponding signals from four distinct multi-component quadrants. These quadrants are represented by a "Q" with the noted subscripts altered by the values 1-4. Gate control 454 also provides a clocking or data acceptance signal sequencing input to the control system at line 506a the signal from which is designated, $Q_1$, and is arranged to receive a reset signal, designated, $Q_{1r}$, as at line 508a. The latter signal is selectively derived from the quadrant processing control system to be described in conjunction with FIG. 19.

Figure 19:
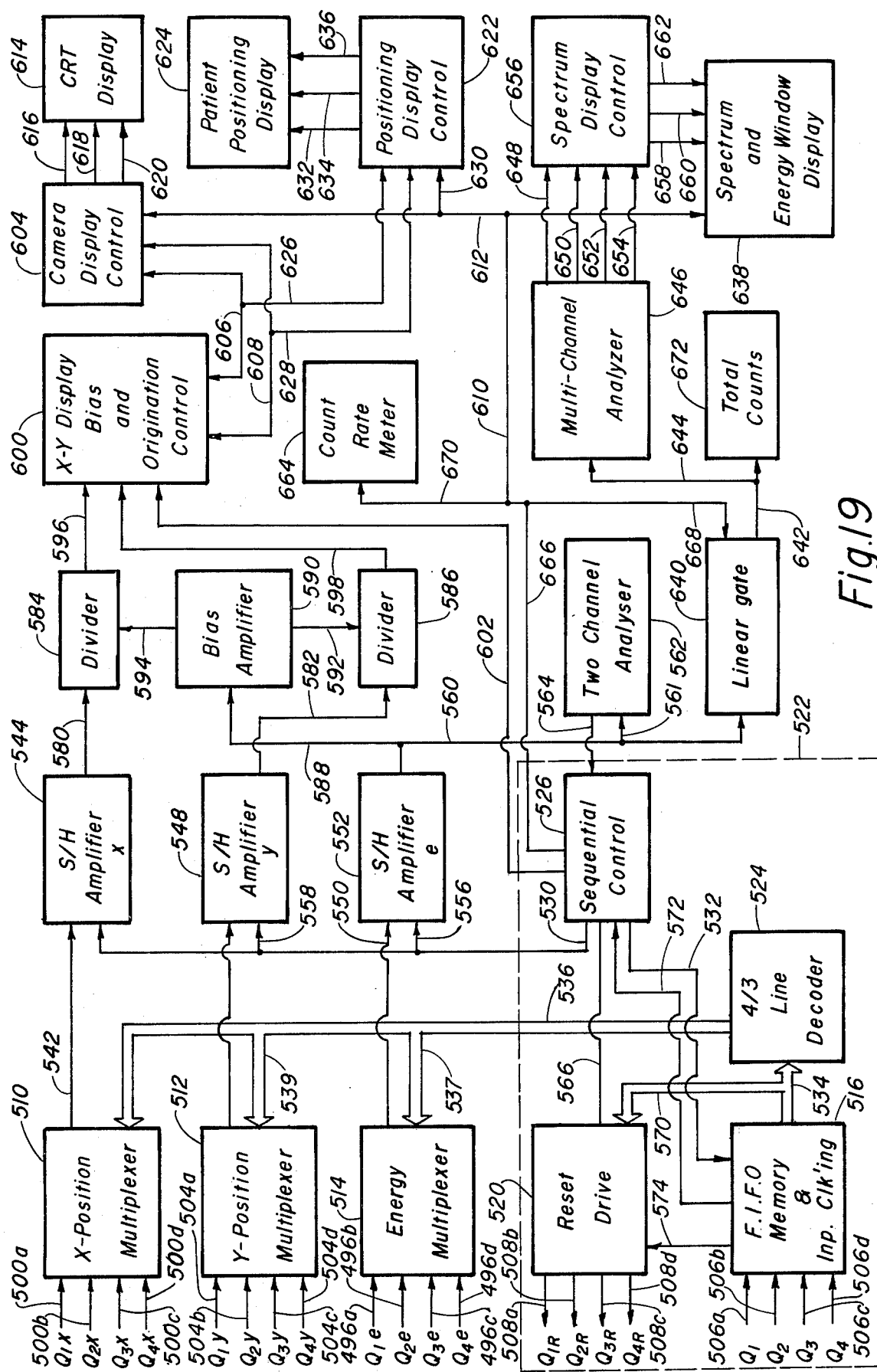
FIG. 19 is a block schematic diagram of an embodiment of the control system of the invention as it is utilized for treating the signals developed by the control arrangement of FIG. 18.

Turning to that figure, the noted processing arrangement is revealed in block schematic fashion and is shown to include three multiplexing input networks, an x-Position Multiplexer 510, a y-Position Multiplexer 512, and an Energy Multiplexer 514. The inputs to multiplexers 510-514 derive from each of the four quadrant circuits and, as an example of the designations utilized in the instant figure, for the quadrant circuit described in connection with FIG. 18, such inputs are represented and labeled at lines 500a, 504a, 496a, 506a, and 508a. Correspondingly, the inputs from the three remaining circuits to each of the multiplexers are represented and labeled, respectively, at 500b-d, 504b-d, 496b-d. Additionally, the outputs from Gate Control and Start logic functions, as described, for example, at 454 in FIG. 18 are represented, respectively at 506a-506d as leading to F.I.F.O. Memory 516, while the input to functions as at 454 in FIG. 18 are represented as output lines 508a-508d extending from Reset Drive function 520. Note, additionally, that the quadrant signals leading to the quadrant processing control arrangement of FIG. 19 are identified by an ascending numeration suffix for each input function, i.e. the inputs for x-Position Multiplexer 510 are identified as $Q_{1x}$-$Q_{4x}$, the inputs to y-Position Multiplexer 512 are identified as $Q_{1y}$-$Q_{4y}$, the inputs to Energy Multiplexer 514 are identified as $Q_{1e}$-$Q_{4e}$, the data acceptance signal inputs to F.I.F.O. Memory are identified as $Q_1$-$Q_4$ and the outputs of Reset Drive function 520 are identified as $Q_{1R}$-$Q_{4R}$.

In conventional fashion, multiplexers 510-514 perform a switching type function wherein the channel signals addressed thereto are selected and forwarded into the system upon appropriate control logic commands present as coded actuating signals. These multiplexers are regulated from a quadrant interface control function, represented within a dashed line boundary 522. Function 522, in addition to incorporating the F.I.F.O. Memory and input clocking 516 and Reset drive function 520, includes a 4-to-3 Line Decoder 524 and a Sequential Control function 526. F.I.F.O. (first-in, first-out) Memory and Input Clocking 516 is conventionally formed incorporating somewhat independent input and output stages or networks. It serves within the system as a de-randomizer which receives and collects or records the randomly generated data acceptance signals, which are presented at lines 506a-506d. These quadrant labeled signals are received and serialized at the input clocking stage of F.I.F.O. Memory and Input Clocking 516 following which, an appropriate signaling or clocking pulse is sent to the Sequential Control 526, through line 572 which tells the sequential control that quadrant information is available. In consort the quadrant identification signal is passed through output 534 and 570 to the 4-to-3 line decoder 524 and the reset drive 520. The resultant coded actuating signals are presented to the multiplexers along grouped lines 536, 537, and 539 which, in turn, signal the appropriate gates within respective multiplexers 510, 512, and 514 to pass the retained spatial and energy signals to a Sample and Hold Amplified function (S/H). In this regard, note that the output of x-Position Multiplexer 510 is provided along line 542 to a Sample and Hold Amplifier 544, while the corresponding y-Position Multiplexer 512 output is presented along line 546 to Sample and Hold Amplifier 548. Similarly, the output of Energy Multiplexer 514 is provided along line 550 to Sample and Hold Amplifier 552. Sample and Hold Amplifiers 544, 548 and 552 are utilized within the circuit as an analog storage medium so that the aforementioned quadrant circuits can be reset for processing incoming signals. Line 530 extends through line 556 to Sample and Hold Amplifier 552; through line 558 to Sample and Hold Amplifier 548; and directly to Sample and Hold Amplifier 544. A command from Sequential Control 526 emanating from line 530 provides an initial sample command whereupon the multiplexers output signals are sampled by the Sample and Hold Amplifiers. Following a select interval, a hold signal is passed to amplifiers 544-552, following which a next succeeding interval is provided. In consort with the issuance of the hold signal to amplifiers 544-552, a reset command signal is passed by the Sequential Control through line 566 to the Reset Drive circuit, 520. Since the spatial and energy information contained in the quadrant circuit being addressed is now stored in the processing circuit, the appropriate quadrant circuits can be reset through the appropriate reset line $Q_{1R}$-$Q_{4R}$ (lines 508a-508d). In carrying out the latter functions, it may be noted that reset drive function 520 derives the quadrant selective information through lines 570 from the F.I.F.O. Memory 516, at the end of the reset command a clock-out pulse is sent to the F.I.F.O. Memory 516 along line 532 from the Sequential Control unit 526. By doing this the information at the output of F.I.F.O. Memory 516 is clocked out so that the next usable information appears at F.I.F.O. Memory 516 output. The fact that valid information appears at F.I.F.O. Memory 516 output is sent along line 572 to the Sequential Control circuit 526 for current or future use. At the time valid output appears at F.I.F.O. Memory 516 output the 4/3 Line Decoder 524 decodes it for processing by the multiplexer circuits. During the latter interval, the energy signal, now passed to the hold function of amplifier 552, is present at the output thereof at line 560, during which period it further is introduced at line 561 and analysed by a Two-Channel Analyser 562. Analyser 562 provides pulse-height analysis requisite to evaluating the energy levels of the earlier noted two radiopharmaceuticals, for example, which may be utilized within the system. Note that the analysis performed at function 562 is the second within the system, the initial evaluation being carried out in the earlier-described circuitry associated with each quadrant of the detector. Should the energy signal passed to the Two Channel Analyser 562 fail to meet the window criteria for either select photon energy level, an appropriate representation or signal is provided at output line 564 to Sequential Control function 526. If a valid, information present pulse was received from F.I.F.O. Memory and Input Clocking 516 along line 572, then the sample and hold amplifiers 544, 548, and 552 are placed in the sample mode and the process described above repeats itself. If a valid information present pulse was not received, the Sequential Control 526 waits until one is received before the process described above repeats itself. Where more than two photon energy levels are selected for the system, an appropriate multi-channel analyser is substituted at component 562.

An advantageous aspect of the invention resides in the controlled interrelationship between multiplexers 510–514 and corresponding Sample and Hold Amplifiers 544–552. As controlled by sequential control 526, an initial clocking input to multiplexers 510–514 causes a quadrant signal received thereby, in given arrival order, to be clocked to the appropriate ones of Sample and Hold Amplifiers 544, 548, and 552. Following the initial interval described hereinabove, commencing with the noted hold function, the initial treating system may be cleared in anticipation of a next quadrant signal to be processed as described above. This feature advantageously improves the through-put rate of the overall system permitting correspondingly improved imaging performance. With the clearing of the initial treatment or input networks as well as clocking of F.I.F.O. Memory 516, the entrance portion of the quadrant processing circuitry is prepared to accept the next succeeding quantum of information from the quadrant circuits. Upon appropriate command from sequential control 526 following an interval suited to permit the noted two-channel analysis to be carried out at block 562, the x- and y- spatial output signals of Sample and Hold Amplifiers 544 and 548 respectively which are passed along lines 580 and 582 to Divider networks 584 and 586 are stable and proportioned respectively to the x- and y-positions. The latter networks serve the function of normalizing the spatial signals received from lines 580 and 582 with respect to the particular photon energy of the detector interaction which they represent. The corresponding energy signal introduced at this point to the system and analyzed at 562 may be represented as, $Q_E$, while the spatial signal may represented as, $\alpha Q_e$. From the earlier discussion presented herein, the spatial information, $\alpha$, which the system, notwithstanding quadrature data, provides as spatial visual information may be represented by the expression:

$$\alpha = \left(1 - \frac{2x_o}{L}\right), \tag{18}$$

where, $L$, is equivalent detector length and, $x_o$, is the position of interaction of a gamma ray. The spatial information quantity, $\alpha$, also may be derived and expressed by the relationship:

$$\alpha = \left(\frac{\alpha Q_E}{Q_E}\right) \tag{19}$$

Equation (19) reveals the function of Dividers 584 and 586, i.e. by dividing by $Q_E$, the measured energy channel signal, as it represents one or more photon energy levels, the desired spatial signal, $\alpha$, is derived. In carrying out this function, the devisor of the last expression (19) is derived as a signal from Sample and Hold Amplifier 552 through lines 560 and 588. Line 588 is coupled with a Bias Amplifier 590 which provides an appropriate d.c. offset to prevent the presentment of a zero denominator to the divider circuits. The outputs of Bias Amplifier 590 are shown directed along line 592 to Divider 586 and along line 594 to Divider 584. Because of the advantageous high quality resolution of germanium type solid state detectors, the dividing function provided herein is required only for systems intended to utilize radioisotope imaging sources to present more than one photon energy level but can be used with a monoenergetic source.

The thus normalized x- and y- spatial channel signals are directed, respectively, from Dividers 584 and 586 along line 596 and 598 to an x-, y- Display Bias and Orientation Control function, identified at control block 600. At function 600, the signals introduced thereto are weighted in correspondence with the quadrant or coordinate from which they were derived by virtue of a weighting signal input from control 526 as directed thereto through line 602. Control 600 also may include appropriate circuitry providing for an operator selection of the alignment of the x- and y-axes wherein they may be inter-changed for desired clinical analysis purposes. Control 600 is coupled in information exchange relationship for x-channel information with a Camera Display Control 604 through line 606 and, for y-channel communication purposes through line 608 with the same control. Display activations to the Camera Display Control 604 is derived from the output of Sequential Control 526 through lines 666, 610 and 612. In conventional fashion, the spatial data and the display on/off control is coupled to a CRT Display 614 through the three channel input lines extending thereto and identified at 616, 618 and 620.

In similar fashion, a Patient and Positioning Display function is provided by Positioning Display Control circuit 622 operating in conjunction with a positioning display readout, i.e. CRT tube or the like, as represented at block 624. Spatial channel information is directed to Positioning Display Control 622 from lines 626 and 628 which, in turn, are connected with respective lines 606 and 608. A display activating signal is sent to control 622 from Sequential Control 526 through lines 666, 610, 612 and 630. The spatial energy channel intercoupling between control function 622 and its corresponding display readout at 624 are shown represented by lines 632, 634, and 636.

The control system also incorporates a readout identified in FIG. 19 as a Spectrum and Energy Window Display represented at block 638. This readout serves to permit the operator of the system to adjust the window settings of the two-channel analyser 562 to achieve accurate evaluation of the energy level of the particular isotopes utilized for imaging. The informational input of function 638 is derived from the energy related output level of Sample and Hold Amplifier 552, as is present at line 560. To convert this level to a corresponding transitional signal, a Linear Gate 640 is arranged to receive the energy signal at line 560 and transmit a corresponding transitional type signal along lines 642 and 644 to a Multi-channel Analyser 646. The channel outputs of analyzer 646 are presented along lines 648-654 to a spectrum display control 656 which, in turn, provides display control over Spectrum and Energy Window Display 638 by virtue of its connections therewith represented at lines 658-662.

The system also provides a count rate meter 664 which is coupled with the display control signal from Sequential Control 526 through lines 666 and 670. Such a device apprises the operator of the presence of imaging photons at the region of analysis and their reaction rate with the system. Note, additionally, that the output display control of Sequential Control 526 also is directed through line 666 and 670 to Linear Gate 640. The output of Linear Gate 640, at line 642, also is directed to a Total Count function 672, the latter serving to apprise the operator of the quantity of imaging information received at the camera. Other components which might be incorporated within the system, which are not shown in the figure, may include, for instance a total time recorder, apprising the operator of the span or interval of operation of the camera for given clinical analysis as well as an isotope gain control for regulating the Summation and Filtering function described hereinbefore in connection with FIG. 18.

With the final imaging of a given energy signal, at CRT Display 614, sequential control 526 directs a signal along line 530 to the Sample and Hold Amplifiers 544-548 and 552 placing them in the sampling mode. Since, as described above, the information from the next quadrant is presented as each Sample and Hold Amplifier input through lines 542, 546 and 550 an improvement in system throughput rate is realized.

Figure 20:
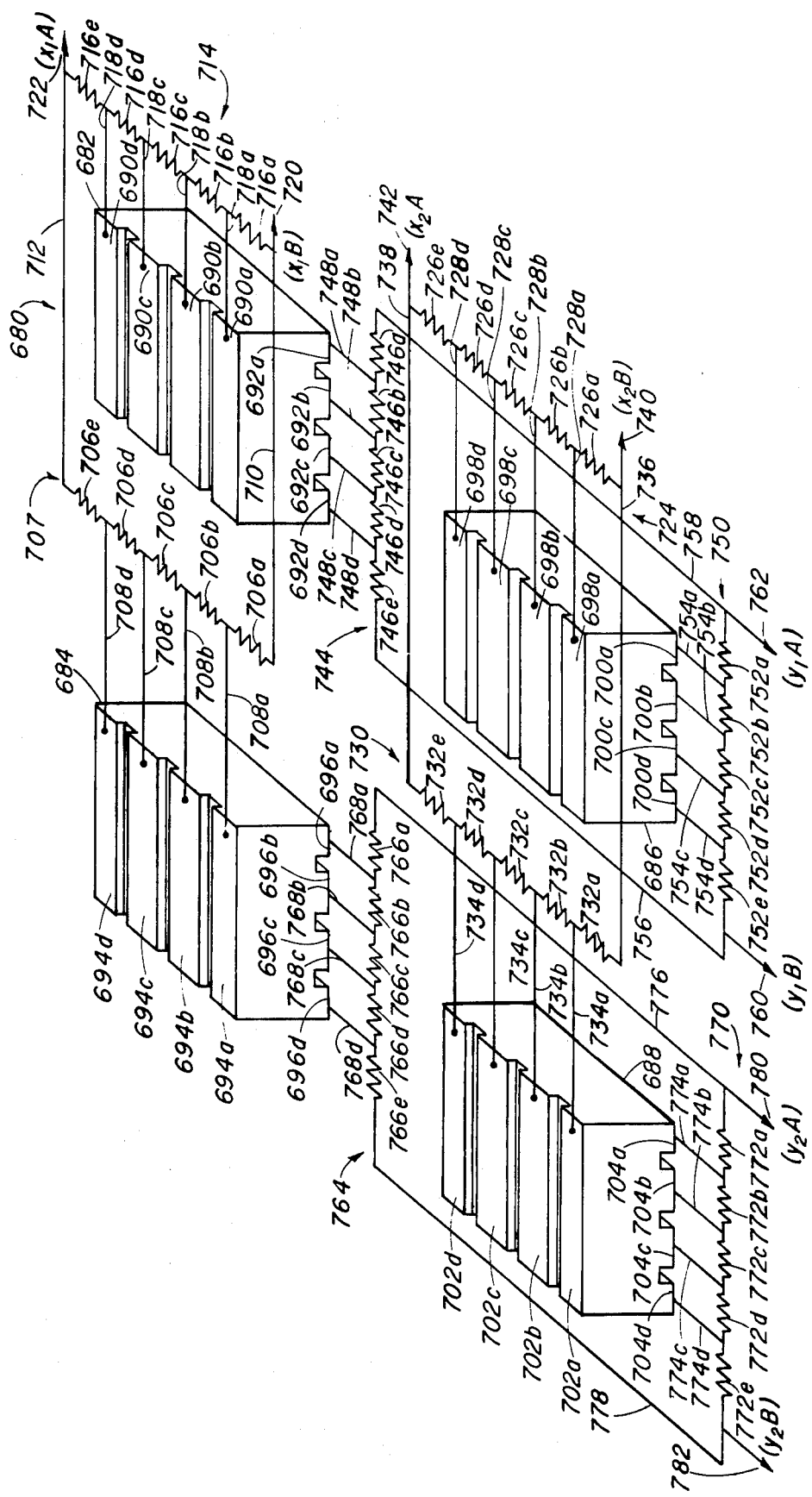
FIG. 20 is a schematic and pictorial representation of another array of detector components, interconnected in accordance with a "row-column" readout geometry.
Figure 21:
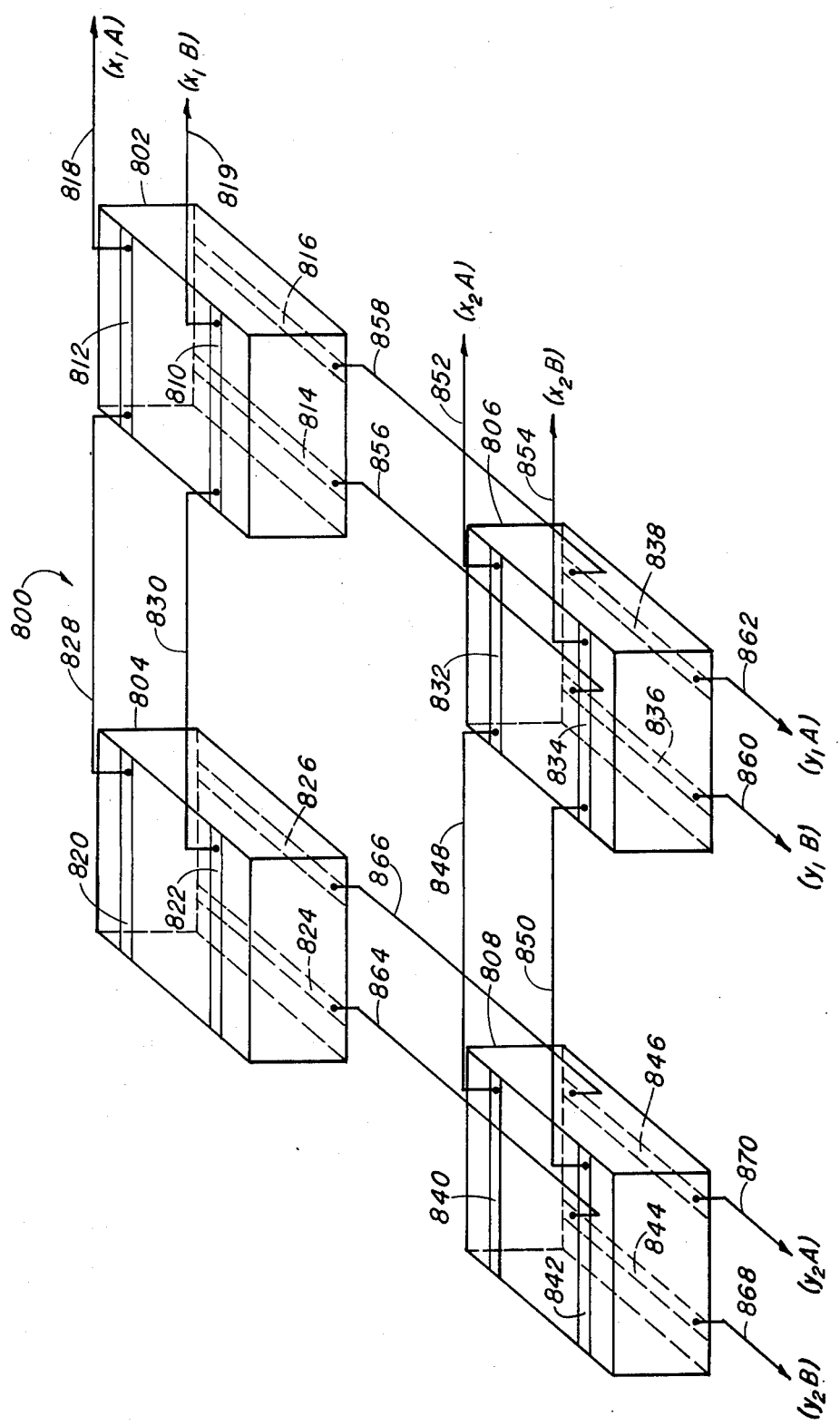
FIG. 21 is a schematic and pictorial representation of another array of detector components, each of which is formed associated with a surface type impedance arraignment, the components being interconnected in the noted "row-column" fashion.
Figure 22:
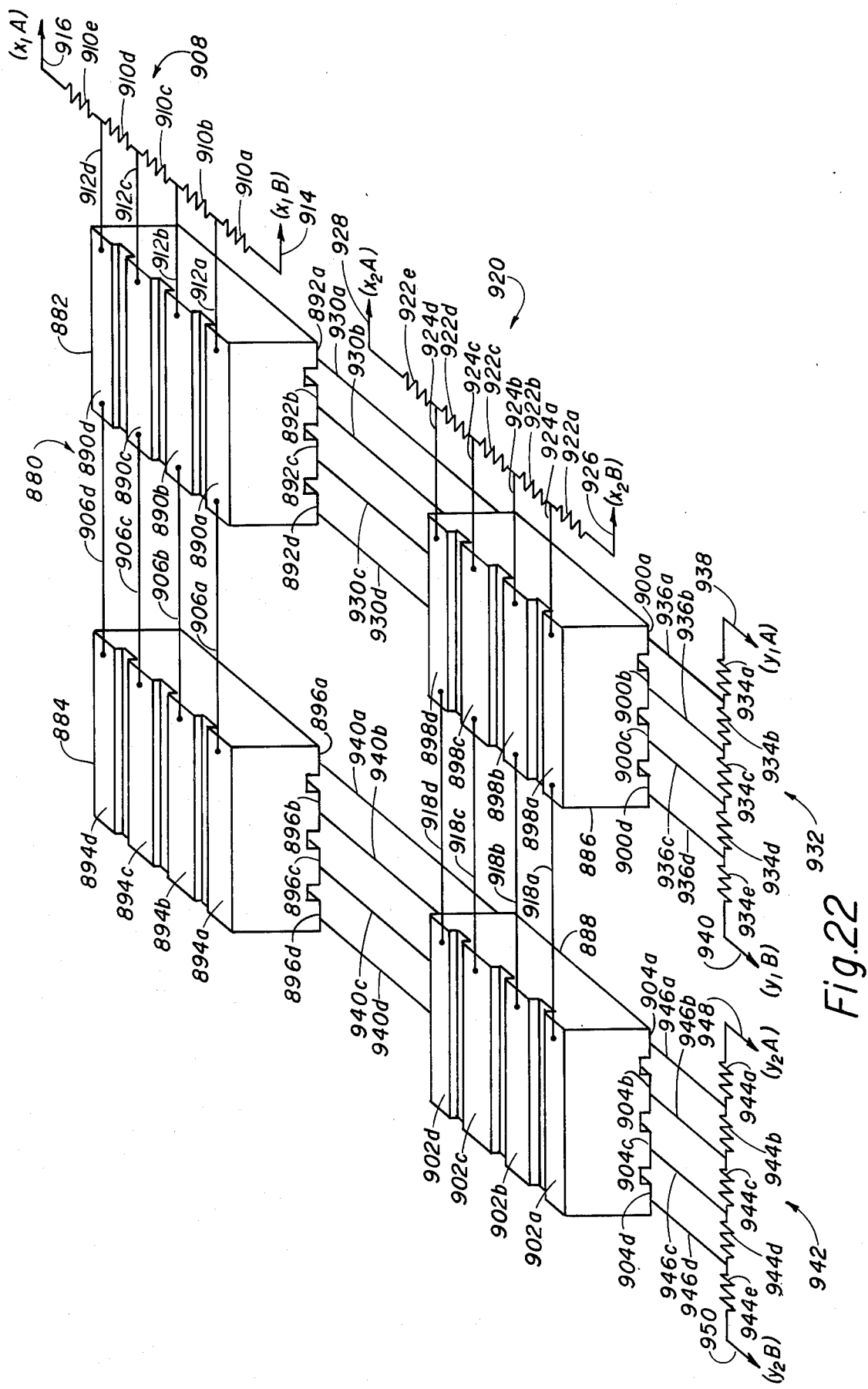
FIG. 22 is a schematic and pictorial representation of another array of detector components interconnected in accordance with the noted "row-column" geometry.

In FIGS. 20-22 as are described hereinafter, another form of composite detector is revealed which provides a "row-column" form of readout of the spatial and energy data within a select grouping, n, of detector components. In each of these embodiments shown, a reduced component linear dimension over which resolution is required is achieved to improve the resolution of the entire system. Two embodiments of this "row-column" arrangement are revealed wherein a larger effective detector area is provided while the earlier described time constant, $\tau_D$, is minimized to improve the response rate of the system to processing interaction generated image signals.

Referring now to FIG. 20, another composite detector formed as an array of discrete detector components is revealed generally at 680. Illustrated in exploded fashion, the detector 680 is comprised of a plurality of detector components, four of which are shown at 682, 684, 686, and 688. Components 682-688 are dimensioned having mutually equivalent areas as are intended for acceptance of impinging radiation. This required equivalency serves to achieve an accurate ultimate image readout from the camera system. In the absence of such equivalency, distortion at such readout, exhibiting a discontinuity of image information, would result. The detector components illustrated are of the earlier-described orthogonal strip array variety, each strip thereof being defined by grooves. Note, in this regard, that detector component 682 is formed having strips 690a-690d located at its upward surface and defined by grooves cut intermediate adjoining ones of the said strips. The opposite face of detector component 682 similarly is formed having strips 692a-692d defined by intermediately disposed grooves arranged orthogonally with respect to the grooves at the upper surface. Detector component 684 is identically fashioned, having strips 694a-694d at its upwardly disposed surface and lower surface, orthogonally disposed strips 96a-96d each strip being defined by intermediately formed grooves. Similarly, detector component 686 is formed having strips 698a-698d at its upward surface defined by intermediately disposed grooves, while its lower surface similarly is formed having strips 700a-700d defined by intermediately disposed grooves arranged orthogonally with respect to the grooves of the upward surface. Detector component 688 may be observed having strips 702a-702d at its upward surface defined by intermediately designated grooves, while its lower surface is formed with strips 704a-704d separated by intermediately disposed grooves arranged orthogonally to the grooves of the upward surface of the component.

Detector components 682-688 as well as similar components in later figures are illustrated expanded from one another for purposes of illustration only, it being understood that in an operational embodiment these components are internested together in as practical a manner as possible. To achieve an informational spatial and energy output from the discrete detector components, which essentially is equivalent to that output which would be realized from a large detector of equivalent size, the strip arrays are functionally associated under a geometry which, as noted above, may be designated "row" and "column" in nature. In this regard, note that an impedance network, shown generally at 707, is associated with the strips 694a-694d of detector component 684. This network incorporates discrete resistors 706a-706e which are tapped at their common junctions by leads 708a-708d extending, respectively, to strips 694a-694d. Thus configured, network 707 closely resembles the impedance networks described herein in connection with FIG. 2. Note however, that output lines 710 and 712 of network 707 extend to and are coupled in parallel circuit relationship with the corresponding output of a similar impedance network, identified generally at 714. Network 714 incorporates discrete resistors 716a-716e which are tapped at their common interconnections by leads 718a-718d. Leads 718a-718d, in turn, respectively extend to strips 690a-690d of detector component 682. Accordingly, the upwardly disposed surfaces of detector components 682 and 684 are identically associated with respective impedance networks 714 and 707, while the latter are interconnected in row fashion and in parallel circuit relationship to extend to principal output terminals, as are depicted generally at 720 and 722. It may be noted, that the information collected at these principal terminals represents one imaging spatial coordinate parameter of a select directional sense i.e. along a designated row.

Looking now to the functional interrelationship of detector components 686 and 688, a similar coordinate parameter direction or row-type informational collection network is revealed. In this regard, note that the impedance network, shown generally at 724, is configured comprising discrete resistors 726a-726e, the points of common interconnection of which are coupled with respective leads 728a-728d. Leads 728a-728d, in turn, respectively, are connected with strips 698a-698d at the upwardly disposed surface of detector component 686.

Likewise, an impedance network, shown generally at 730 incorporating discrete resistors 732a–732e, is associated with detector component 688 by leads 734a–734d extending, respectively, from strips 702a–702d to the points of common interconnection of network discrete resistors 732a–732e. Additionally, the output lines as at 736 and 738 of network 730 are connected in parallel circuit relationship with the output of network 724 to provide row readout termini, respectively, at 740 and 742. Here again, a row-type directional spatial coordinate parameter is provided at the upwardly disposed surface of the composite detector 680.

Looking now to the lower surfaces of the detector components, it may be observed that the orthogonally disposed strips of detector component 682 are associated with an impedance network identified generally at 744. Network 744 incorporates discrete resistors 746a–746e which are coupled from their mutual interconnections by leads 748a–748d, respectively, to strips 692a–692d of detector 682. Similarly, the orthogonally disposed strips of detector component 686 are associated with an impedance network 750. In this regard, network 750 is formed of discrete resistors 752a–752e which, in turn, are coupled, respectively, with strips 700a–700d by leads 754a–754d. The output of impedance network 744 is connected by leads 756 and 758 to the corresponding output of impedance network 750 to provide column directional coordinate parameter outputs, as at 760 and 762, which serve to collect all spatial information of the associated paired surfaces of detectors 682 and 686.

Looking to the lower surface of detector component 684, note that a network, designated generally at 764, incorporating discrete resistors 766a–766e is functionally associated with strips 696a–696d, respectively, by leads 768a–768d.

In similar fashion, an impedance network, designated generally at 770, is associated with the orthogonally disposed strips 704a–704d at the lower surface of detector component 688. Note that the network, incorporating discrete resistors 772a–772e, is functionally associated with the array of strips 704a–704d, respectively, by leads 774a–774d. Networks 764 and 770 are electrically coupled in parallel circuit fashion by collector leads 776 and 778 which extend respectively to principal collection points or termini 780 and 782. Thus interconnected, the lower surfaces of detectors 684 and 688 are coupled in column readout fashion to provide another spatial coordinate parameter of direction parallel with the corresponding lower surface strip array readout arrangement of detector components 682 and 686.

With the row and column readout intercoupling of the detector components as shown in the figure, it may be observed that the capacitance exhibited by all discrete detector components, taken together, remains the same as if only a single detector were operating within a camera. Accordingly, the signal treating circuitry and logic of the camera, advantageously, may be designed to accommodate for the charge collection time constant of a single detector. Connection with the row and column readouts for given spatial coordinate parameters outputs will be seen to be provided by treating circuits which distribute coordinate channel spatial and energy channel signals into analyzing and distributing circuitry. Such circuitry is described in more detail in connection with FIGS. 19 and 23–27. Preamplification stages, as described in connection with FIG. 2, are coupled with each row readout point as at 720 and 722 or 740 and 744, as well as with each column readout, as at 760 and 762 and 780 and 782. Such preamplification stages generally are located within or near the cryogenic environment of the detector itself. The mounting of the contact leads between each of the networks and an associated strip array surface of a detector generally may be carried out by resort to biased contact configurations.

The composite detector arrangement or interrelated detector component mosaic also may be formed utilizing detector structures which incorporate surface disposed resistive layers to achieve spatially proportioned charge readout characteristics. Such a detector composite is revealed generally in FIG. 21 at 800. Referring to that figure, the composite detector, or portion thereof, 800, is shown to comprise four discrete detector components 802–808. The opposed surfaces of the detector components, which are situated generally normally to impinging radiation, are formed having a resistive character. This resistance is provided, for instance, by so lightly doping the n-type surface as to achieve a region of resistive character, while, similarly, so lightly doping the opposite surface with a p-type acceptor as to achieve a surface resistive character thereat. The readout from these resistive surfaces is collected by conductive strips which, for the case of detector component 802, are shown on the upward surface at 810 and 812 and at the lower surface at 814 and 816. Conductive surfaces 810–816 may be deposited upon the detector component 802, for instance, by conventional evaporation techniques utilizing a highly conductive metal such as a noble metal, i.e. gold.

Concerning the techniques for developing the noted resistive regional character within the surfaces of detector components 802–808, mention may be made of the following publications:

XXIV. Owen, R. P., Awcock, M. L., "One and Two Dimensional Position Sensing Semiconductor Detectors," IEEE, Trans. Nucl. Sci., Vol. N.S. - 15, June 1968, Page 290.

XXV. Berninger, W. H., "Pulse Optical and Electron Beam Excitation of Silicon Position Sensitive Detectors", IEEE, Trans. Nucl. Sci., Vol. V.S. 21, Page 374.

With the impingement of radiation upon detector component 802 and resultant development of an interaction therewithin, charge will be collected on the opposed surfaces, as discussed above, and will split proportionally at the impedance define surfaces and collect at the conductive strips 810–816. For the upwardly disposed surface, these charges then are collected along conduit 818, coupled with conductive strip 812, and conduit 819, coupled with conductive strip 810. The adjacently disposed detector 804 is fashioned in similar manner, the upward surface thereof incorporating a resistive surface layer or region formed in cooperation with conductive strips 820 and 822. The lower surface of detector component 804 is formed incorporating a similar resistive layer or region functionally associated with conductive strips 824 and 826. Note that the latter conductive strips are arranged orthogonally with respect to those at 820 and 822. Conductive strip 820 is coupled by a lead or conduit 828 to conductive strip 812 of the detector component 802, while conductive strip 822 is coupled by lead or conduit 830 to conductive strip 810 of detector 802. Thus interconnected, it will be apparent that any interaction occurring within detector component 804 will be "seen" as a charge division between strips 820 and 822, for one coordinate parameter, along leads 828 and 830, as well as output conduits 818 and 819. As is apparent, a desirable simplification of the structure of the composite detector is available with this form of row readout.

Looking to the adjacently disposed row of detector components 806 and 808, it may be noted that detector component 806 is formed incorporating resistive layers or regions in its opposed surfaces aligned for the acceptance of radiation and, additionally, incorporated condutive strips as at 832 and 834 at the extremities of its upward surface as well as orthogonally oriented conductive strips 836 and 838 about the extremities of its lowermost and oppositely disposed surfaces.

Identically structured detector component 808, similarly, is formed having resistive surfaces or regions arranged normally to the direction of radiation impingement. The surfaces also incorporate conductive strips, as at 840 and 842 at the upwardly disposed side and, at 844 and 846, orthogonally disposed at the lowermost surface.

Coupled in similar row-type fashion as detectors 802 and 804, the conductive strips of detectors 806 and 808 are directly electrically associated by leads 848 and 850. Note, in this regard, that lead 848 extends between conductive strips 840 and 832 while lead 850 extends between conductive strips 842 and 834. The output of that particular row at the upward surface of the composite detector is represented by leads 852 and 854. A columnar interconnection of the detector components is provided between the orthogonally disposed conductive strips 814 and 816 of detector 802, respectively, as by leads 856 and 858, to similarly disposed conductive strips 836 and 838 of detector 806. The columnar readouts for the paired detector components are present at conduits 860 and 862 extending, respectively, from conductive strips 836 and 838.

In similar fashion, the columnar association of detector components 804 and 808 is provided by leads 864 and 866 which, respectively, extend between conductive strips 824 and 826 of detector 804 to corresponding conductive strips 844 and 846 of detector component 808. The readouts for the column association of detectors 804 and 808 are provided by conduits 868 and 870 extending, respectively, from conductive strips 844 and 846 of detector component 808.

As in the embodiment of FIG. 20, the output conduits 818, 819 and 852, 854 are of a "row" variety having a designated spatial coordinate parameter and are addressed to initial preamplification stages prior to their association with logic circuitry for deriving imaging information for that particular spatial coordinate. Similarly, the "columnar" outputs at conduits 806, 862 and 868, 870 are directed to preamplification stages, thence to appropriate circuitry for treating that spatial coordinate parameter. It will be understood, of course, that the number of detector components formed within a matrix or array thereof depends upon the field of view desired for a particular camera application as well as the practicalities for retaining such components under appropriate cryogenic temperature conditions during operation.

The foregoing examination of the composite detector structures, represented in FIGS. 20 and 21 reveals certain consistent characteristics between the embodiments. For instance, as alluded to above, the effective areas presented to radiation impingement of the discrete detector components must be substantially equivalent, in order to avoid distortion in an ultimately developed image. Additionally, these components should be as closely nested as possible and aligned such that the spatial coordinate which may be designated for each surface evolves what has been termed as a "row-column" orientation. In the latter regard, an observation of this geometry shows that the leads interconnecting the impedance networks or the impedance structure i.e. at the surface region of the detector components, connect them directly, whether in the parallel-series connection of the embodiment of FIG. 20 or the interconnection of conductive strips shown in FIG. 21. Another aspect typifying the structure of the invention, reveals that any two adjacent surfaces of any two adjacent detector components exhibit spatial coordinate parameters of a common directional sense and, more particularly, two adjacent of the coplanar surfaces of any two adjacent detector components are disposed within a linearly oriented grouping arranged to exhibit a common spatial coordinate parameter directional sense. Because the composite detector embodiments shown in FIGS. 20 and 21 operate substantially in the same functional manner, their outputs are identified with the same spatial coordinate directional labels. For instance, the $x$- designated coordinate outputs at lines 722 and 720 of the embodiment of FIG. 20, respectively, are identified as $(X_1A)$ and $(X_1B)$; while the parallel row $y$- designated coordinate outputs as at lines 742 and 740, respectively, are identified as $(X_2A)$ and $(X_2B)$. Similarly, the orthogonally disposed $y$- designated coordinate parameter outputs, as represented for instance, at lines 762 and 760, respectively, are identified as $(Y_1A)$ and $(Y_1B)$. Next adjacent to that column of the composite detector, are the detectors whose outputs are represented at 780 and 782 and are identified, respectively, as $(Y_2A)$ and $(Y_2B)$. This same labeling procedure will be seen to be utilized in the composite detector embodiment of FIG. 21.

An important aspect of the "row-column" interconnection of the discrete detector components resides in the realization of an effective reduction in that detector linear dimension over which resolution is evaluated. More specifically, an improvement is experienced in the resolution of the camera system which may be expressed by the equation:

$$\Delta x = (\Delta E\, L\,)/E \qquad (20)$$

Where, $\Delta x$, represents spatial resolution in terms of distance; $\Delta E$, is absolute energy resoltuion; $L$, is length of a detector component, as measured parallel to the directional sense of an associated impedance network; and, $E$, represents the energy of an incident photon interacting with the detector. Within the right hand side of equation (20) above, the expression, $\Delta E/E$, is readily identified as the fraction (or percentage) of energy resolution and is fixed for a given input energy. Accordingly any increase in the value of, $L$, directly and adversely affects the spatial resolution. Where the detector components are not interconnected by the "row-column" technique, the value, $L$, in the expression above becomes larger. For example if the detectors pictured in FIG. 22 were connected as a single detector the measuring distance would be $2L$, effecting a doubling of the noted spatial resolution value to the detriment of final imaging. Another feature characteristic of a detector "row-column" interconnection resides in the presence of a common detector component for each combination of an associated row and column. Stated otherwise, a row or column configuration also may be designated as an orthogonally disposed linearly oriented grouping of charge collecting surfaces. Any interaction within any given common component will provide x- and y- designated coordinate output signals from the thus associated linear surface groupings.

A third embodiment for "row-column" interconnection of detector components exhibiting this spatial resolution advantage is revealed in FIG. 22. Referring to that figure, a composite detector formed as an array of discrete detector components is revealed generally at 880. As in the earlier-discussed embodiments, detector or detector portion 880 is shown in exploded fashion for purposes of clarity and comprises a plurality of detector components, four of which are shown at 882, 884, 888, and 886. Components 882-888 are dimensioned having mutually equivalent areas as are intended for acceptance of impinging radiation and are formed as of an orthogonal strip array variety, each strip thereof being defined by grooves formed within the detector surfaces. Of course, other, strip-defining configurations will occur to those skilled in the art. Detector 882 is formed having strips 890a-890d defined by grooves cut within its upward charge collecting surface. The opposite face of detector component 882 similarly is formed having strips 892a-892d defined by intermediately positioned grooves arranged orthogonally with respect to the grooves at the upper surface. Detector component 884 is identically fashioned, having strips 894a -849d formed at its upwardly disposed charge collecting surface; and at its lower surface, orthogonally disposed strips 896a-896d, adjacent said strips being defined by intermediately formed grooves. Similarly, detector component 886 is formed having strips 898a-898d at its upward surface, adjacent ones of the strips being defined by intermediately disposed grooves, while its lower surface similarly is formed having strips 900a-900d defined by intermediately disposed grooves arranged orthogonally with respect to the grooves of the upward surface. Detector component 888 may be observed to have strips 902a-902d at its upward surface adjacent ones of which are defined by intermediately designated grooves, while its lower surface is formed with adjacently disposed strips 904a-904d separated by intermediately disposed grooves arranged orthogonally to the grooves of the upward surface thereof.

In the instant embodiment, strips 894a-894d of detector component 884 are directly, electrically associated with corresponding row strips 890a-890d of components 882 by electrical leads, respectively identified at 906a-906d. Note, that no impedance network is interposed intermediate the strip groupings as in the earlier embodiments. However, an impedance network, designated generally at 908, is associated with the termini of strips 890a-890d opposite the edges thereof is coupled with electrical leads 906a-906d. Network 908 comprises serially associated discrete resistors 910a-910e which are tapped at their common junctions by leads 912a-912d extending, respectively, to strips 890a-890d. The output, or readout points for the thus defined "row" of the composite detector assembly are represented at 914 and 916 and are provided by the same respective spatial or x- designated coordinate parameter output labeling, $(x_1B)$, $(x_1A)$ as are present in the corresponding "row" of the embodiments of FIGS. 20 and 21.

The corresponding upwardly disposed surfaces of components 886 and 888 are connected in similar fashion. For instance, strips 902a-902d are electrically coupled with strips 898a-898d by respective electrical leads 918a-918d. The "row" coupling thus provided is associated with an impedance network shown generally at 920. Network 920 is formed comprising serially associated discrete resistors 922a-922e which are tapped at their common interconnections by leads 924a-924d. Leads 924a-924d, respectively, extend to strips 898a-898d of detector 886. The principal termini of the thus defined "row" are identified at 926 and 928, having outputs respectively labeled $(x_2B)$, $(x_2A)$.

Looking now to the lower surfaces of the detector components, the orthogonally disposed strips of detector component 882 are electrically coupled as shown with the corresponding strips of detector component 886 by electrical leads 930a-930d. The thus coupled strip arrays of those detector components are associated in "columnar" fashion with an impedance network identified generally at 932. Network 932 comprising serially associated discrete resistors 934a-934e, the interconnections between which are connected as shown with strips 900a-900d of component 886 by leads respectively identified at 936a-936d. The readout termini for the thus defined "column" association of detectors 886 and 882 are present at 938 and 940 and the cooresponding spatial or y-designated coordinate parameter outputs are identified respectively as $(y_1A)$ and $(y_1B)$.

The lower surfaces of detector components 884 and 888 similarly are associated in "columnar" readout fashion, strips 896a-896d of the former being electrically connected through respective leads 940a-940d to strips 904a-904d of the latter. The thus established "columnar" readout is associated with an impedance network identified generally at 942 and comprising serially associated discrete resistors 944a-944e. Strips 904a-904d, respectively, are coupled with the interconnection of the resistors 944a-944e of network 942 by leads 946a-946d. As in the earlier embodiments, the principal readouts of the thus defined "columnar" detector component coupling are represented at 948 and 950 and their spatial coordinate parameter outputs are labeled, respectively, $(y_2A)$ and $(y_2B)$. From the foregoing description of the composite detector arrangement 880 it may be observed that the row-column association of the components thereof enjoys the noted spatial resolution advantages, however, the time constant characteristic thereof will reflect a higher capacity evaluation.

Figure 23:
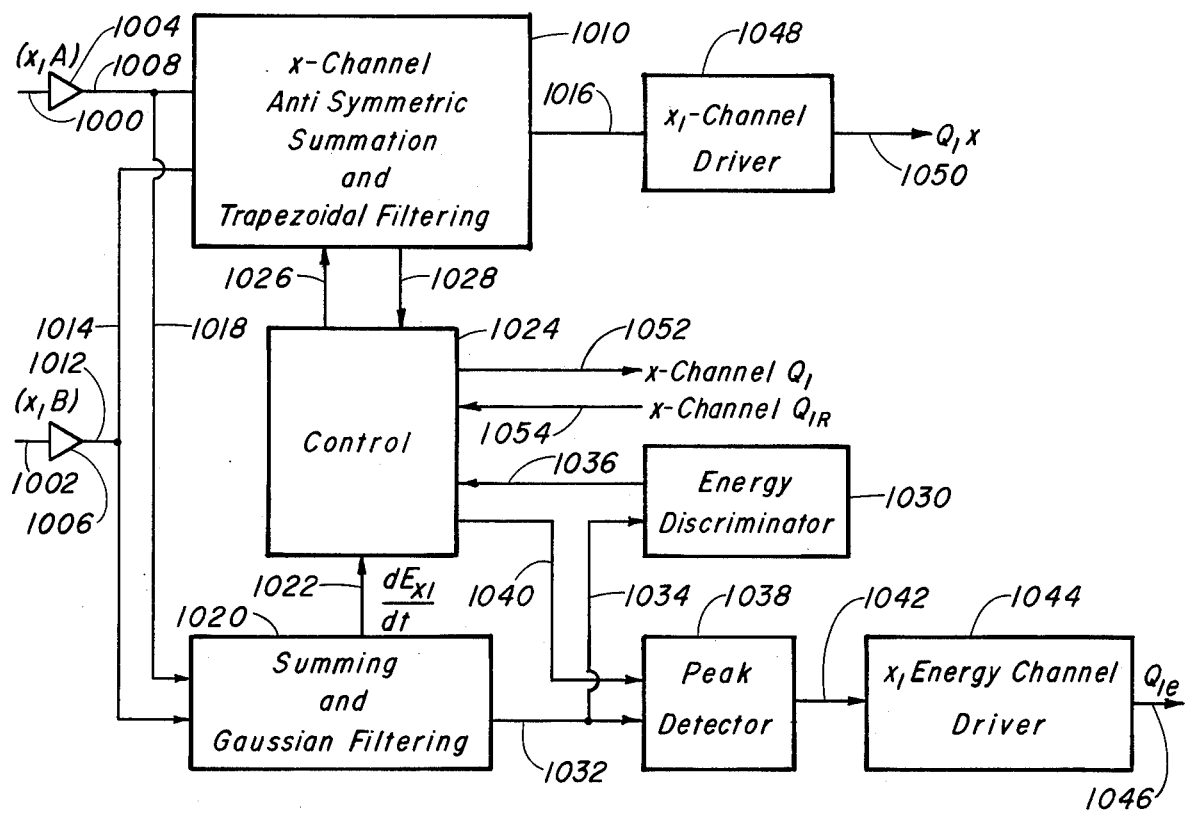
FIG. 23 is a block schematic diagram of a control system utilized in treating one spatial channel output of the noted "row-column" detector component interconnection geometry.
Figure 24:
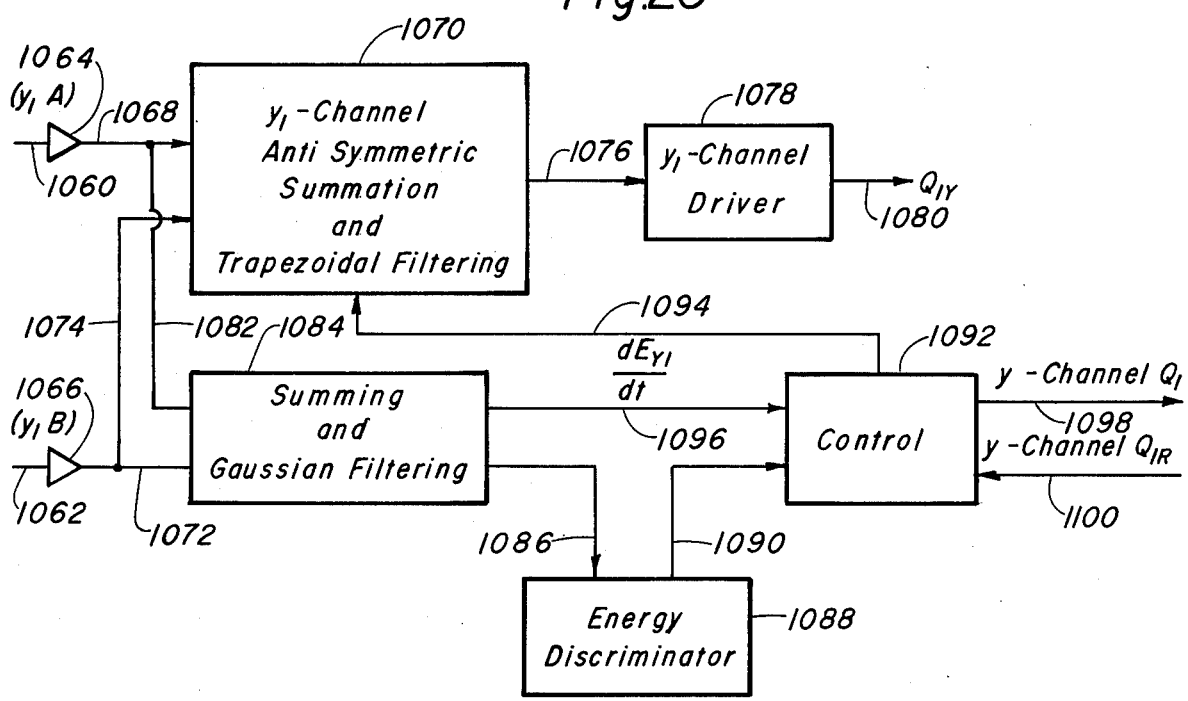
FIG. 24 is a schematic block diagram of a control circuit operating in conjunction and cooperation with the control system of FIG. 23.

FIGS. 23 and 24 reveal filtering and control electronics which operate in conjunction with the quadrant of composite detectors arrayed in the "row-column" manner described hereinabove in connection with FIGS. 20-22. Note that the spatial coordinate parameter outputs from the arrays shown in those figures are designated $(x_1A)$, $(x_1B)$ and $(x_2A)$, $(a_2B)$ for the row readouts and $(y_1A)$, $(y_1B)$ and $(y_2A)$, $(y_2B)$ for the corresponding columnar readouts. Looking to FIG. 23, the x-channel spatial coordinate parameter outputs as are derived from one such x-channel row type readout, to wit $(x_1A)$, $(x_1B)$ are again reproduced at input lines 1000 and 1002, representing the input addressing respective discrete preamplification stages 1004 and 1006. It should be understood that each row within each quadrant would incorporate the initial or first signal treating functions, including the control electronics revealed in FIG. 23 and that the components to be described in connection therewith are substantially identical in function as those described heretofore under substantially the same labeling, the description now being reduced to single channel analysis in the interest of clarity and simplicity. The output at line 1008 of preamplification stage 1004 is introduced to an x-Channel Antisymetric Summation and Trapezoidal Filtering function 1010, while the corresponding input from preamplification stage 1006 is directed through lines 1012 and 1014 to that same function. The Summing and Trapezoidal function at 1010 operates on the $x_1$-Channel spatial signals introduced thereto in the same fashion as described above in connection with the FIGS. 12–16. For instance, the inputs from the $x_1$-Channel are subtractively summed and, following appropriate Trapezoidal Filtering and Guassian Shaping, for instance, by the noted series of integrations or the like, an output from function block 1010 is provided at line 1016.

The outputs of amplification stages 1004 and 1006 also are directed, respectively, through lines 1008, 1018 and 1012, and 1014, to the Summing and Gaussian Filtering function 1020. As described earlier in detail in conjunction with FIGS. 12–16, function 1020 includes an initial stage deriving the time derivative of the summed energy signal provided through lines 1014 and 1018 and submits such derivative signal, from along line 1022, to a Control function depicted generally at 1024. When this signal evidences a predetermined requisite level to provide a preliminary assurance of valid spatial information, a start logic function within block 1024 responds to provide gate control over the Filtering and Summation function at block 1010. Controls over gates and the like of function 1010 are asserted, for instance, from lines as at 1026, while appropriate information feedback is derived from the Filtering and Summation function 1010 from communication line 1028. Control 1024 also communicates with an Energy Discriminator function 1030 which receives the summed energy signal output of block 1020 from along lines 1032 and 1034. As in the earlier embodiments, Energy Discriminator 1030 provides a pulse-height analysis of the energy signal deriving from Summing function 1020 for purposes of evolving an initial evaluation thereof as to the presence or absence of valid image information. For instance, discriminator 1030 evaluates the energy signals in correspondence with the lowest photon energy level to be accepted from those radioisotopes extant within the noted region of clinical interest. Appropriate acceptance or rejection of the energy level is signalled along line 1036 to Control function 1024 and, in the absence of an appropriate such level, the latter function serves to reset the system by carrying out the earlier-described short-cycle operation. As in the earlier embodiments, the circuits of FIG. 23 further includes a Peak Detector function 1038. Associated with Control 1024 through line 1040 and receiving the summed or energy signal from block 1020 through line 1032, Peak Detector 1038 serves to hold the peak value of the signal passed thereto to provide an analogue storage function for accommodating variations in signal treatment at times as are represented, for instance, between Antisymmetric Summation and Trapezoidal Filtering function 1010 and Summing and Gaussian Filtering function 1020. The peak value output of Detector 1038 is presented along line 1042 to an energy channel driver 1044 for ultimate presentment to quadrant processing control circuitry from along line 1046. Note that the energy channel signal at that line is identified as, $Q_{1e}$.

The output at line 1016 of Antisymmetric Summation and Trapezoidal Filtering function 1010 is presented to an $x_1$-Channel driver 1048 for delivery to quadrant processing control circuitry through line 1050. Note, as in the earlier embodiments, this coordinate channel signal is identified by the label $Q_{1x}$. Similarly, the output of control block 1024 is provided at line 1052 and the coordinate channel signal thereat is identified by the label "x-Channel $Q_1$." Additionally, for purposes of effecting a full cycle or short cycle termination, an input provided at line 1054 for carrying such appropriate signal is labeled "x-Channel $Q_{IR}$."

Looking to FIG. 24, the corresponding initial input treating or columnar or y-Channel processing circuit is revealed, it again being understood that this circuit represents that associated with only one column within a "row-column" detector component array, similarly such circuits being required for each such column. Of course, the term "row" or "column" are for descriptive purposes only and designate one given coordinate parameter of directional readout from a detector matrix or mosaic. Looking to the figure, column readouts $(y_1A)$, $(y_1B)$ are asserted, respectively, at input lines 1060 and 1062 of input preamplification stages 1064 and 1066. The output of amplification stage 1064 is directed through line 1068 to a $y_1$-Channel Antisymmetric Summation and Trapezoidal Filtering function 1070 performing the operations described hereinabove. Similarly, the output of preamplification stage 1066 is introduced through lines 1072 and 1074 to signal treatment at function 1070, the $y_1$-Channel signals being subtractively summed, appropriately filtered and pulse-shaped as by a series of integrations to provide a y-Channel signal at line 1076. This signal is introduced through a $y_1$-Channel Drivers 1078 from which it exits at line 1080 for introduction as a signal designated "$Q_1y$" to second or further treatment at a processing control function.

The $y_1$-Channel signals also are introduced from lines 1082 and 1072 to a Summing and Gaussian Filtering function 1084 which additively sums and filters the signals to generate an energy signal which is submitted, as through line 1086, to an Energy Discriminator function 1088. As before, Energy Discriminator 1088 carries out a pulse height analysis of the energy signal to provide an accurate evaluation thereof as to the presence or absence of valid image information. The lower value selected for this analysis corresponds with the acceptable lower value for the lowest photon energy selected for recepit and treatment by the system. The output of discriminator function 1088 is directed through line 1090 to Control function 1092. In addition to providing appropriate gate control over Summation and Filtering function 1070 through line 1094, Control function 1092 also receives the time derivative of the $y_1$-Channel energy signal from along line 1096. As in the earlier embodiments, this signal generally is obtained from an initial stage within Summing and Gaussian Filtering operations performed at block 1084. This derivative signal serves both to provide an appropriate start signal logic for the Control 1092, as described earlier herein and, additionally, will be seen to provide a coincidence signal for later control over the entire multi-component detector arrangement of the invention. The output of control function 1092 is present at line 1098 and is identified, for illustrative purposes, as "y-Channel $Q_1$". This signal is introduced to the noted second or further treatment at a processing control function, that same circuitry providing a reset input to control 1092 identified as "y-Channel $Q_{IR}$" and submitted from along line 1100.

Figure 25:
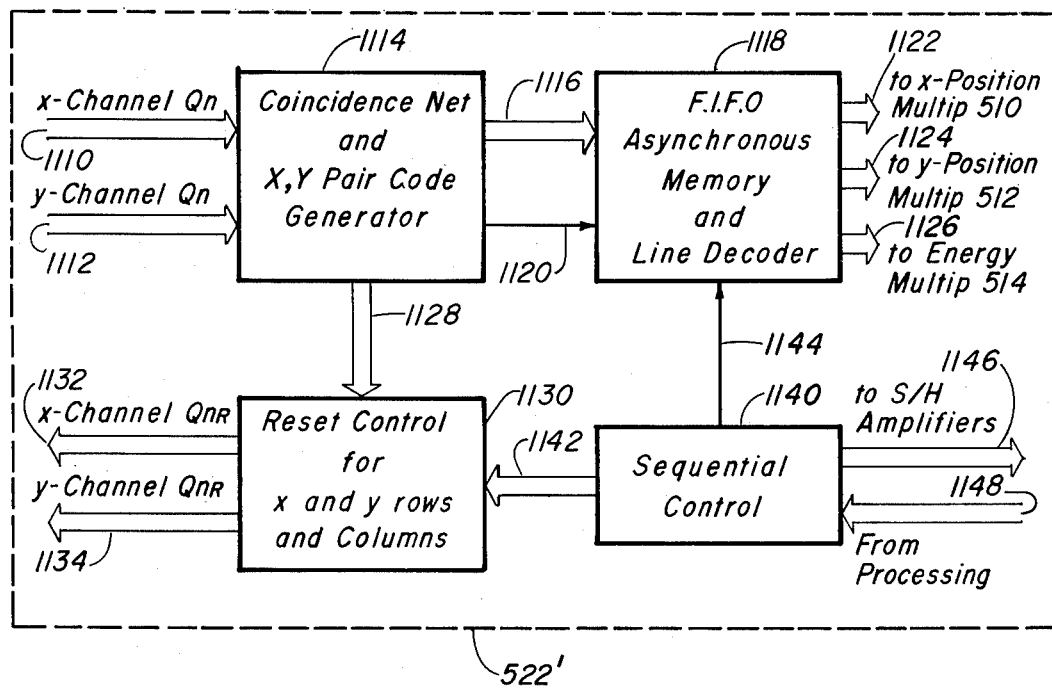
FIG. 25 is a block diagram of a control arrangement for utilization with the noted "row-column" interconnection of detector components, the figure representing an alternate control arraignment within the diagram of FIG. 19.

Turning now to FIGS. 19 and 25, the second treating or quadrant processing control arrangement for use with the "row-column" readout arrangements for detector arrays remains substantially similar to the system described above in connection with FIG. 19. However, in consequence of the isolated readout geometry necessarily present in a "row-column" interconnection, a further arrangement is required to properly identify and treat a data pair input deriving from the given x- and y-Channel outputs of any given detector component within the array. Accordingly, the quadrant interface control function represented in FIG. 19 within dashed boundary 522 is replaced by the slightly revised arrangement at 522' in FIG. 25. For purposes of clarity, the latter drawing incorporates broadened arrows to represent a multi-line input as would be derived from the multiple channels of networks of FIGS. 23 and 24 as well as the multiple line couplings already depicted in FIG. 19. Further in this regard, to represent the several inputs from each row of the detector array, typical ones of which are represented in FIG. 23 as "x-Channel $Q_1$", and in FIG. 24 as "y-Channel $Q_1$", the corresponding multiple channel input for such readouts is identified as "x-Channel $Q_n$," and "y-Channel $Q_n$." Additionally, the reset signals from the processing circuitry at FIG. 25 are generally denoted by the labels "x-Channel $Q_{nR}$" and "y-Channel $Q_{nR}$". These labels represent typical reset signals, two of which were identified above in connection with the description associated with FIGS. 23 and 24 at respective lines 1052 and 1100. Looking now in detail to FIG. 25, x-Channel $Q_n$ signals, as well as y-Channel $Q_n$ are submitted from each respective row and column readout through input conduits, represented generally at 1110 and 1112, to a Coincidence Network and x, y Pair Code generator function 1114. Network 1114 provides a read-in function which checks the inputs at 1110 and 1112 corresponding to a given gamma ray interaction within a given detector component for the coincidence of their time derivative signals. when the coincidence of such a data pair is received, the spatial position represented by such signals is assured and a corresponding x, y Pair Code is generated and presented through appropriate conduits represented generally by the transfer conduit at 1116. This pair code output is inserted into F.I.F.O. Asynchronous memory and Line Decoder function 1118 by virtue of a clocked signal or pulse provided through line 1120. F.I.F.O. Asynchronous Memory 1118 corresponds with the same function provided at 516 in FIG. 19. As before, the F.I.F.O. (first-in, first-out) memory is conventionally formed incorporating generally independent input and output stages or networks. It serves within the system as a de-randomizer which receives and collects or records the x, y Pair Codes from circuit 1114 and, following a four-to-three line decoding thereof, submits signals to multiplexers 510–514 (FIG. 19) providing for the selective acceptance of the signals addressed thereto. Note in the latter regard, that the signal labeling for the instant embodiment remains the same as that shown in FIG. 19. These coded instructions to the noted multiplexers are represented in FIG. 25 by the broad conduit arrows appropriately labeled and respectively identified at 1122–1126.

Returning to the Coincidence Network and Pair Code Generator function 1114, in the absence of a noted signal coincidence identifying a proper spatial pair code, appropriate signal return channel alignment will be provided through a multi-channel conduit represented generally at 1128 to a Reset Control function 1130. Operating in similar fashion at reset drive function 520 in FIG. 19, control 1130 responds to a non-coincidence condition to provide for the resetting of appropriate ones of the row or column readout networks as described in connection with FIGS. 23 and 24. In this regard, note that multiple row reset outputs are represented generally by arrow 1132, while the corresponding column or y-Channel output signals are directed through a conduit arrangement represented generally at 1134. As noted above, the signals labeled at the latter two outputs are representative of multi-row and multi-column interconnections. Reset signal transmitting control over Reset Control 1130 is derived from Sequential Control block 1140 as through the conduit represented generally at 1142. Control 1140 additionally provides the functions described in connection with block 526 in FIG. 19, i.e. clocking the information codes from F.I.F.O. Asynchronous Memory and Line Decoder 1118 by outputs submitted thereto through line 1114; controlling the Sample and Hold Amplifiers 544, 548 and 552 to receive information from Multiplexers 510 and 514 and assert appropriate delays suited for the proper operation of Two Channel Analyser 562, so as to assure that a signal of proper energy level criteria is processed. Further, function 1140 activates Reset Control 1130 to generate end-of-cycle resetting as well as short cycle resetting performance occasioned with the failure of a given signal to pass the window criteria of analyser 562. The outputs of Control 1140 to the noted Sample and Hold Amplifiers are represented generally by the broad arrow at 1146, while the corresponding input thereto from the processing system providing for the noted resetting or recycling features is represented by the broad arrow designated 1148.

With the noted replacement of processing control 522' for that earlier represented at 522 in FIG. 19, the system operates essentially in the same manner, i.e., multiple channel analysis being carried out over the several energy levels which may be provided by components of the general type described at 562; sample and hold functions are carried out, as described at 544–552; and a dividing function is provided to normalize the signals with respect to their corresponding energy levels by divider functions as at 584 and 586 in FIG. 19.

Since certain changes may be made in the system and apparatus without parting from the scope of the invention herein involved, it is intended that all matter contained in the above description or shown in the accompanying drawings shall be interpreted as illustrative and not in a limiting sense.

We claim:

1. In a system for imaging the distribution within a region of interest of isotopic materials emitting radiation of given photon energy, said system including composite solid state detector means having a plurality of discrete components which are operationally associated to provide spatial coordinate parameter outputs representative of the spatial disposition of corresponding interactions of said radiation with said detector means, the improvement comprising:

first output treating means connected to receive said spatial coordinate parameter outputs of said detector means components, actuable to selectively filter and sum said outputs to derive corresponding coordinate channel signals and an energy channel signal having values corresponding respectively with said spatial disposition and given photon energy exhibited at a said interaction, said first output treating means further including control means for effecting said actuation to filter and sum and for deriving a data acceptance signal in correspondence with said coordinate and energy channel signals, said control means being responsive to a received reset signal to reset said first output means to a clear condition;

means including spatial coordinate multiplexer means and energy channel multiplexer means respectively coupled to be addressed by said energy channel signals, each said multiplexer means being responsive to a coded actuating signal to effect a transference of said channel signals addressed thereto;

process control means including memory means for receiving said data acceptance signals and selectively retaining them in received serialized fashion, and actuable to derive said coded actuating signal in correspondence with said serialized data acceptance signals;

sequential control means for selectively actuating said process control means and regulating an operational cycle of said system; and second treating means responsive to said transferred channel signals for deriving readout information representative thereof.

2. The improved system of claim 1 including; storage means, having receive and hold modes, for receiving, when transferred, each said coordinate and energy channel signal when in said receive mode, and actuable to assume said hold mode retaining each said channel signal over a given interval, said storage means having outputs for asserting each said retained channel signal; and wherein said sequential control means is configured for selectively actuating said storage means to derive and retain said hold mode for said given interval.

3. The improved system of claim 2 in which said sequential control means is configured for deriving and submitting said reset signal to said control means in correspondence with said storage means actuation.

4. In a system for imaging the distribution within a region of interest of isotopic materials emitting radiation exhibiting two or more levels of photon energy, said system including composite solid state detector means having a plurality of discrete components which are operationally associated to provide spatial coordinate parameter outputs representative of the spatial disposition of corresponding interactions of said radiation with said detector means, the improvement comprising:

first output treating means connected to receive said spatial coordinate parameter outputs of said detector means components, actuable to selectively filter and sum said outputs to derive corresponding coordinate channel signals and an energy channel signal having values corresponding respectively with said spatial disposition and the level of said photon energy exhibited at a said interaction, and including control means for effecting said actuation to filter and sum and for deriving a data acceptance signal in correspondence with said coordinate and energy channel signals, said control means being responsive to a reset said first output means to a clear condition;

means including spatial coordinate multiplexer means and energy channel multiplexer means respectively coupled to be addressed by said coordinate channel and said energy channel signals, each said multiplexer means being responsive to a coded actuating signal to effect a transference of said channel signals addressed thereto;

process control means including means for receiving said data acceptance signals to effect a de-randomization thereof and actuable to provide a said coded actuating signal in correspondence with a said data acceptance signal;

second treating means including divider network means responsive to a said energy channel multiplexer means transferred energy channel signal and to said spatial coordinate multiplexer means transferred signals for normalizing said spatial coordinate channel signals with respect to the said photon energy related value of their corresponding said energy channel signal, said second treating means being configured for deriving readout information corresponding with said normalized spatial coordinate channel signals; and sequential control means for selectively actuating said process control means and regulating an operational cycle of said system.

5. The improved system of claim 4 wherein said divider network is configured to carry out said normalization by effecting a division of the value of each said spatial coordinate channel signal by the value of said energy channel signal.

6. The improved system of claim 5 wherein said second treating means include means for evaluating the peak value of each said energy channel signal with respect to predetermined upper and lower limit values selected in correspondence with each said level of photon energy exhibited by said isotopic materials.

7. In a system for imaging the distribution within a region of interest of isotopic materials emitting radiation of given photon energy or energies, said system including composite solid state detector means having a plurality of discrete components which are operationally associated within predetermined portions of said detector means to provide spatial coordinate parameter, $x$-, $y$- designated outputs representative of the spatial disposition of corresponding interactions of said radiation with said detector means, the improvement comprising:

first output treating means connected to receive said spatial coordinate parameter, $x$-, $y$- designated outputs of said components of each said predetermined portion of said detector means, actuable to selectively filter and sum said outputs when operating from a clear condition to derive corresponding $x$- and $y$- designated coordinate channel signals and an energy channel signal having values corresponding respectively with said spatial disposition and given energy exhibited at a said interaction, said first output treating means including first evaluating means responsive to the value of said given energy equaling or exceeding a predetermined value to derive a select output, and further including control means responsive to the presence of said evaluating means select output for effecting said actuation to filter and sum and for deriving a data acceptance signal in time correspondence with said coordinate channel and energy channel signals, said control means being responsive to a reset signal when submitted thereto to reset said first output treating means to said clear condition;

means including $x$-position multiplexer means, $y$-position multiplexer means and energy multiplexer means respectively coupled to be addressed by said $x$- and $y$- designated coordinate and energy channel signals, each said multiplexer means being responsive to a coded actuating signal to transfer said channel signals addressed thereto;

storage means, having receive and hold modes, for receiving each transferred said channel signal then in said receive mode, and actuable to assume said hold mode retaining each said channel signal over a given interval, said storage means having outputs for asserting each said retained channel signal;

process control means including asynchronous memory means for accepting and retaining said data acceptance signals in received serialized fashion and actuable to provide said coded actuating signal;

sequential control means for selectively actuating said process control means to effect selective transfer of said channel signals to said storage means, and for actuating said storage means to derive and retain said hold mode for said given interval; and second treating means responsive to said channel signals asserted at said storage means outputs for deriving readout information representative thereof.

8. The improved system of claim 7 in which said process control means asynchronous memory means is configured and arranged for de-randomizing the receipt of said data acceptance signals to effect said serialization in a time domain independent of the rate of said receipt.

9. The improved system of claim 7 in which said sequential control means is configured and arranged for generating and submitting a said reset signal subsequent to said actuation of said storage means to assume said hold mode.

10. The improved system of claim 7 wherein:
said second treatment means includes second evaluating means for evaluating the peak value of each said energy channel signal over a given interval of time, and having a select output when said energy channel signal peak value lies within predetermined limits; and said sequential control means is configured and arranged for generating said reset signal in the absense of said second evaluating means select output.

11. The improved system of claim 10 in which said sequential control means is configured and arranged for generating said reset signal in the absence of said second evaluating means select output and at the termination of said second evaluating means given interval of time.

12. The improved system of claim 7 in which said first output treating means includes peak detector means configured and arranged for receiving and retaining the peak value of a said summed, filtered x-, y- designated output deriving said energy channel signal at least until said storage means actuation.

13. The improved system of claim 7 in which said second treatment means includes divider network means responsive to the said x- and y- designated coordinate channel signals for normalizing said signals with respect to the photon energy of their derivative said interaction.

14. The improved system of claim 7 in which said second treatment means includes: first divider network means coupled to receive said x- designated coordinate channel signal asserted at a said storage means output; and second divider network means coupled to receive said y-designated coordinate channel signal asserted at a storage means output; said first and second divider networks being configured and arranged in operative association with the said energy channel signal output asserted at a said storage means output to effect a division of the values of said coordinate channel signals by the value of the corresponding said energy channel to provide x- and y- designated spatial signals normalized with respect to the said energy channel signal value; said second treatment means deriving said readout information from said normalized x- and y- designated spatial signals.

15. The improved system of claim 7 in which:
said process control means is configured and arranged for de-randomizing the receipt of said data acceptance signal to effect said serialization in a time domain independent of the rate of said receipt; and wherein said sequential control means is configured and arranged for generating and submitting a said reset signal subsequent to said actuation of said storage means to assume said hold mode.

16. The improved system of claim 7 in which:
said second treatment means includes second evaluating means for evaluating the peak value of each said energy channel signal over a select interval of time, and having a select output when said energy channel signal peak value lies within predetermined limits; and said sequential control means is configured and arranged for said actuation of said storage means to derive a said hold mode given interval substantially in correspondence with said second evaluating means select interval, and the generating said reset signal in the absence of said second evaluating means select output.

17. The improved system of claim 16 in which said first output treating control means is configured and arranged to reset said first output treating means to said clear condition in the absence of said first evaluating means select output.

18. The improved system of claim 17 in which said sequential control means is configured and arranged for generating and submitting a said reset signal subsequent to said actuation of said storage means to assume said hold mode.

19. The improved system of claim 18 in which said first output treating means includes peak detector means configured and arranged for receiving and retaining the peak value of a said summed, filtered x-, y- designated output deriving said energy channel signal at least until said storage means actuation.

20. The improved system of claim 19 in which said second treatment means includes divider network means responsive to the said x- and y- designated coordinate channel signals for normalizing said signals with respect to the photon energy of their derivative and interaction.

21. The improved system of claim 19 in which said second treatment means includes: first divider network means coupled to receive said x- designated coordinate channel signal asserted at a said storage means output; and second divider network means coupled to receive said y- designated coordinate channel signal asserted at a said storage means output; said first and second divider networks being configured and arranged in operative association with the said energy channel signal output asserted at a said storage means output to effect a division of the values of said coordinate channel signals by the value of the corresponding said energy channel signal to provide x- and y- designated spatial signals normalized with respect to the said energy channel signal value; said second treatment means deriving said readout information from said normalized x- and y- designated spatial signals.

22. The improved system of claim 21 in which said process control means asynchronous memory means is configured and arranged for de-randomizing the receipt of said data acceptance signals to effect said serialization in a time domain independent of the rate of said receipt.

23. In a system for imaging the distribution within a region of interest of isotopic material emitting radiation of given photon energy, said system including composite solid state detector means having a plurality of mutually adjacently disposed discrete detector components each having one of two oppositely disposed charge collecting surfaces positioned substantially within a common plane for exposure to said radiation, said components being arranged to establish linearly oriented groupings of respective said opposed surfaces, each said grouping of surfaces being electrically intercoupled and associated with impedance means for providing x- and y- designated coordinate outputs from respective mutually orthogonally aligned and oppositely disposed ones of said groupings associated with a common said detector component at which an interaction with said radiation corresponding with said coordinate output occurs, the improvement comprising:

x- coordinate output treating means responsive to said x- designated coordinate outputs, actuable to selectively filter and sum said outputs from a clear condition to derive corresponding x- designated coordinate channel signals and an energy signal having values corresponding respectively with a coordinate aspect of the spatial location of said interaction and the value of said photon energy thereof, and including control means for effecting said actuation to filter and sum and for deriving an x- data signal corresponding with said channel and energy signals, said control means being responsive to a reset signal when submitted thereto to reset said treating means to said clear condition;

y- coordinate output treating means responsive to said y- designated coordinate outputs, actuable to selectively filter and sum said outputs from a clear condition to derive corresponding y- designated coordinate channel signals and an energy signal having values corresponding respectively with a coordinate aspect of the spatial location of said interaction and the value of said photon energy thereof, and including control means for effecting said actuation to filter and sum and for deriving a y- data signal corresponding with said channel and energy signals, said control means being responsive to a reset signal when submitted thereto to reset said treating means to said clear condition;

means including x- position multiplexer means, y- position multiplexer means and energy multiplexer means, respectively coupled to be addressed by said x- and y- designated coordinate channel signals and at least one said energy signal, each said multiplexer means being responsive to a coded actuating signal to transfer said signals addressed thereto;

process control means including coincidence network means responsive the said x- data and y- data signals corresponding with a given said interaction for deriving a pair code signal, and asynchronous memory means responsive to said pair code signal for accepting and retaining said x- and y- data signals in received serialized fashion and actuable to provide and assert said coded actuating signal at said multiplexer means;

means responsive to said x- and y- designated coordinate channel signals when transferred from said x- position multiplexer means, said y- position multiplex means, and energy multiplexer means for deriving readout information representative thereof; and sequential control means for selectively actuating said process control means to effect said transfer of said signals.

24. The improved system of claim 23 including:

storage means, having receive and hold modes, for receiving, when transferred, each said channel and energy signal when in said receive mode, and actuable to assume said hold mode retaining each said channel signal over a given interval, said storage means having outputs for asserting each said retained channel signal; and wherein said sequential control means is configured and arranged for selectively actuating said storage means to derive and retain said hold mode for said given interval.

25. The improved system of claim 23 in which each said x- coordinate output treating means and said y- coordinate output treating means include first evaluating means responsive to the value of said energy signal equaling or exceeding a predetermined value to derive a select output; and said control means is responsive to the presence of said select output for effecting said actuation to filter and sum.

26. The improved system of claim 23 in which:

each said x- coordinate output treating means and said y- coordinate output treating means include a summing network for deriving said energy signal, said summing network including a stage deriving a derivative signal representing the time derivative of said energy values of said coordinate output signals; and the said control means of each said output treating means is responsive to said derivative signal for deriving a designated said x- data or y- data signal.

27. The improved system of claim 26 in which:

each said x- coordinate output treating means and said y- coordinate output treating means includes comparator means responsive to the value of said summing network stage derivative signal equaling or exceeding a predetermined reference value for deriving a given output; and each said control means of a said output treating means is responsive to said given output to effect said actuation and derive a designated said x- data or y- data signal.

28. The improved system of claim 23 in which said process control means asynchronous memory means is configured and arranged for de-randomizing the receipt of said x- and y- data signals to effect said serialization in a time domain independent of the rate of said receipt.

29. The improved system of claim 23 in which said sequential control means is configured and arranged for deriving and submitting said reset signal to said control means subsequent to said actuation of said process control means.

30. The improved system of claim 29 including:

storage means, having receive and hold modes, for receiving, when transferred, each said channel and energy signal when in said receive mode, and actuable to assume said hold mode retaining each said channel signal over a given interval, said storage means having outputs for asserting each said retained channel signal; and wherein said sequential control means is configured and arranged for selectively actuating said storage means to derive and retain said hold mode for said given interval.

31. The improved system of claim 30 in which each said x- coordinate output treating means and said y- coordinate output treating means include first evaluating means responsive to the value of said energy signal equaling or exceeding a predetermined value to derive a select output; and said control means is responsive to the presence of said select output for effecting said actuation to filter and sum.

32. The improved system of claim 31 in which:
each said x- coordinate output treating means and said y- coordinate output treating means include a summing network for deriving said energy signal, said summing network including a stage deriving a derivative signal representing the time derivative of said energy values of said coordinate output signals; and
the said control means of each side output treating means is responsive to said derivative signal for deriving a designated said x- data or y- data signal.

33. The improved system of claim 31 in which:
each said x- coordinate output treating means and said y- coordinate output treating means include a summing network for deriving said energy signal, said summing network including a stage deriving a derivative signal representing the time derivative of said energy value of said coordinate output signals; and
the said control means of each said output treating means is responsive to said derivative signal for deriving a designated said x- data or y- data signal.

34. The improved system of claim 33 in which:
each said x- coordinate output treating means and said y- coordinate output treating means includes comparator means responsive to the value of said summing network stage derivative signal equaling or exceeding a predetermined reference value for deriving a given output; and
each said control means of a said output treating means is responsive to said given output to effect said actuation and derive a designated said x- data or y- data signal.

35. The improved system of claim 23 including: storage means, having receive and hold modes, for receiving, when transferred, each said channel and energy signal when in said receive mode, and actuable to assume said hold mode retaining each said channel signal over a given interval, said storage means having outputs for asserting each said retained channel signal;
wherein said sequential control means is configured and arranged for selectively actuating said storage means to derive and retain said hold mode for said given interval; and
wherein each said x- coordinate output treating means and said y- coordinate output treating means include first evaluating means responsive to the value of said energy signal equaling or exceeding a predetermined value to derive a select output; and said control means is responsive to the presence of said select output for effecting said actuation to filter and sum.

36. The improved system of claim 35 in which:
each said x- coordinate output treating means and said y- coordinate output treating means include a summing network for deriving said energy signal, said summing network including a stage deriving a derivative signal representing the time derivative of said energy values of said coordinate output signals; and
the said control means of each said output treating means is responsive to said derivative signal for deriving a designated and x- data or y- data signal.

37. The improved system of claim 36 in which said sequential control means is configured and arranged for generating and submitting a said reset signal subsequent to said actuation of said storage means to assume said hold mode.

38. The improved system of claim 36 wherein:
said means for deriving said readout information includes second evaluating means for evaluating the peak value of each said energy signal over a given interval of time, and having a select output then said energy signal peak lies within predetermined limits; and
said sequential control means is configured and arranged for generating and submitting a reset signal in the absence of said second evaluating means select output.

39. The improved system of claim 38 in which said sequential control means is configured and arranged for generating said reset signal in the absence of said second evaluating means select output and at the termination of said second evaluating means given interval time.

40. The improved system of claim 36 in which said means for deriving readout information includes divider network means responsive to the said x- designated coordinate channel signals and y- designated coordinate channel signals for normalizing said signals with respect to the photon energy of their derivative said interaction.

41. The improved system of claim 36 in which said means for deriving readout information includes; first divider network means coupled to receive a said x- designated coordinate channel signal asserted at a said storage means output; and second divider network means coupled to receive a said y- designated coordinate channel signal asserted at a said storage means output; said first and second divider networks being configured and arranged in operative association with the said energy signal output asserted at a said storage means output to effect a division of the values of said coordinate channel signals by the value of their corresponding said energy signal to provide x- and y- designated spatial signals normalized with respect to the said energy signal value; said second treatment means deriving said readout information from said normalized x- and y- designated spatial signals.

* * * * *